US006509017B1

(12) United States Patent
Bergström et al.

(10) Patent No.: US 6,509,017 B1
(45) Date of Patent: *Jan. 21, 2003

(54) 66 KDA ANTIGEN FROM BORRELIA

(75) Inventors: Sven Bergström, Umea (SE); Alan George Barbour, Newport Beach, CA (US)

(73) Assignee: Symbicom Aktiebolog, Mölndal (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/470,638

(22) Filed: Jun. 6, 1995

Related U.S. Application Data

(62) Division of application No. 08/262,220, filed on Jun. 20, 1994, now Pat. No. 6,054,296, which is a continuation-in-part of application No. 08/079,601, filed on Jun. 22, 1993, now Pat. No. 5,523,089, which is a continuation of application No. 07/924,798, filed on Aug. 6, 1992, now abandoned, which is a continuation of application No. 07/422,881, filed on Oct. 18, 1989, now abandoned.

(30) Foreign Application Priority Data

Oct. 24, 1919 (DK) .............................. 5902/88

(51) Int. Cl.$^7$ ...................... A61K 39/38; A61K 39/02; C12P 21/06; C12N 15/09

(52) U.S. Cl. .............................. 424/184.1; 424/184.1; 424/234.1; 424/262.1; 435/69.1; 435/69.3; 530/350

(58) Field of Search .................... 424/184.1, 262.1, 424/234.1; 435/69.1, 69.3; 530/350

(56) References Cited

U.S. PATENT DOCUMENTS

| | | | |
|---|---|---|---|
| 5,279,938 A | | 1/1994 | Rosa |
| 5,523,089 A | * | 6/1996 | Bergstrom et al. ....... 424/262.1 |

FOREIGN PATENT DOCUMENTS

| | | |
|---|---|---|
| EP | 0 366 238 A2 | 5/1990 |
| EP | 0 540 457 A1 | 5/1993 |
| WO | 90/04411 | 5/1990 |
| WO | 93/04175 | 3/1993 |

OTHER PUBLICATIONS

Bunikis et al., "Molecular analysis of a 66-kDa protein associated with the outer membrane of Lyme disease Borrelia", FEMS Microbiology Letters 131 (1995), pp. 139–145.

"Immunization Practices Advisory Committee", Clinical Pharmacy, vol. 8, Dec. 1989, pp. 839–851.

Nilsson et al., "Immunibilization and purification of enzymes with staphylococcal protein A gene fusion vectors", The EMBO Journal, vol. 4, No. 4, 1985, pp. 1075–1080.

Orkin, H. Stuart et al., Report and Recommendations of the Panel to Assess the NIH Investment in Research on Gene Therapy, Dec. 7, 1995.

Probert, et al., "Identification and Characterization of a Surface–Exposed 66–Kilodalton Protein from *Borrelia Burgdorferi*", Infection and Immunity, May 1995, vol. 63, No. 5, pp. 1933–1939.

Rosa, et al., "Polymerase chain reaction analyses identify two distinct classes of *Borrelia burgdorferi*", Journal of Clinical Microbiology, vol. 29, No. 3, Mar. 1991, pp. 524–532.

Schaible et al., "Monoclonal antibodies specific for the outer surface protein A (OspA) of *Borrelia burgdorferi* prevent *Lyme borreliosis* in severe combined immunodeficiency (scid) mice", Proc. Natl. Acad. Sci. USA, May 1990, vol. 87, pp. 3768–3772.

Schmitz et al., "Characterization of the Protective Antibody Response to *Borrelia burgdorferi* in Experimentally Infected LSH hamsters", Infection and Immunity, Jun. 1991, vol. 59, No. 6, pp. 1916–1921.

Scriba et al., "The 39–Kilodalton Protein of *Borrelia burgdorferi*", a Target for Bactericidial Human Monoclonal Antibodies, Infection and Immunity, Oct. 1993, vol. 61, No. 10, pp. 4523–4526.

Sigal et al., New England Journal of Medicine, 1998, vol. 339, No. 4, pp. 216–222.

Steere et al., New England Journal of Medicine, 1998, vol. 339, No. 4, pp. 209–215.

Telford et al., "Efficacy of human lyse disease vaccine formulations in a mouse model", J. Infect. Dis. 171, 1995, pp. 1368–1370.

Adam T, Gassmann GS, Rasiah C, Göbel UB. 1991. Phenotypic and genotypic analysis of *Borrelia burgdorferi* isolates from various sources. Infection and Immunity, 59: 2579–2585.

Adelmamn et al. 1983. DNA, 2: 183.

Anderson JF, Magnarelli LA, McAnich JB. 1988. Journal of Clinical Mirobiology, 26: 2209–2212.

(List continued on next page.)

Primary Examiner—Mark Navarro
Assistant Examiner—Jana Hines
(74) Attorney, Agent, or Firm—Frommer Lawrence & Haug, LLP; William S. Frommer; Thomas J. Kowalski

(57) ABSTRACT

The present invention relates to nucleic acid molecules, polypeptides encoded by the same, antibodies directed thereto and a method of preparing such polypeptides including: (a) inserting an isolated DNA molecule coding for a polypeptide which is immunoreactive with a 66 kDa polypeptide derived from *Borrelia garinii* IP90 into an expression vector; (b) transforming a host organism or cell with the vector; (c) culturing the transformed host cell under suitable conditions; and (d) harvesting the polypeptide. The isolated DNA molecule is preferably at least 10 nucleotides in length, and the method may optionally include subjecting the polypeptide to post-translational modification. The host cell can be a bacterium, a yeast, a protozoan, or a cell derived from a multicellular organism such as a fungus, an insect cell, a plant cell, or a mammalian cell.

43 Claims, 5 Drawing Sheets

OTHER PUBLICATIONS

Figures 3A, 3B:
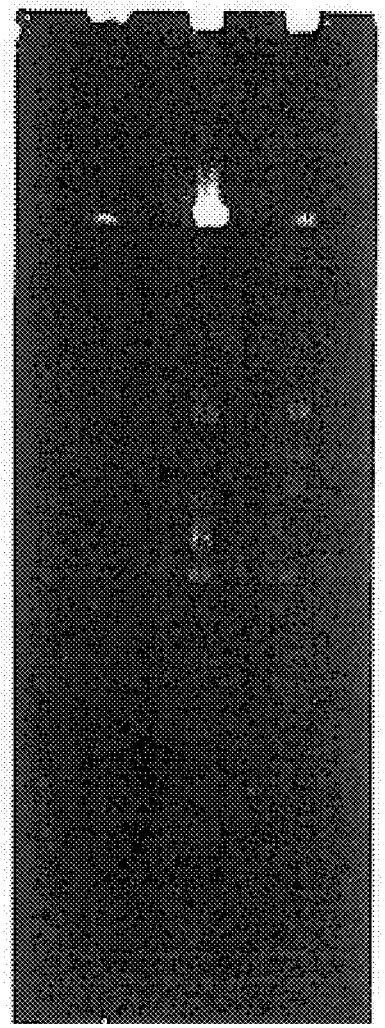

Arimitsu Y, Takashima I, Yoshii Z, Higashi Y, Kameyama S, Mizuguchi J. 1991. Journal of Infectious Diseases, 163: 682–683.

Baranton G, Postic D, Saint Girons I, Boerlin P, Piffaretti J–C, Assous M, Grimont PAD. 1992. Delineation of *Borrelia burgdorferi* sensu stricto, *Borrelia garinii* sp. nov., and group VS461 associated with *Lyme borreliosis*. International Journal of Systematic Bacteriology, 42: 378–383.

Barbour AG, Burdgorfer W, Grunwaldt E, Steere AC. 1983. Antibodies of patients with Lyme disease to components of the *Ixodes damini* spirochete. Journal of Clinical Investigation, 72: 504–515.

Barbour AG, Tessier SL, Hayes SF. 1984. Variation in a major surface protein of Lyme disease spirochetes. Infection and Immunity, 45: 94–100.

Barbour AG. 1984. Immunochemical analysis of Lyme disease spirochetes. The Yale Journal of Biology and Medicine, 57: 581–586.

Barbour AG. 1986. Polymorphisms of major surface proteins of *Borrelia burgdorferi*. Zbl Bakt Hyg, 263: 83–91.

Barbour AG. 1988. Journal of Clinical Microbiology, 26: 475–478.

Barthold SW, Bockenstedt LK. 1993. Passive immunizing activity of sera from mice infected with *Borrelia burgdorferi*. Infection and Immunity, 61: 4696–4702.

Beaucage SL, Caruthers MM et al. 1981. Tetrahedron Letters, 22: 1859–1862.

Bergström S, Sjöstedt A. Dotevall L. Kaijser B, Ekstrand–Eammarström B, Wallberg C, Skogman G, Barbour AG. 1991. Diagnosis of *Lyme borreliosis* by an enzyme immunoassay detecting immunglobulin G reactive to purified *Borrelia burdgorferi* cell components. European Journal of Clinical Microbiology and Infecticus Diseases, 10: 422–427.

Bolivar et al. 1977. Gene. 2(2):95–113.

Brucebauer HR, Preac–Mursic V, Fuchs R, Wilske B. 1992. Cross reactive proteins of *Borrelia burgdorferi*. European Journal of Infectious Diseases, 3: 224–232.

Burgdorfer W, Barbour AG, Hayes SF, Benach JL. Grunwaldt E, Davis JP. 1983 Lyme disease– a tick borne spirochetosis? Science, 216: 1317–1319.

Burman N, Bergström S, Restrepo BI, Barbour AG. 1990. The variable antigens Vmp7 and Vmp21 of the relapsing fever bacterium *Borrelia hermsii* are structurally analogous to the VSG proteins of the African trypanosome. Molecular Microbiology, 4: 1715–1726.

Canica MM, Nato F, duMerle L, Mazie JC, Baranton G, Postic D. 1993. Monoclonal antibodies for identification of *Borrelia afzelii* sp. nov. associated with late cutaneous manifestations of *Lyme borreliosis*. Scandinavian Journal of Infectious Diseases, 25: 441–448.

Chang et al. 1978. Nature, 375: 515.

Coleman JL, Benach JL. 1987. Isolation of antigenic components from the Lyme disease spirochete: their role in early diagnosis. Journal of Infectious Diseases, 155: 756–765.

Craft JE, Grodzicki RL, Steere AC. 1984. Journal of Infectious Diseases, 149: 789–795.

Crea et al. 1978. Proceeding of the National Academy of Sciences USA, 75: 5765.

Dressler F, Whalen JA, Reinhardt BN, Steere AC. 1993. Western blotting in the serodiagnosis of Lyme disease. The Journal of Infectious Diseases, 167: 392–400.

Eichenlaub R. 1979. Journal of Bacteriology, 138: 559–566.

Erdile LF, Brandt M–M, Warakomski DJ, Westrack GJ, Sadziene A, Barbour AG, Mays JP. 1933. Role of attached lipid in immunogenicity of *Borrelia burgdorferi* OspA. Infection and Immunity, 61: 81–90.

Ferdows MS, Barbour AG. 1989. Megabase–sized linear DNA in the bacterium *Borrelia burgdorferi*, the Lyme disease agent. Proceedings of National Academy of Science, 86: 5969–5973.

Fiers et al. 1978. Nature, 273: 113.

Fikrig E, Barthold SW, Marcantonio N. DePonte K, Kantor FS, Flavell RA. 1992. Roles of OspA, OspB, and flagellin in protective immunity to *Lyme borreliosis* in laboratory mice. Infection and Immunity, 60: 657–661.

Fikrig E, Barthold SW, Persing DE, Sun X, Kantor FS, Flavell RA. 1992. *Borrelia burgdorferi* strain 25015: characterization of cuter surface protein A and vaccination against infection. Journal of Immunology, 148: 2256–2260.

Gassmann GS, Jacobs E, Deutzmann R. Göbel UE. 1991. Analysis of fla gene of *Borrelia burgdorferi* GeHo and antigenic characterization of its gene product. Journal of Bacteriology, 173: 1452–1459.

Godman JL, Jarkovich P, Kramber JM, Johnson RC. 1991. Infection and Immunity, 59: 269–278.

Goeddel et al. 1979. Nature, 281:544.

Grodzicki RL, Steere AC. 1988. Comparison of immunoblotting and indirect enzyme–linked immunosorbent assay using different antigen preparations for diagnosing early Lyme disease. Journal of Infectious Diseases, 157: 790–797.

Hess et al. 1968. Journal of Advanced Enzyme Regulation, 7: 149.

Hitzeman et al. 1980. Journal of Biological Chemistry, 255: 2073.

Holland et al. 1978. Biochemistry, 17: 4900.

Hopp TP, Woods KR. 1981. Proceedings of the National Academy of Science USA, 78: 3824–3828.

Itakura et al. 1977. Science, 198: 1056.

Jameson BA, Wolf H. 1988. Computer Application in the biosciences, 4: 181–186.

Jones. 1977. Genetics, 84: 12.

Jonsson M, Noppa L, Barbour AG, Bergström S. 1992B. Heterogeneity of outer membrane proteins in *Borrelia burgdorferi*: comparison on Bsp operons of three isolates of different geographic origins. Infection and Immunity, 60: 1845–1853.

Kimgsman et al. 1979. Gene, 7: 141.

Kryuchechnikov VN, Korenberg EI, Scherbakov SV, Kovalevsky YV, Levin ML. 1988. Identification of Borrelia isolated in the USSR from *Ixodes persulcatus* schulze ticks. Journal of Microbiology, Epidemiology and Immunobiology, 12: 41–44.

Kyte J. Doolittle RF. 1982. Journal of Molecular Biology, 157: 105–132.

Laemmli UK. 1970. Nature 227: 680–685.

Lebech AM, Hindersson P, Vuust J, Hansen KJ. 1991. Journal of Clinical Microbiology, 29: 731–737.

Luft BJ, Jiang, W, Munoz P, Dattwyler RJ Gorevic PD. 1989. Biochemical and immunological characterization of the surface proteins of *Borrelia burgdorferi*. Infection and Immunity, 57: 3637–3645.

Luft BJ, Goveric PD, Jiang W, Munoz P, Dattwyler RJ. 1991. Immunologic and structural characterization of the dominant 66–to73–kDa antigens of *Borrelia burgdorfero*. Journal of Immunology, 146: 2776–2782.

Ma B, Christen B, Leung D, Vigo–Pelfrey C. 1992. Serodiagnosis of *Lyme borreliosis* by Western immunblot: reactivity of various significant antibodies against *Borrelia burgdorferi*. Journal of Clinical Microbiology, 30: 370–376.

Magnarelli LA., Anderson JF, BarbourAG. 1989. Enzyme–linked immunosorbent assays for Lyme disease: reactivity of subunits of *Borrelia burgdorferi*. Cross–reactivity in serologic tests for Lyme disease and other spirochetal infections. Journal of Infectious Diseases, 159: 43–49.

Magnarelli LA., Anderson JF, Johnson RC. 1987. Cross–reactivity in serologic tests for Lyme disease and other spirochetal infections. Journal of Infectious Disease, 156: 183–188.

Magnarelli LA., Miller JN, Anderson JF, Riviere GR. 1990. Cross–reactivity of nonspecific treponemal antibody in serologic tests for Lyme disease. Journal of Clinical Microbiology 28: 1276–1279.

Marconi RT, Garon CF. 1992. Phylogenetic analysis of the genus Borrelia: a comparison of North American and European isolates of *Borrelia burgdorferi*. Journal of Bacteriology, 174: 241–244.

Marconi RT, Konkel ME, Garon CF. 1993. Variability of osp genes and gene products among species of Lyme disease spirochetes. Infection and Immunity, 61: 2611–2617.

Marconi RT, Samuels DS, Schwan TG, Garon CF. 1993. Identification of a protein in several Borrelia species which is related to OspC of Lyme disease spirochetes. Journal of Clinical Microbiology, 31: 2577–2583.

*Messing et al. 1981. Third Cleveland Symposium on Macromolecules and Recombinant DNA, Ed. A Walton, Elsevier, Amsterdam.

Nielsen P E et al., 1991, Science 254: 1497–1500.

Norris SJ, Carter CJ, Howell JK, Barbour AG. 1992. Low-–passage–associated proteins of *Borrelia burgdorferi* B31: Characterization and molecular cloning of OspD, a surface exposed, plasmid–encoded lipoprotein. Infection and Immunity, 60: 4662–4672.

Norton Hughes CA, Engstrom SM, Coleman LA, Kodner CB, Johnson RC. 1993. Protective immunity is induced by a *Borrelia burgdorferi* mutant that lacks OspA and OspB. Infection and Immunity, 61: 5115–5122.

OlséB, Jaenson TGT, Noppa L, Bunikis J, Bergström S. 1993. A *Lyme borreliosis* cycle in seabirds and *Ixodes uriae* ticks. Nature, 362: 340–342.

Preac–Mursic V, Wilske B, Patsouris E, Jauris S, Will G, Soutschek E, Reinhardt S, Lehnert G, Klockmann U, Mehraein P. 1992. Active immunization with pC protein of *Borrelia burdgorferi* protects Gerbils against *Borrelia burgdorferi* infection. Infection, 20: 342–349.

Rahn DW, Malawista SE. 1991. Annals of Internal Medicine, 144: 472–481.

Raoult D, Eechemy KE, Baranton G. 1989. Crossreaction with *Borrelia burgdorferi* antigen of sera from patients with human immunodeficiency virus infection, syphilis, and leptospirosis. Journal of Clinical Microbiology, 27: 2152–2155.

Rosa PA, Schwan TG. 1989. Journal of infectious diseases, 160: 1018–1029.

Sadziene A, Thompson PA, Barbour AG. 1993. In vitro inhibition of *Borrelia burgdorferi* growth by antibodies. Journal of Infectious Diseases, 167: 165–172.

*Sambrook J. Fritsch EF, Maniatis T. 1989. Molecular cloning: a laboratory manual, 2nd ed. Cold Spring Harbor Laboratory, Cold Spring Harbor, N.Y..

Schmid GP. 1985. Reviews of infectious diseases, 7: 41–49.

Shanafelt MC, Hinderson P, Soderberg C, Mensi N. Turck CW, Webb D, Yasel H. Peltz G. 1991. Journal of Immunology, 146: 3985–3992.

Siebwenlist et al. 1980. Cell, 20: 269.

Simon MM, Schaible UE, Wallich R, Kramer MD. 1991. A mouse model for *Borrelia burgdorferi* infection: approach to a vaccine against Lyme disease. Immunology Today, 12: 11–16.

Simpson WJ, Schrumpf ME, Schwan TG. 1990. Reactivity of human *Lyme borreliosis* sera with a 39–kilodalton antigen specific to *Borrelia burgdorferi*. Journal of Clinical Microbiology, 28: 1329–1337.

Steere AC, Malawista SE, Syndman DR. 1977. Arthritis and rheumatism, 20: 7–17.

Steere AC, Taylor E, Wilson ML, Levine JF, Spielman A. 1986. Journal of Infectious Diseases, 154: 295–300.

Steere AC. 1989. Lyme disease. New England Journal of Medicine, 321: 586:596.

Stinchomb et al. 1979. Nature 282: 39.

Theisen M, Frederiksen B, Lebech A–M, Vuust J, Hansen K. 1993. Polymorphism in ospC gene of *Borrelia burgdorferi* and immunoreactivity of OspC protein: implications for taxomony and for use of OspC protein as a diagnostic antigen. Journal of Clinical Microbiology, 31: 2570–2576.

Tschemper et al. 1980. Gene, 10: 157.

Ulmer JB et al. 1993. Curr. Opin. Invest. Drugs, 2: 983:989.

Wallich R, Moter SE, Simon MM, Ebnet K, Eeiberger A, Kramer MD. 1990. Infection and Immunity, 58: 1711–1719.

Wilske B, Preac–Mursic V, Jauris S, Hofman A, Pradel I, Soutschek E, Schwab E, Will G, Wanner G. 1993. Immunological and molecular polymorphisms of OspC, an immunodominant major outer surface protein of *Borrelia borgdorferi*. Infection and Immunity, 61: 2182–2191.

Wilske B, Preac–Mursic V, Schierz G, Busch KV. 1986. Immunochemical and immunological analysis of European *Borrelia burgdorferi* strains. Zbl Bakt Hyg, 263: 92–102.

Zingg BC, Anderson JF, Johnson RC, LeFebvre RB. 1993. Comparative analysis of genetic variability among *Borrelia burgdorferi* isloates from Europe and the United States by restriction enzyme analysis, gene restriction fragment length polymorphism, and pulse–field gel electrophoresis. Journal of Clinical Microbiology, 31: 3115–3122; and.

Asbrink E, Hovmark A, Hederstedt B. 1984. The spirochetal etiology of acrodermatitis chronica atrophicans Herxheimer. Acta Dermatologica et Venereologica, 64: 506–512.

Luft et al. Journal of Immunology 146 (8): 2776–82, 1991.

Kantor, Fred. Scientific American 271(3): 34–9, Sep. 1994.

Sadziene et al. Journal of Infectious Diseases 167:165–72, 1993.

Nguyen et al. Infection and Immunity 62(5): 2079–84, 1994 (May).

* cited by examiner

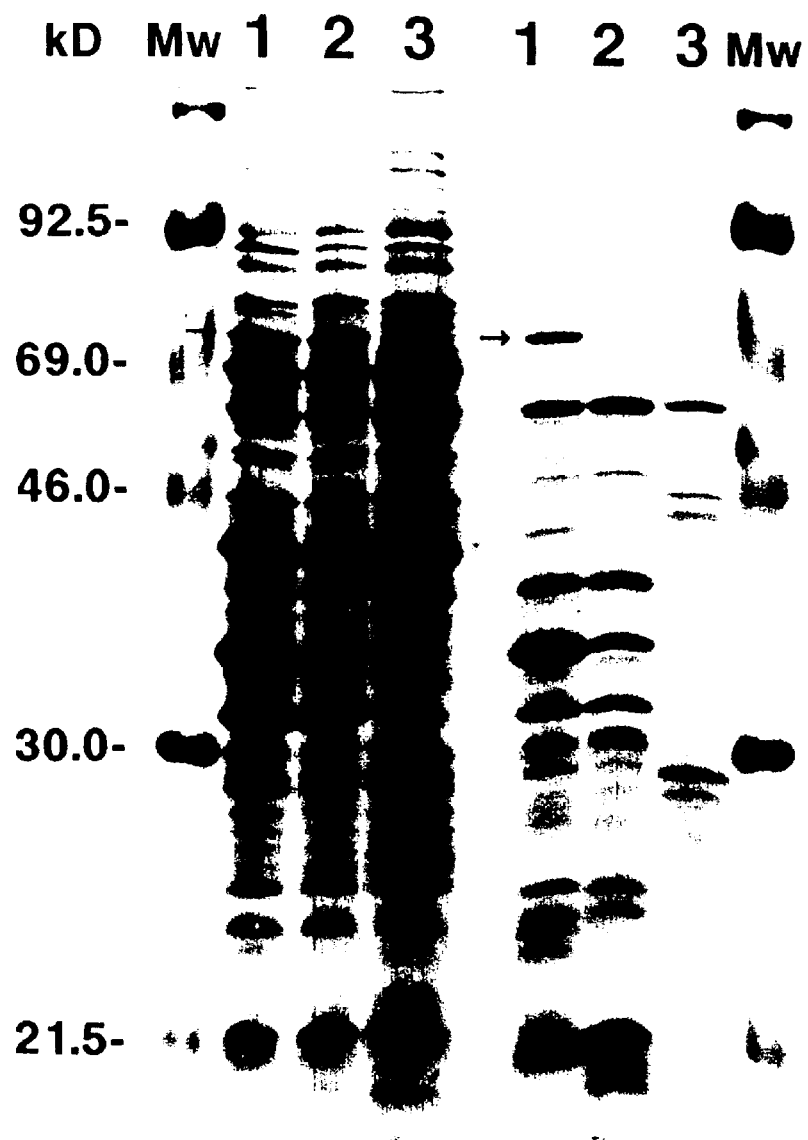

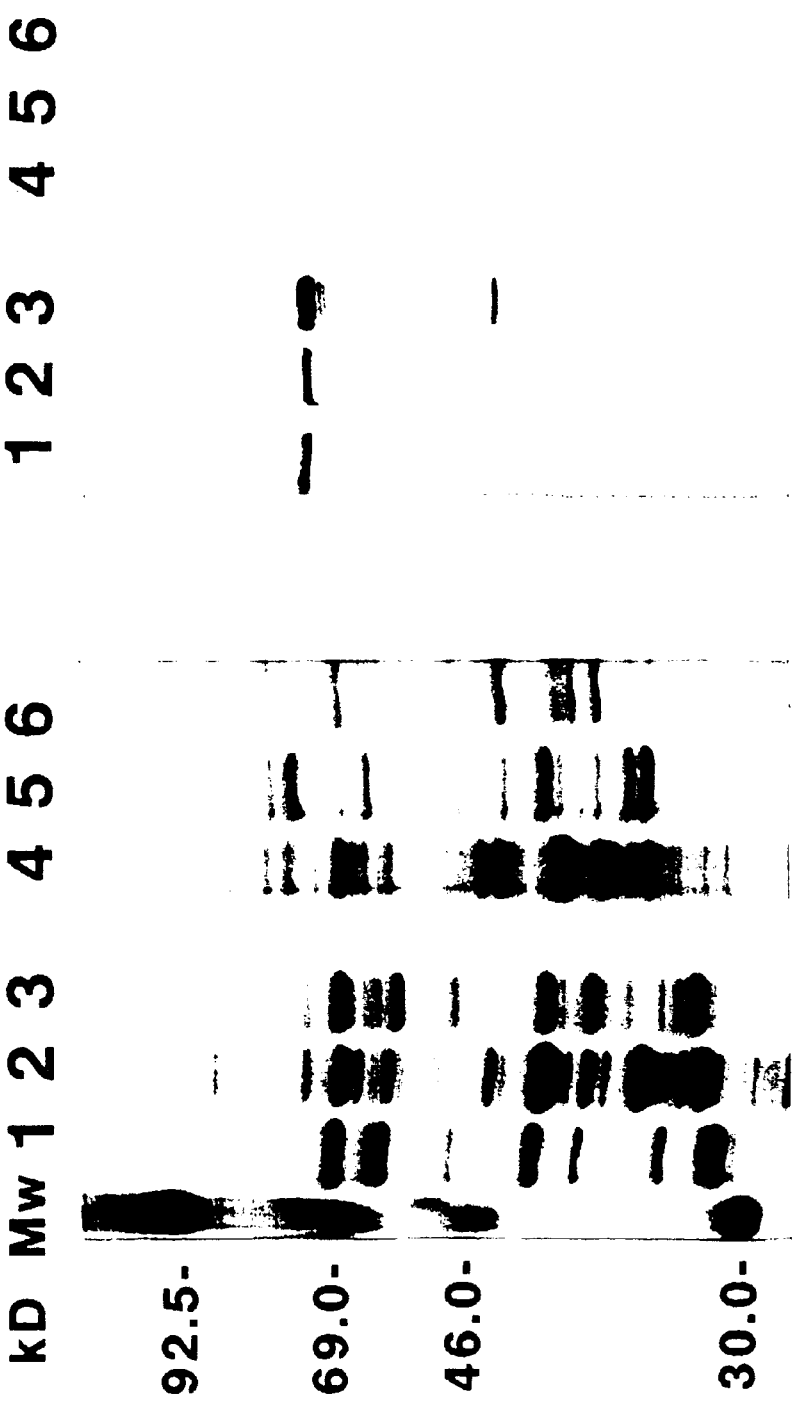

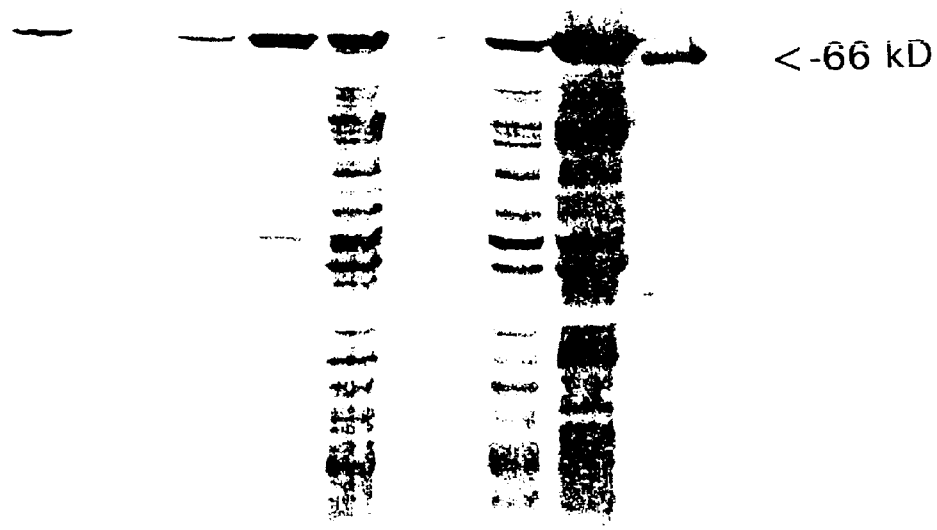

66 KDA ANTIGEN FROM BORRELIA

CROSS-REFERENCE TO RELATED APPLICATIONS

The present application is a divisional of U.S. application Ser. No. 08/262,220 filed Jun. 20, 1994, now U.S. Pat. No. 6,054,296 which is a continuation-in-part of U.S. application Ser. No. 08/079,601, filed Jun. 22, 1993, now U.S. Pat. No. 5,523,089, which is a continuation of U.S. application Ser. No. 07/924,798, filed Aug. 6, 1992, now abandoned, which is a continuation of U.S. application Ser. No. 07/422,881, filed Oct. 18, 1989, now abandoned, which claims priority from Danish application Serial No. 5902/88, filed Oct. 24, 1988.

FIELD OF THE INVENTION

The present invention relates to nucleic acid fragments encoding antigenic proteins associated with *Borrelia burgdorferi* sensu lato (*Borrelia burgdorferi* sensu stricto, *Borrelia garinii*, and *Borrelia afzelii*, denoted Bb herein), particularly polypeptides associated with virulence of the bacteria. The invention also relates to methods for producing Bb immunogenic polypeptides and corresponding antibodies. Other embodiments of the invention relates to compositions and methods for detecting Lyme disease and also vaccines against infections with *Borrelia burgdorferi* sensu lato are a part of the invention as is methods of immunizing animals against diseases caused by these infections. Vectors and transformed cells comprising Bb associated nucleic acids are also included.

DESCRIPTION OF RELATED ART

Lyme disease is a multisystem disease resulting from tick transmission of the infectious agent, Bb (Rahn and Malawista, 1991). Although recognized as a clinical entity within the last few decades data back to the early part of the 20th century. Cases of the disease have been reported in Europe, Asia and North America (Schmid, 1985). Despite a relatively low total incidence compared to other infectious diseases, Lyme disease represents a significant health problem because of its potentially severe cardiovascular, neurologic and arthritic complications, difficulty in diagnosis and treatment and high prevalence in some geographic regions.

Bb is not a homogenous group but has a variable genetic content, which may in turn affect its virulence, pattern of pathogenesis and immunogenicity. Lyme borreliosis associated borreliae are so far taxonomically placed into three species, *Borrelia burgdorferi* sensu stricto, *Borrelia garinii*, and *Borrelia afzelii* (Burgdorfer et al. 1983, Baranton et al. 1992, Canica et al. 1993). It is well documented that considerable genetic, antigenic and immunogenic heterogeneity occurs among them, as well as among the strains within the separate species (Baranton et al. 1992, Canica et al. 1993, Zingg et al. 1993, Wilske et al. 1993, Adam et al. 1991, Marconi and Garon 1992). The major evidence of this phenomenon is provided by the molecular studies of the plasmid encoded outer surface protein A (OspA), B (OspB), and C (OspC) (Barbour et al. 1984, Jonsson et al. 1992, Wilske et al. 1993, Marconi et al. 1993). In different animal models efficient protection is achieved by passive and active immunization with OspA (Simon et al., 1991 Fikrig et al., 1992, Erdile et al., 1993), therefore, OspA remains one of the main candidates for Borrelia vaccine. It is unclear, however, whether inter and intra-species heterogeneity of OspA, as well as other competitors for immunoprophylaxis, allow efficient cross-protection (Fikrig et al. 1992, Norris et al., 1992). Furthermore, it was recently suggested that certain protective antibodies produced early in the course of Borrelia infection is unrelated to OspA (Norton Hughes et at., 1993, Barthold and Bockenstedt, 1993).

Its virulence factors, pathogenetic mechanisms and means of immune evasion are unknown. At the level of patient care, diagnosis of the disease is complicated by its varied clinical presentation and the lack of practical, standardized diagnostic tests of high sensitivity and specificity. Antimicrobial therapy is not always effective, particularly in the later stages of the disease.

Variation among Bb strains and species and the changes resulting from in vitro passage add to the problems of developing vaccines or immunodiagnostics from either the whole organism or specifically associated proteins. Using a PCR assay, it was found that one set of oligonucleotide primers was specific for North American Bb isolates, another for most European isolates and a third set recognized all Bb strains (Rosa et al., 1989).

Serological assays for the diagnosis and detection of Lyme disease are thought to offer the most promise for sensitive and specific diagnosis. However, serologic assays generally use whole Bb as antigen and suffer from a low "signal to noise" ratio, i.e, a low degree of reactivity in positive samples, particularly early in the disease, as compared to negative samples. This problem results in high numbers of false negatives and the potential for false positives. Background reactivity in negative controls may be due in part to conserved antigens such as the 41K flagellin and the 60K "Common Antigen". These Bb proteins possess a high degree of sequence homology with similar proteins found in other bacterial. Therefore normal individuals will often express anti-flagellar and anti-60K antibodies. Unique, highly reactive Bb antigens for serological assays are therefore desirable but heretofore unavailable.

Diagnosis of Lyme disease remains a complex and uncertain endeavour, due to lack of any single diagnostic tool that is both sensitive and specific. Clinical manifestations and history are the most common bases for diagnosis. However, there is a pressing need for specific, sensitive, reproducible and readily available confirmatory tests. Direct detection offers proof of infection but is hampered by the extremely low levels of Bb that are typically present during infection, as well as the inacessibility of sites that tend to be consistently positive (e.g., heart and bladder). Culture, although sensitive, is cumbersome and requires 1–3 weeks to obtain a positive result. PCR appears to offer promise in terms of direct detection (Lebech et al., 1991) and indeed Goodman et al (1991) have reported detection of Bb DNA in the urine of patients with active Lyme disease using a PCR method. However, it is unlikely that PCR assays will become commonly used in clinical laboratories because of the degree of skill required for its use and the high risk of DNA contamination.

Another problem in detection of Lyme disease is the substantial number of humans exposed to Bb who develop unapparent or asymptomatic infections. This number has been estimated as high as 50% (Steere et al., 1986).

There is clearly a need for means of preparing Bb-specific antigens, e.g., for the development of diagnostic tests for Lyme disease or vaccines against Lyme disease. Adequate assays do not exist and should ideally meet several criteria, including (1) expression of an antigen by all pathogenic Bb strains, (2) elicitation of an immune response in all Lyme disease patients, (3) high immunogenicity with a detectable antibody response early in the infection stage, (4) antigens unique to Bb without cross reactivity to other antigens and, (5) distinction between individuals exposed to nonpathogenic as opposed to pathogenic forms of Bb.

Problems similar to those relating to diagnosis exist when attempting to prepare a vaccine against diseases caused by Bb. Successful single antigen vaccines have until now not been prepared, possibly due to the inter-strain and inter-species antigenic variation. As mentioned above, OspA has been the main candidate for the immunogenic constituent of a single antigen vaccine, but time has proven that in order for such a vaccine to be efficient it has to contain OspA from at least three different Bb species (*Borrelia burgdorferi* sensu stricto, *Borrelia garinii*, and *Borrelia afzelii*).

A number of investigators have reported the presence of proteins with molecular weights in the region between 60 and 75 kDa. Many of these proteins are also recognised by antibodies in patient sera when analyzed by Western blots. (Barbour 1984, Luft et al., 1989). Protease treatment of *Borrelia burgdorferi* cells (Barbour et al. 1984) showed that a minor protein with a apparent molecular weight of 66 kDa was accessible to proteolytic cleavage, and hence probably associated with the outer envelope. Coleman and Benach (1987) isolated a protein with apparent molecular weight of 66 kDa from an outer envelope fraction isolated from *Borrelia burgdorferi* B31. However, direct amino acid sequencing of Bb proteins with the apparent molecular weights 66-, 68-, 71-, and 73-kDa revealed these proteins to have high sequence similarity with the *E. coli* heat-shock proteins (Luft et al., 1991) making them less suitable for the use in prophylaxis and serodiagnosis.

SUMMARY OF THE INVENTION

The inventors have surprisingly found that an antigen from Bb with an apparent molecular weight of 66 kDa (determined by SDS-PAGE, and staining with Coomassie Blue) is highly conserved in the three strains *B. burgdorferi* sensu stricto B31, *B. garinii* IP90, and *B. afzelii* ACAI, whereas this antigen cannot be found in Borrelia species related to relapsing fever and avian borreliosis. The disclosed antigens therefore are excellent candidates for vaccines and diagnostics relating to infections with Bb.

Thus, the present invention addresses one or more of the foregoing or other problems associated with the preparation and use of Bb specific antigens, particularly those antigens which are associated with virulence and which are useful for developing detection and diagnostic methods for Lyme disease as well as vaccines against Lyme disease i.e., Borrelia antigens, OspA, OspB, OspC, OspD and PC. The invention involves the identification of such antigens, as well as the identification and isolation of Bb nucleic acid sequences that encode Bb antigens or antigenic polypeptides derived therefrom. These sequences are useful for preparing expression vectors for transforming host cells to produce recombinant antigenic polypeptides. It is further proposed that these antigens will be useful as vaccines or as immunodiagnostic agents for Bb associated diseases such as Lyme disease in particular.

The DNA disclosed herein was isolated from the bacteria *Borrelia burgdorferi* sensu lato hereafter designated as Bb. The microorganism is a spiral-shaped organism approximately 0.2 micron in diameter and ranging in length from about 10–30 microns. Like other spirochetes, it possesses an inner membrane, a thin peptidoglycan layer, an outer membrane, and periplasmic flagella which lie between the inner and outer membranes. Bb is obligate parasite found only in association with infected animals and arthropod vectors in endemic areas. Bb-like organisms have also been identified in birds raising the possibility that birds could also serve as an animal reservoir. While some Bb isolates have been cloned, most isolates have not been cloned and most likely represent mixtures of different variants even at the time of culture origination.

Bb has similarities with other relapsing fever organisms such as *B. hermsii*. B has a single chromosome with two unusual features, linear conformation and small size (approximately 900 kilobase pairs). Fresh isolates of Bb contain up to four linear plasmids and six circular supercoiled plasmids. The plasmid content of different Bb isolates is highly variable. For example, in one study only two of thirteen strains had similar plasmid profiles. Some plasmids are lost during in vitro passage which may correlate with loss of virulence, outer surface proteins OspA and OspB are encoded on the 49 kbp linear plasmid. The 66 kDa membrane-associated proteins discovered by the inventors are encoded on the Bb chromosome.

In order to identify DNA segments encoding the 66 kDa proteins, purified protein was isolated from *B. afzelii* ACAI, by preparative SDS-PAGE for subsequent use in amino acid sequencing. The peptide was transferred to polyvinylene diffusable membranes, sequence analysis was performed using standard sequencing techniques (Matsudaira, 1987). An 8 amino acid sequence was identified (SEQ ID NO: 1). Codons for the amino acid sequence were selected by reverse translation based on (1) conclusion that codons containing A or T were favoured and (2) knowledge of published DNA sequences for several Bb proteins. A choice favouring A or T containing codons was based on the observation that the G+C content of Bb is only 28–35% (Burman et al. 1990). A 24 nucleotide segment was synthesized having the structure in SEQ ID NO: 2 (corresponding to amino acids 6–13):

5'-GAA AAA GAT ATW TTT AAA ATW AAT-3' wherein W denotes the bases A or T, i.e. the 24 nucleotide segment exists in 4 variants.

DNA libraries were prepared by restriction enzyme digestion of DNA prepared from *B. Burgdorferi* B31, *B. afzelii* ACAI and *B. garinii* IP90.

The 24 residue oligonucleotide probe was used as a probe to screen the DNA library prepared from *B. garinii* IP90 to identify DNA encoding the 66 kDa protein isolated from this Bb species.

A 592 bp DNA fragment coding for part of the 66 kDa protein from *B. garinii* Ip90 was used as a probe to screen DNA libraries prepared from *B. burgdorferi* B31 and *B. afzelii* ACAI to identify DNA encoding the 66 kDa protein from these Bb species.

Antigenicity of the 66 kDa protein was determined. Antiserum collected from rabbits injected with the 66 kDa protein prepared from *B. garinii* Ip90 was shown to react with the 66 kDa proteins, as detected on immunoblots of *B. garinii* Ip90 as well as *B. burgdorferi* B31 and *B. afzelii* ACAI. No reactive spots were detected in normal rabbit serum. This result should lead to straightforward production of monoclonal antibodies reactive with the 66 kDa polypeptides from one strain of one species exclusively as well as from two or all three species. Antibodies could be produced and used for screening strains for protein expression, for determining structural location and for examining bactericidal activity of antibodies against these proteins.

The nucleic acid segments of the present invention thus encode amino acid sequences associated with Bb. Some of these amino acid sequences are antigenic. The nucleic acid sequences are also important for their ability to selectively hybridize with complementary stretches of Bb gene segments.

Varying conditions of hybridization may be desired, depending on the application envisioned and the selectivity of the probe toward the target sequence. Where a high degree of selectivity is desired, one may employ relatively stringent conditions to form the hybrids, such as relatively low salt and/or high temperature conditions. Under these conditions, little mismatch between the probe and template or target strand is tolerated. Less stringent conditions might be employed where, for example, one desires to prepare mutants or to detect mutants when significant divergence exists.

In clinical diagnostic embodiments, nucleic acid segments of the present invention may be used in combination with an appropriate means, such as a label, to determine hybridization with DNA of a pathogenic organism. Typical methods of detection might utilize, for example, radioactive species, enzyme-active or other marker ligands such as avidin/biotin, which are detectable directly or indirectly. In preferred diagnostic embodiments, one will likely desire to employ an enzyme tag such as alkaline phosphatase or peroxidase rather than radioactive or other reagents that may have undesirable environmental effects. Enzyme tags, for example, often utilize colorimetric indicator substrates that are readily detectable spectrophotometrically, many in the visible wavelength range. Luminescent substrates could also be used for increased sensitivity.

Hybridizable DNA segments may include any of a number of segments of the disclosed DNA. For example, relatively short segments including 12 or so base pairs may be employed, or, more preferably when probes are desired, longer segments including 20, 30 or 40 base pairs, depending on the particular applications desired. Shorter segments are preferred as primers in such applications as PCR, while some of the longer segments are generally preferably for blot hybridizations. It should be pointed out, however, that while sequences disclosed for the DNA segments of the present invention are defined by SEQ ID NO: 3, SEQ ID NO: 5 and SEQ ID NO: 7 and SEQ ID NO: 13, a certain amount of variation or base substitution would be expected, e.g., as may be found in mutants or strain variants, but which do not significantly affect hybridization characteristics. Such variations, including base modifications occurring naturally or otherwise, are intended to be included within the scope of the present invention.

While the 66 kDa Bb antigen has been disclosed in terms of specific amino acid sequences from three strains of Bb, it is nonetheless contemplated that the amino acid sequence will be found to vary even further from species to species and isolate to isolate. Moreover, it is quite clear that changes may be made in the underlying amino acid sequence through e.g., site-directed mutagenesis of the DNA coding sequence, in a way that will not negate its antigenic capability.

The invention also relates to at least partially purified antigenic Bb proteins or polypeptides capable of eliciting an in vivo immunogenic response in animals which are later challenged with Bb. These proteins may comprise all or part of the amino acid sequence encoded by the herein disclosed DNA. Particularly preferred antigenic proteins have the amino acid sequence shown in SEQ ID NO: 4, SEQ ID NO: 6, SEQ ID NO: 8, and SEQ ID NO: 14. These proteins, as well as their epitopes, will be useful in connection with vaccine development, and as antigen(s) in immunoassays for detection of Bb antibodies in biological fluids such as serum, seminal of vaginal fluids, urine, saliva, body exudates and the like.

In other aspects, the invention concerns recombinant vectors such as plasmids, phage or viruses, which comprise DNA segments in accordance with the invention, for use in replicating such sequences or even for the expression of encoded antigenic peptides or proteins. Vectors or plasmids may be used to transform a selected host cell. In preparing a suitable vector for transforming a cell, desired DNA segments from any of several Bb sources may be used, including genomic fragments, cDNA or synthetic DNA. In practice of the present invention, an expression vector may incorporate at least part of the DNA sequence of SEQ ID NO: 3, SEQ ID NO: 5, SEQ ID NO: 7, and SEQ ID NO: 13 encoding one or more epitopic segments of the disclosed 66 kDA antigens.

Expression vectors may be constructed to include any of the DNA segments disclosed herein. Such DNA might encode an antigenic protein specific for virulent strains of Bb or even hybridization probes for detecting Bb nucleic acids in samples. Longer or shorter DNA segments could be used, depending on the antigens protein desired. Epitopic regions of the 66 kDa proteins expressed or encoded by the disclosed DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cells.

Recombinant vectors such as those described are particularly preferred for transforming bacterial host cells. Accordingly, a method is disclosed for preparing transformed bacterial host cells that includes generally the steps of selecting a suitable bacterial host cell, preparing a vector containing a desired DNA segment and transforming the selected bacterial host cell. Several types of bacterial host cells may be employed, including Bb, *E. coli, B. subtilis,* and the like as well as prokaryotic host cells.

Transformed cells may be selected using various techniques. including screening by differential hybridization, identification of fused reporter gene products, resistance markers, anti-antigen antibodies and the like. After identification of an appropriate clone, it may be selected and cultivated under conditions appropriate to the circumstances, as for example, conditions favouring expression or, when DNA is desired, replication conditions.

Another aspect of the invention involves the preparation of antibodies and vaccines from the antigenic 66 kDa proteins or epitopic regions of that protein encoded by the disclosed DNA. The invention thus relates to one or more antibodies, monoclonal or polyclonal, that may be generated in response to the 66 kDa Bb proteins or their epitopes. It is expected that the sensitivity and specificity of antibody response to this 66 kDa proteins and their epitopes will be superior to the response that has been obtained from other Bb antigens that are not associated with virulence. Previous work with several Bb antigens low sensitivity when immunofluorescence and ELISA assays were employed, especially during early stages of infection.

In both immunodiagnosis and vaccine preparation, it is often possible and indeed more practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jame-son-Wolf or Kyte-Doolittle antigenicity analyses or Hopp and Woods (1981) hydrophobicity analysis (see, e.g., Jameson and Wolf, 1988; Kyte and Doolittle, 1982; or U.S. Pat. No. 4,554,101). Hydrophobicity analysis assigns average hydrophilicity values to each amino acid residue from these values average hydrophilicities can be calculated and regions of greatest hydrophilicity determined. Using one or more of these methods, regions of predicted antigenicity may be derived from the amino acid sequence assigned to the 66 kDa polypeptide. Regions from the 66 kDa antigens having a high likelihood of being epitopes include the sequences corresponding to positions 175–190, 285–305, 365–385, and 465–490.

It is contemplated that the antigens and immunogens of the invention will be useful in providing the basis for one or more assays to detect antibodies against Bb. Previous assays have used whole Bb as the antigen. Sera from normal individuals not exposed to Bb often contain antibodies that react with Bb antigens, in particular antigens that have epitopes in common with other bacteria. It is necessary to adjust assay conditions or the diagnostic threshold of reactivity to avoid false positive reactions due to these cross-reactive antibodies in normal sera. These adjustments may in turn decrease the sensitivity of the assay and lead to false negative reactions, particularly in the early stage of Bb infection. Assays using the disclosed 66 kDa proteins of antigenic polypeptides thereof, are expected to give superior results both in sensitivity and selectivity when compared to assays that use whole Bb or even purified flagella in either an indirect ELISA or an antibody capture ELISA format. Western immunoblots based on reactions with such antigens (whole Bb. flagella and the like) have been difficult to interpret due to the presence of antibodies in sera from unexposed individuals. These antibodies cross react with Bb antigens, most particularly the 41 kDa flagellin and the 60 kDa common antigen protein. Generally, assays which use whole epitopes that will cross react with other bacterial antigens. For example, the N and C terminal regions of the Bb flagellin possess 52–55% sequence identity with the Salmonella typhimurium and *Bacillus subtilis* sequences (Wallich et al., 1990), exemplifying the highly conserved nature of flagellin structure. The 60 kDa Bb protein is likewise 58 homologous with the *E. coli* protein (Shanafelt et al., 1991). Such cross reactivity is not likely with the 66 kDa antigen, which is apparently unique to Bb.

It is further anticipated that a recombinant derived 66 kDa Bb protein will be particularly preferred for detecting Bb infections. Unexposed individuals should have a low reactivity to one or more epitopes of the 66 kDa proteins thereby making it possible to use lower dilutions of serum and increase sensitivity. Using a combination of more than one of these unique antigens may also enhance sensitivity without sacrificing specificity.

Preferred immunoassays are contemplated as including various types of enzyme linked immunoassays (ELISAS), immunoblot techniques, and the like, known in the art. However, it readily appreciated that utility is not limited to such assays, and useful embodiments include RIAs and other nonenzyme linked antibody binding assays or procedures.

Yet another aspect of the invention is a method of detecting Bb nucleic acid in a sample. The presence of Bb nucleic acid in the sample may be indicated by the presence of the polypeptide products which it encodes. The method therefore includes detecting the presence of at least a portion of any of the polypeptides herein disclosed. Suitable detection methods include, for example, immunodetection reagents, PCR amplification, and hybridization.

Yet another aspect of the invention includes one or more primers capable of priming amplification of the disclosed DNA of SEQ ID NO: 3, SEQ ID NO: 5, SEQ ID NO: 7, and SEQ ID NO: 13. Such primers are readily generated taking into account the base sequence of the DNA segment of SEQ ID NO: 3, SEQ ID NO: 5, SEQ ID NO: 7, and SEQ ID NO: 13, the disclosed DNA, or deriving a base sequence from the amino acid sequence of a purified polypeptide encoded by the DNA. Primers are analogous to hybridization probes, but are generally relatively short DNA segments, usually about 7–20 nucleotides.

Methods of diagnosing Lyme disease are also included in the invention. In one embodiment, an antibody-based method includes obtaining a sample from a patient suspected of having Lyme disease, exposing that sample to one or more epitopes of the Bb protein which is encoded by the DNA disclosed and finally determining a reactivity of the antibody with one or more epitopes of a Bb protein that may be in the sample. The reactivity measured is indicative of the presence of Lyme disease. Typical samples obtainable from a patient include human serum, plasma, whole blood, cerebrospinal fluid, seminal or vaginal fluids, exudates and the like.

Several variations of antibody-based methods are contemplated for development; for example, an indirect ELISA using the 66 kDa proteins or other Bb proteins as an antigen. The 66 kDa proteins may be produced in large quantities by recombinant DNA vectors already disclosed and purified. Optimal concentration of the antigen could be determined by checker board titration and diagnostic potential of the 66 kDa proteins assay examined further by testing serum from mice at different stages of infection and infected with different strains of Bb. These results could indicate the relative time course for sera conversion for each of the assays and would also show whether infection with different strains causes variation in anti-66 kDa protein titers.

Likewise, reactive epitopes of the 66 kDa polypeptides are contemplated as useful either as antigens in an ELISA assay or to inhibit the reaction of antibodies toward intact 60 kDa proteins bound to a well. Epitopic peptides could be generated by recombinant DNA techniques previously disclosed or by synthesis of peptides from individual amino acids. In either case, reaction with a given peptide would indicate presence of antibodies directed against more epitopes. In addition to its diagnostic potential, this method is seen as being particularly effective in characterizing monoclonal antibodies against the 66 kDa proteins and other virulence associated proteins.

In further aspects, the present invention concerns a kit for the detection of Bb antigens, the kit including, alternatively, an antibody reactive with 66 kDa antigenic proteins or protein or peptide which includes an epitope thereof, together with means for detecting a specific immunoreaction between an antibody and its corresponding antigen. Examples of suitable means include labels attached directly to the antigen or antibody, a secondary antibody having specificity for human Ig, or protein A or protein G. Alternatively, avidin-biotin mediated *Staphylococcus aureus* binding could be used. For example, the monoclonal antibody may be biotinylated so as to react with avidin complexed with an enzyme or fluorescent compound.

A particular kit embodiment of the invention concerns detection of antibodies against the described Bb 66 kDa antigens, epitopes thereof as represented by portions of the amino acid sequences, or closely related proteins or peptides, such as epitopes associated with other virulence-associated proteins detected by comparison of low-passage, virulent and high-passage, a virulent strains of Bb. The antigen for the kit (s) consists of the Bb 66 kDa proteins or portions thereof produced by a recombinant DNA vector in *E. coli* or another bacterial or nonbacterial host. Alternatively, the antigen may be purified directly from Bb or manufactured as a synthetic peptide. Samples for the assays may be body fluids or other tissue samples from humans or animals. The presence of reactive antibodies in the samples may be demonstrated by antibody binding to antigen followed by detection of the antibody-antigen complex by any of a number of methods, including ELISA, RIA, fluorescence, agglutination of precipitation reactions, nephelometry, or any of these assays using avidin-biotin reactions. The degree of reactivity may be assessed by comparison to control samples, and the degree of reactivity used as a measure of present or past infection with Bb. The assay(s) could also be used to monitor reactivity during the course of Lyme disease, e.g., to determine the efficacy of therapy.

In still further embodiments, the invention contemplates a kit for the detection of Bb nucleic acids in the sample, wherein the kit includes one or more nucleic acid probes specific for the 66 kDa genes, together with means for detecting a specific hybridization between such a probe and Bb nucleic acid, such as an associated label.

DETAILED DESCRIPTION OF THE PREFERRED EMBODIMENT

Hence, the invention relates to an isolated nucleic acid fragment comprising a nucleotide sequence which encodes a polypeptide exhibiting a substantial immunological reactivity with a rabbit antiserum raised against a 66 kDa polypeptide derived from *Borrelia garinii* IP90, said rabbit antiserum exhibiting substantially no immunological reactivity with whole cell preparations (prepared as described herein) from at least 95% of randomly selected *Borrelia hermsii, Borrelia crocidurae, Borrelia anserina,* or *Borrelia hispanica.*

By the term "nucleic acid fragment" as used herein is meant a fragment of DNA or RNA, but also of PNA (of Nielsen P E et al., 1991) having a length of at least two joined nucleotides. It will be understood, that although the disclosed nucleic acid fragments of the present invention are DNA fragments, it may be desirable to employ a RNA fragment in e.g. a viral vector, the genome of which is natively composed of RNA. for the purposes of preparing e.g. probes for hybridization assays as described below, PNA fragments may prove useful, as these artificial nucleic acids have been demonstrated to exhibit very dynamic hybridization properties.

The term "a substantial immunological reactivity" is meant to designate a marked immunological binding between an antibody/antiserum on the one hand, and on the other an antigen, under well-defined conditions with respect to physicochemical parameters as well as concentrations of antigens and antibodies. Thus, a substantial immunological reactivity should be clearly distinguishable from a non-specific interaction between an antibody/antiserum and an antigen: This distinction can for instance be made by reacting the antibody/antiserum with a known concentration of an antigen which has previously been shown not to react with the antibody/antiserum, and then using this reaction as a negative control. A positive control could suitably be the reaction between the antibody/antiserum and the same concentrations of the antigen used for the immunisation resulting in the production of the antibody/antiserum. In such an assay, an antigen resulting in a relative signal of at least 10% (calculated as $S_m \cdot (S_p \cdot S_n) \cdot 100$, where $S_m$ is the measured signal, $S_p$ the positive control signal, an $S_n$ the negative control signal) is regarded as having a substantial immunological reactivity. An antigen exhibiting "substantially no immunological reactivity" therefore is defined as an antigen giving a signal of at the most 10%.

Although the data presented herein demonstrates that there is no cross-reactivity between antigens from *Borrelia hermsii, Borrelia crocidurae, Borrelia anserina,* or *Borrelia hispanica* and the disclosed polypeptides, it is conceivable that a few isolates of these bacteria will exhibit some cross-reactivity. As can be deduced from the above it is expected that the cross-reactivity will be less than 5% (since there is no reactivity with at least 95% of randomly chosen *Borrelia hermsii, Borrelia crocidurae, Borrelia anserina,* or *Borrelia hispanica*), and according to the invention this cross-reactivity may be even lower, such as at the most 4% and 3%, preferably at the most 2%, such as 1%. According to the invention the cross-reactivity is most preferred at most ½%, such as 0%. In such a case there will be no substantial immunological reactivity between the rabbit antiserum mentioned above and whole cell preparations of *Borrelia hermsii, Borrelia crocidurae, Borrelia anserina,* or *Borrelia hispanica.*

The above-cited considerations concerning cross-reactivity apply for all cross-reactions between on the one hand the polypeptides/DNA fragments of the invention and on the other hand material from *Borrelia hermsii, Borrelia crocidurae, Borrelia anserina,* and *Borrelia hispanica.*

When using the term "cross-reactivity" is herein meant the phenomenon that two species exhibit a common feature which is detected in a reaction. In the present context the term cross-reactivity is used for similar reactions in antigen-antibody interactions as well as in hybridization interactions.

Nucleic acid fragments of the invention useful as hybridisation probes and/or primers are not necessarily those fragments encoding immunologically useful polypeptides. Therefore the invention also relates to nucleic acid fragments which hybridises readily with either a DNA fragment having the nucleotide sequence SEQ ID NO: 3, SEQ ID NO: 5, SEQ ID NO: 7, or SEQ ID NO: 13 or with a DNA fragment complementary thereto, but exhibits no substantial hybridization with genomic DNA from at least 95% of randomly selected *Borrelia hermsii, Borrelia crocidurae, Borrelia anserina,* or *Borrelia hispanica* when the hybridization conditions are highly stringent.

Preferred nucleic acids of the invention are DNA fragments, especially those which have nucleotide sequences with a sequence homology of at least 70% with SEQ ID NO: 3, SEQ ID NO: 5, SEQ ID NO: 7, or SEQ ID NO: 13 or subsequences there of. However, the degree of homology may be even higher such as at least 75%, 80%, 85%, 87%, and 89%. It is preferred that the degree of homology is at least 90%, such as 92%, 94% or 95%, and especially preferred are DNA fragments with a sequence homology of at least 96% with SEQ ID NO: 3, SEQ ID NO: 5, SEQ ID NO: 7, or SEQ ID NO: 13. Especially for high accuracy hybridization assays, a total homology is necessary, and therefore preferred.

The terms "homology" and "homologous" are, with respect to DNA fragments, intended to mean a homology between the nucleotides in question in between which the homology is to be established, in the match with respect to identity and position of the nucleotides of the DNA fragments. With respect to polypeptides and fragments thereof described herein, the terms and intended to mean a homology between the amino acids in question between which the homology is to be established, in the match with respect to identity and position of the amino acids of the polypeptides.

Considerations similar to those given above for the immunological reactivity and cross-reactivity of antigens can be applied for the distinction between a nucleic acid fragment which "hybridizes readily" and a fragment which "exhibits substantially no hybridization" under high stringency conditions.

The term "highly stringent" when used a conjunction with hybridisation conditions is as defined in the art that is 5–10° C. under the melting point $T_m$, cf. Sambrook et al, 1989, pages 11.45–11.49.

Interesting nucleic acid fragments of the invention encodes a polypeptide comprising an amino acid sequence comprised in a polypeptide present in whole cell preparations of *Borrelia burgdorferi* B31, *Borrelia garinii* IP90, and/or *Borrelia afzelii* ACAI but substantially absent from whole cell preparations of at least 95% of randomly selected *Borrelia hermsii*, *Borrelia crocidurae*, *Borrelia anserina*, or *Borrelia hispancia*. This encoded polypeptide may according to the invention comprise at least a part of an amino acid sequence of a 66 kDa protein which is present in Bb, and it is preferred that the polypeptide encoded by the nucleic acid fragment of the invention is a 66 kDa protein present in whole cell preparations, and preferably this 66 kDa protein is also present in fraction B (as discussed in the examples). It is especially preferred that the encoded polypeptide further is a natively surface exposed protein of *Borrelia burgdorferi* B31, *Borrelia garinii* IP90, or *Borrelia afzelii* ACAI.

By the terms "present" and "substantially absent", when referring to amino acid sequences and polypeptides in bacteria, are meant that the concentration of the amino acid sequence/polypeptide in a bacterium where it is "present" is at least 100 times higher than in a bacterium where it is substantially absent. However, it is preferred that the ratio of the concentrations are at least 1000, and more preferred at least 10,000, 100,000 or even higher. It is especially preferred that there can be observed no concentration of the amino acid sequence/polypeptide in the bacterium from where it is substantially/absent.

It will be understood from the above that various analogues and subsequences of the nucleic acids disclosed herein are interesting aspects of the invention, as are nucleic acid fragments encoding fused polypeptides including polypeptides encoded by nucleic acid fragments of the invention.

The term "analogue" with regard to the nucleic acid fragments of the invention is intended to indicate a nucleotide sequence which encodes a polypeptide identical or substantially identical to a polypeptide encoded by a nucleic acid fragment of the invention (SEQ ID NOs: 4, 6, 8 and 14).

It is well known that the same amino acid may be encoded by various codons, the codon usage being related, inter alia, to the preference of the organisms in question expressing the nucleotide sequence. Thus, one or more nucleotides or codons of a nucleic acid fragment of the invention may be exchanged by others which, when expressed, result in a polypeptide identical or substantially identical to the polypeptide encoded by the nucleic acid fragment in question.

Also, the term "analogue" is used in the present context to indicate a nucleic acid fragment or a nucleic acid sequence of a similar nucleotide composition or sequence as the nucleic acid sequence encoding the amino acid sequence having the immunological properties discussed above, allowing for minor variations which do not have an adverse effect on the biological function and/or immunogenicity as compared to the disclosed polypeptides, or which give interesting and useful novel binding properties or biological functions and immunogenicities etc. of the analogue. The analogous nucleic acid fragment or nucleic acid sequence may be derived from an animal or a human or may be partially or completely of synthetic origin as described herein. The analogue may also be derived through the use of recombination nucleic acid techniques.

Furthermore, the terms "analogue" and "subsequence" are intended to allow for variations in the sequence such as substitution, insertion (including introns), addition, deletion and rearrangement of one or more nucleotides, which variations do not have any substantial effect on the polypeptide encoded by a nucleic acid fragment of a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence point within it, and "re-arrangement" is intended to mean that two or more nucleotide residues have been exchanged with each other.

A preferred method of preparing variants of the 66 kDa antigens disclosed herein is site-directed mutagenesis. This technique is useful in the preparation of individual peptides, or biologically functional equivalent proteins or peptides, derived from the 66 kDa antigen sequences, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the techniques typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-directed mutagensis in accordance herewith is performed by first obtaining a single-stranded vector which includes within its sequence a DNA sequence which encodes the 66 kDa antigens. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which includes recombinant vectors bearing the mutated sequence arrangement.

The preparation of sequence variants of the selected 66 kDa genes using site-directed mutagenesis is provided as a means of producing potentially useful species of the 66 kDa genes and is not means to be limiting as there are other ways in which sequence variants of the 66 kDa genes may be obtained. For example, recombinant vectors encoding the desired 66 kDa genes may be treated with mutagenic agents to obtain sequence variants (see, e.g., a method described by Eichenlaub, 1979) for the mutagensis of plasmid DNA using hydroxylamine.

Analogues/subsequences of the disclosed nucleic acid fragments which also form part of the invention are nucleic acid fragments which are fused to at least one other nucleic acid fragment which encodes a protein enhancing the immunogenicity of the fused protein relative to a protein without the encoded fusion partner. Such encoded proteins may e.g. be lipoproteins, e.g. the outer membrane lipoprotein from *E. coli* and OspA from *Borrelia burgdorferi* sensu lato; viral proteins, e.g. from Hepatitis B surface antigen, Hepatitis B core antigen, and the influenta virus non-structural protein NS1; immunoglobulin binding proteins, e.g. protein A, protein G, and the synthetic ZZ-peptide; T-cell epitopes; or B-cell epitopes.

Other nucleic acid fragments to form part of a nucleic acid fragment of the invention encoding a fusion polypeptide are those encoding polypeptides which facilitates expression and/or purification of the fused peptide. Such encoded polypeptides could according to the invention be bacterial fimbrial proteins e.g. the pilus components pilin and papA; protein A; the ZZ-peptide; the maltose binding protein; gluthatione S-transferase; β-galactosidase; or polyhistidine.

Other nucleic acid fragments of the invention of special interest are those encoding at least one epitope present in whole cell preparations of *Borrelia burgdorferi* B31, *Borrelia garinii* IP90, or *Borrelia afzeli* ACAI but substantially absent from whole cell preparations of at least 95% of randomly selected *Borrelia hermsii, Borrelia crocidurae, Borrelia anserina,* and *Borrelia hispanica.* Preferred are epitopes a of a 66 kDa protein present in whole cell preparations of Bb.

By the term "epitope" is meant the spatial part of an antigen responsible for the specific binding to the antigen-binding part of an antibody. It goes without saying that the identification of epitopes of the disclosed antigens will facilitate the production of polypeptides exhibiting marked antigenicity thus making them interesting with respect to diagnosis of Borreliosis and vaccination against infections with Bb.

The identification of epitopes can be performed in several ways. One possibility is to make a hydrophobicity plot as described herein, and thereafter selecting the special linear sequences of the polypeptides and investigate their immunogenicity. As mentioned herein, several regions of the disclosed polypeptides are regarded as interesting. Thus, nucleic acids encoding polypeptides substantially identical to the amino acid sequences 175–190, 285–305, 365–385, or 465–490 in SEQ ID NO: 3, SEQ ID NO: 5, SEQ ID NO: 7, or SEQ ID NO: 13 also form part of the invention; such nucleic acid fragments may also be part of nucleic acid fragments encoding fusion polypeptides comprising multiple copies of at least one of epitope, as such fusion polypeptides should exhibit superior immunological utility in diagnostics as well as in vaccines.

Another way of simply identifying epitopes is to digest a polypeptide antigen with a known amino acid sequence with endo- and exopeptidases. The obtained fragments are tested against antibodies directed against the whole polypeptide, and by way of deduction, the precise location of the linear epitopes can be determined. A variation of this method involves the recombinant production of subfragments (cf. the above) of the full-length polypeptide followed by the same test procedure.

Another part of the invention relates to a substantially pure polypeptide exhibiting a substantial immunological reactivity with an antiserum from rabbits immunised with a 66 kDa polypeptide derived from *Borrelia garinii* IP90, said rabbit antiserum exhibiting substantially no immunological reactivity with whole cell preparations from at least 95% of randomly selected *B. hermsii, B. crocidurae, B. anserina,* or *B. hispanica.*

It will be understood that such a polypeptide may be encoded by a DNA fragment of the invention and that the polypeptides encoded by the DNA fragemtns of the invention also form part of the invention.

By the term "polypeptide" is herein understood a molecule comprising at least two amino acids joined by a peptide bond. The term polypeptide thus indicate small peptides (less than 10 amino acid residues), oligopeptides (between 10 and 100 amino acid residues), proteins (the functional entity including at least one peptide and/or prosthetic groups and/or glycosylation and/or lipidation etc.) as well as traditional polypeptides (more than 100 amino acid residues).

Interesting polypeptides according to the invention are those prepared by the well known methods of liquid or solid phase peptide synthesis utilizing the successive coupling of the individual amino acids of the polypeptide sequence. Alternatively, the polypeptide can be synthesized by the coupling of individual amino acids forming fragments of the polypeptide sequence which are later coupled so as to result in the desired polypeptide. These methods thus also constitute another interesting part of the invention.

Preferred polypeptides of the invention are recombinant polypeptides, normally prepared by a process comprising

- inserting a nucleic acid fragment of the invention in an expression vector,
- transforming a host organism of a host cell (normally a host organism or host cell which does not natively express the polypeptide of the invention) with the vector,
- culturing the transformed host cell under conditions facilitating the expression of the polypeptide by the host organism or host cell,
- harvesting the polypeptide, and optionally subjecting the polypeptide to post-translational modification(s), and
- performing an at least partial purification of the polypeptide.

The need for post-translational modifications exists because certain polypeptides are prepared in the above-described manner lacking for instance a fatty-acylation of an amino acid residue, or the polypeptide have for some reason been prepared in an elongated version which should be cleaved before the polypeptide will prove functional. Thus, according to the invention the post-translational modifications involves lipidation, glycosylation, cleavage, or elongation of the polypeptide. In some instances, the host cell or cell line also processes the translation product so as to obtain a processed polypeptide.

The present invention thus also relates to the use of the nucleic acid fragments of the invention in the construction of vectors and in host cells. The following is a general discussion relating to such use and the particular considerations in practising this aspect of the invention.

In general, of course, prokaryotes are preferred for the initial cloning of nucleic sequences of the invention and constructing the vectors useful in the invention. For example, in addition to the particular strains mentioned in the more specific disclosure below, one may mention by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F-, lambda-, prototrophic, ATCC No. 273325), bacilli such as *Bacillus subtilis,* or other enterobacteriaceae such as *Salmonella typhimurium* or *Serratia marcesans,* and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used. *Saccharomyces cerevisiase,* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

In the light of the above discussion the methods for recombinantly producing the polypeptide of the invention are also a part of the invention, as are the vectors carrying and/or being capable of replicating the nucleic acids according to the invention in a host cell or a cell-line. According to the invention the expression vector can be e.g. a plasmid, a cosmid, a minichromosome, or a phage. Especially interesting are vectors which are integrated in the host cell/cell line genome after introduction in the host.

Another part of the invention are transformed cells (useful in the above-described methods) carrying and capable of replicating the nucleic acid fragments of the invention; the host cell can be a microorganism such as a bacterium, a yeast, or a protozoan, or a cell derived from a multicellular organism such as a fungus, an insect cell, a plant cell, or a mammalian cell. Especially interesting are cells from the bacterial species Escherichia, Bacillus and Salmonella, and a preferred bacterium is *E. coli.*

Yet another part of the invention relates to a stable cell line producing a polypeptide according to the invention, and preferably the cell line carries and expresses a nucleic acid of the invention.

Returning to the polypeptides of the invention: Also polypeptides which comprises an amino acid sequence exhibiting a sequence homology of at least 50% with SEQ ID NO: 4, SEQ ID NO: 6, SEQ ID NO: 8, SEQ ID NO: 10, or SEQ ID NO: 14 or subsequences thereof. However this homology should normally be higher, such as at least 60%, 70%, 80%, 85%, or even 90%. Preferred polypeptides have a homology of at least 92%, such as at least 95%, 97%, 98%, 99%, or even 100%.

A very important part of the invention is vaccines for conferring increased resistance to infection with Bb.

Thus, an important part of the invention relates to vaccines comprising an amount of the polypeptide according to the invention, the amount of the polypeptide being effective to confer substantially increased resistance to infections with *Borrelia burgdorferi* sensu lato in an animal, including a human being, optionally in combination with a pharmaceutically acceptable carrier or vehicle and the vaccine optionally further comprising an adjuvant. Of course, also vaccines comprising polypeptide fragments encoded by the nucleic acid fragments of the invention are a part of the invention, as such polypeptide fragments as mentioned above also form part of the invention.

By the term "conferring substantially increased resistance to infections" is meant that the administration of the vaccine to the animal has the effect that disease caused by infections with at least one strain of bacteria is avoided or at least that the risk of catching the disease is significantly reduced.

Part of the present invention contemplates vaccine preparation and use. General concepts related to methods of preparation and use are discussed in the following as applicable to preparations and formulations with the polypeptides of the invention.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions of suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgement of the practitioner. However, suitable dosage ranges are of the order of several hundred micrograms active ingredient per vaccination with a preferred range from about 1 $\mu$g to 500 $\mu$g, especially in the range from about 10 $\mu$g to 50 $\mu$g. Suitable regimes for intitial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine include use of agents such as aluminum hydroxide or phosphate (alum), commonly used as 0.05 to 0.1 percent solution in phosphate buffered saline, admisture with synthetic polymers of sugars (Carbopol) used as 0.25 percent solution, aggregation of the protein in the vaccine by heat treatment with temperatures ranging betwen 70° to 101° C. for 30 second to 2 minute periods respectively. Aggregation by reactivating with pepsin treated (Fab) antibodies to albumin, mixture with bacterial cells such as C. parvum or endotoxins or lipopolysaccharide components of gramnegative bacteria, emulsion in physiologically acceptable oil vehicles such as mannide monooleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain levels of the antibodies. The course of the immunization may be followed by assays for antibodies for the supernatant antigens. The assays may be performed by labelling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

It is contemplated that the vaccines of the invention should be effective in activating both arms of the immune system. Thus, vaccines capable of eliciting a cell-mediated immune reaction are also a part of the invention.

One such vaccine of the invention is a live vaccine comprising a non-pathogenic miroorganism carrying and being capable of expressing a nucleic acid fragment of the invention, the live vaccine being effective in conferring increased resistance to infection with *Borrelia burgdorferi* sensu lato in an animal, including a human being. The non-pathogenic microorganism could for instance be a bacterium such as a strain of *Mycobacterium bovis* BCG. The live vaccine could for instance express a multitude of the polypeptides of the invention, thereby making it more immunogenic.

Another way of eliciting a cell-mediated response is to employ an adjuvant as described above. However, recent research have revealed a new an exciting possibility, wherein a DNA fragment is introduced into non-replicating cells of the vaccinated animal, whereafter the translational product is exposed on the cell-surface thereby eliciting a cell-mediated response. These methods are reviewed in Ulmer et al., 1993, which hereby is included by reference.

Therefore, also a part of the invention is a vaccine comprising a nucleic acid fragment according to the invention, the vaccine effecting in vivo expression of antigens by an animal, including a human being, to whom the vaccine has been administered, the amount of expressed antigens being effective to confer substantially increased resistance to infections with *Borrelia burgdorferi* sensu lato in an animal, including a human being.

It is also possible that a vaccine according to the invention comprising other Borrelia antigens may prove useful, as a more efficient immunological response could be elicited. Such a combination vaccine could for instance contain OspA, OspB, OspC, OspD, and/or PC, other Borrelia antigens which may be employed in such a vaccine composition. In this regard, also combination vaccines comprising at least two different polypeptides i.e., two non-identical polypeptides, according to the invention are interesting.

Methods of actively immunizing animals, including mammals such as human beings against infections with Bb are also parts of the invention. The methods generally consists the administration to the animal of an immunogenically effective amount of the vaccines of the invention. Methods for passive immunisation comprising administering to the animal an immunogenically effective amount of an antibody of the invention (as described below) is also included in the invention.

An important part of the invention relates to at least partially purified antibodies, polyclonal or monoclonal, reacting substantially specifically with a protein according to the invention, or proteins encoded by the nucleic acid fragments of the invention. According to the invention, monoclonal antibodies are preferred.

The phrase "reacting substantially specifically" is intended to indicate that the antibody will show no substantial immunological reactivity (as defined above) with other antigens which might possibly be present in an embodiment of the present invention where the antibody is used.

The antibodies of the invention are prepared by methods well-known to the skilled person.

Other important parts of the present invention are compositions adapted for the determination of Bb in animals (including mammals, e.g. humans). Accordingly, methods of determining the presence of Bb are also a part of the invention.

A diagnostic composition adapted for the determination of *Borrelia burgdorferi* sensu lato in an animal, including a human being, or in a sample, the composition comprising an amount of the polypeptide of the invention effective to detectably react with antibodies present in the animal or in the sample, the antibodies being directed against *Borrelia burgdorferi* sensu lato, the composition optionally comprising a detectable label, is also a part of the invention. Similar compositions including the nucleic acid fragments of the invention or the antibodies of the invention are also a part of the invention, as will be apparent from the claims.

The phrase "to detectably react with" is intended to mean a reaction between to substances in an assay, the reaction being significant enough so as to give a signal in the assay which is clearly different from a negative signal. Thus, the detectable reaction is highly dependent on the type of detection means used. Very sensitive methods like ELISAs and RIAs will detect reactions involving few molecules, whereas more insensitive reactions will demand that the reaction involves many molecules.

Methods of determining the presence of Bb antibodies or components of Bb in samples or in animals are also parts of the invention, as a method of determining the presence of antibodies directed against *Borrelia burgdorferi* sensu lato in an animal, including a human being, or in a sample, comprising administering the polypeptide of the invention to the animal or incubating the sample with the polypeptide of the invention, and detecting the presence of bound antibody resulting from the administration or incubation. Likewise, a method of determining the presence of a *Borrelia burgdorferi* sensu lato antigen in an animal, including a human being, or in a sample, comprising administering an antibody of the invention to the animal or incubating the sample with the antibody, and detecting the presence of bound antigen resulting from the administration or incubation, forms part of the invention. Finally a method of determining the presence of *Borrelia burgdorferi* sensu lato nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridized nucleic acids resulting from the incubation, is also included in the invention.

Finally, diagnostic kits for the diagnosis of on-going or previous Bb infection forms part of the invention. The diagnostic kits of the invention comprises an antibody, a nucleic acid, or a polypeptide according to the invention in combination with a means for detecting the interation with the relevant substance reacting with these substances of the invention; the choice of these detection means is discussed elsewhere herein.

In both the diagnostic methods, compositions, and kits the antibodies, nucleic acids or polypeptides according to the invention may optionally be coupled to solid or semi-solid carriers, as is well-known in the art.

As will appear from the examples, the present invention relates to the utility of Bb associated antigenic proteins as diagnostic or preventive tools in Lyme disease. Proteins have been identified as associated only with virulent isolates of Bb, providing a basis for several types of diagnostic tests for infections with Bb and for Lyme disease, including immunodiagnostic and nucleic acid identification, such as those based on amplification procedures (PCR etc.).

It is contemplated that several assays for the presence of Bb or for Lyme disease may be developed using any of the polypeptides of the invention, the corresponding nucleic acid fragments encoding the protein, functionally similar proteins and their epitopes, or by detection of other appropriate nucleic acids. These methods are similar in principle to those previously described (Magnarelli et al., 1989; Magnarelli et al., 1984; and Craft et al., 1984). Reactive epitopes representing portions of the 66 kDa protein sequences could be utilized in an analogous manner.

Another promising assay is the microcapsule agglutination technique (MCAT) (Arimitsu et al., 1991). In this procedure, microscopic polystyrene beads are coated with Bb antigen and incubated with dilutions of patient serum. After overnight incubation at 4° C., the agglutination patterns are determined. Using whole Bb as antigen, the MCAT has been shown to be highly discriminatory between Lyme disease patients and healthy individuals, with little ovrlap in agglutination titer, although false positive reactions have been obtained with rheumatoid arthritis patients (Anderson et al., 1988) and leptospirosis samples (Barbour, 1988). An assay using 66 kDa protein alone or in combination with other antigens such as the 94 kDA, 30 kDa and 21 kDa antigens should be feasible. Such combination may increase sensitivity of the assay.

Also contemplated within the scope of the present invention is the use of the disclosed nucleic acid fragments as hybridization probes. While particular examples are provided to illustrate such use, the following provides general background for hybridization applications taking advantage of the disclosed nucleic acid sequences of the invention.

The invention has disclosed a DNA segment encoding an antigenic Bb protein. Detection of that DNA or various parts thereof is expected to provide the basis for a useful assay. One method of detecting the 66 kDa antigen genes is based on selective amplification of known portions of the gene. A particular method utilizes PCR amplification, using any of a number of primers that could be prepared from knowledge of the nucleic acid sequence of SEQ ID NO: 3, SEQ ID NO: 5 and SEQ ID NO: 7, and SEQ ID NO: 13. Generally, such primers are relatively short, e.g., 7–28 base pairs in length, and may be derived from the respective sense or anti-sense strands of the disclosed DNA segment. Synthesis of these primers may utilize standard phosphoramidite chemistry (Beaucage et al., 1981).

As mentioned, in certain aspects, the DNA sequence information provided by the invention allows for the preparation of relatively short DNA (or RNA or PNA) sequences having the ability to specifically hybridize to Bb gene sequences. In these aspects, nucleic acid probes of an appropriate length are prepared based on a consideration of the sequence, e.g., SEQ ID NO: 3, SEQ ID NO: 5, SEQ ID NO: 7, and SEQ ID NO: 13 or derived from flanking regions of these genes. The ability of such nucleic acid probes to specifically hybridize to the Bb gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

To provide certain of the advantages in accordance with the invention, the preferred nucleic acid sequence employed for hybridization studies or assays includes sequences that are complementary to at least a 10 to 40, or so, nucleotide stretch of the selected sequence, such as that shown in SEQ ID NO: 3, SEQ ID NO: 5, SEQ ID NO: 7, and SEQ ID NO: 13. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

The present invention will find particular utility as the basis for diagnostic hybridization assays for detecting Bb-specific RNA or DNA in clinical samples. Exemplary clinical samples that can be used in the diagnosis of infections are thus any samples which could possibly include nucleic acid, including samples from tissue, blood serum, urine or the like. A variety of tissue hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of Bb gene segments. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15 M–0.9 M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In clinical diagnostic embodiments, nucleic acid sequenes of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as alkaline phosphatase or peroxidase, instead of radioactive or other environmentally undesirable reagents. In the case of enzyme tags, colorimetric indicator substrates are known which employed to provide a means visible to the human eye or spectrophotometrically, to identify specific hybridization with pathogen nucleic acid-containing samples. Luminescent substrates, which give off light upon enzymatic degradation, could also be employed and may provide increased sensitivity.

In general, it is envisioned that the hydridization probes described herein will be useful both as reagents in solution hybridization as well as in embodiments employing a solid phase. In embodiments involving a solid phase, the test DNA (or RNA) from suspected clinical samples, such as exudates, body fluids (e.g., amniotic fluid cerebrospinal fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, or example, on the G-C contents, type of target nucleic acid, source of nucleic acid, size of hybridization probe, etc.). Following washing of the hybridized surface so as to remove non-specifically bound probe molecules, specific hybridization is detected, or even quantified, by means of the label.

Plasmids pJB-101, pJB-102, and pJB-104 have been deposited at Deutsche Sammlung von Mikroorganismen und Zellkulturen GmbH under the terms and conditions of the Budapest Treaty on the Jun. 17, 1994

LEGENDS TO THE FIGURES

FIGS. 1A and 1B. Effect of proteases on *B. afzelii* ACAI cells. A: Coomassie blue-stained PAGE of the bacterial lysates after the cells were incubated with buffer alone, lane 1; trypsin, lane 2; or proteinase K, lane 3. B: PAGE of the subcellular fraction of membrane components (Fraction B) recovered from the cells treated in three different ways described in section A. Arrows indicate the position of 66 kDa protein. Mw: molecular weight, kD: kilodalton.

FIGS. 2A and 2B. Comparison of phenotypic expression of the 66 kDa protein in Borrelia species. A: Coomassie blue-stained PAGE of the whole cell proteins of *B. burgdorferi* B31, lane 1; *B. afzelii* ACAI, lane 2; *B garinii* Ip90, lane 3; *B. hermsii,* lane 4; *B. crocidurae,* lane 5; and *B. anserina,* lane 6. B: Reactivity of Borrelia proteins against rabbit anti-66 kDa protein antibody in Western blot. Borrelia species are numbered as in section A. Arrow indicates the position of the 66 kDa protein. Mw: molecular weight, kD: kilodalton.

FIGS. 3A and 3B. Southern blot analysis of DNA. A: DNA separated by pulse-field agarose gel electrophoresis. Lane 1, DNA prepared from *B. burgdorferi* B31. Lane 2, DNA prepared from *Borrelia afzelii* ACAI. Lane 3, DNA prepared from *Borrelia garinii* Ip90. B: DNA subsequently transferred to a Hybond-N membrane and cross-linked with UV-light and probed at 55° C. with a radiolabelled DNA probe derived by PCR amplification of the 66 kDa gene from *Borrelia garinii* Ip90. Lane 1, Lane 2 and Lane 3 same as above.

FIGS. 4A and 4B. Western blot analysis of recombinant 66 kDa protein expressed in *E. coli.* A: Proteins prepared from uninduced *E. coli.* B: Proteins prepared from induced *E. coli.* Proteins were separated by 12.5% SDS-PAGE and subsequently transferred to an Immobilon-P membrane by electroblotting. Non-specific binding was blocked by immersing the filter in 5% BSA. The proteins were visualised by using the rabbit anti-66 kDa serum as primary antibody and an alkaline phosphatase conjugated anti-rabbit IgG secondary antibody with a subsequent developing reaction using the substrate BCIP. Lane 1, proteins prepared from whole cells. Lane 2, proteins from the supernatant obtained after sonication. Lane 3, proteins obtained by extraction of the pellet after sonication with 2M urea. Lane 4, proteins obtained by further extraction of the pellet after sonication with 8M urea. Lane 5, fraction B prepared from *B. garinii* Ip90.

Figure 5A:
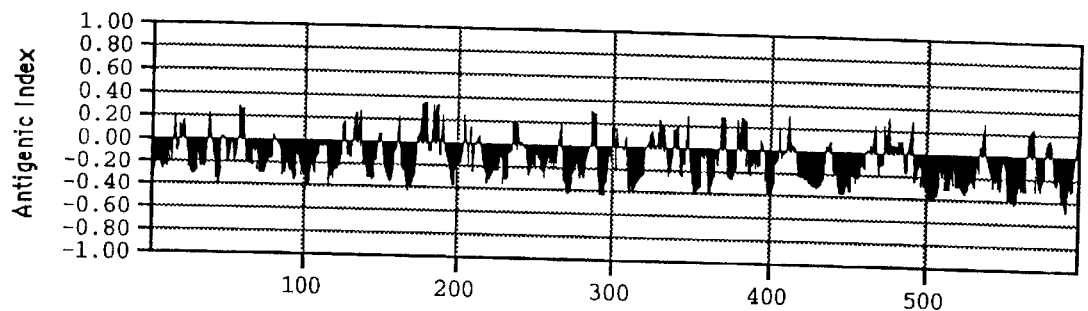
Figure 5B:
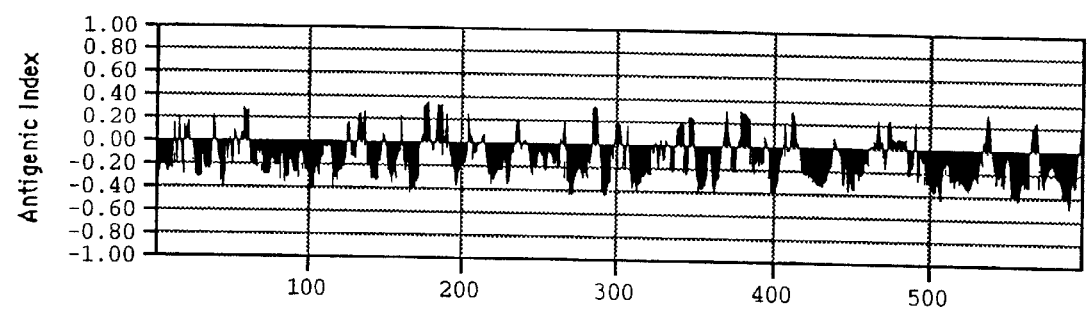
Figure 5C:
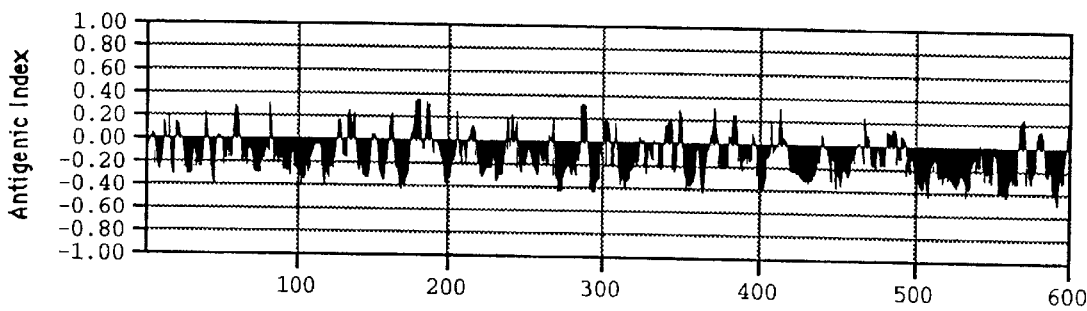

FIGS. 5A, 5B, and 5C. Plot of antigenicity index of the 66 kDa protein. The plots were made using the Jameson-Wolf algorithm provided in the MacVector software package. A: 66 kDa protein from *B. burgdorferi* B31. B: 66 kDa protein from *B. afzelii* ACAI. C: 66 kDa protein from *B. garinii* Ip90.

EXAMPLES

Bacterial strains and culture conditions. Borrelia strains used in this study were the following: strain B31 of *B. burgdorferi,* a tick isolate from North America (ATCC 35210); strain ACAI of *B. afzelii,* a human skin isolate from Sweden (Å sbrink et al. 1984); strain Ip90 of *B. garinii,* a tick isolate from the Asian Russia (Kryuchechnikov et al. 1988); strain *B. burgdorferi* B313, a mutant of *B. burgdorferi* B31 lacking OspA and OspB (Sadziene et al. 1993).

Also used were three relapsing fever borreliae species, *B. hermsii, B. crocidurae,* and *B. hispanica,* and *B. anserina,* the causative agent of avian borreliosis.

Borreliae were grown in BSK II medium (Barbour 1984) and the cells were harvested in late-log phase by centrifugation at 5,000 rpm for 20 min.

The *Escherichia coli* strains Dh5α and BL21 were used for transformation with the recombinant plasmids in, respectively, DNA cloning and gene expression experiments. *E. coli* strains were grown in Luria broth medium (Gibco BRL, Gaithersburg, Md.) supplemented, when required, with carbenicillin (Sigma, St. Louis, Mo.) at 50 μg/ml.

Example 1

Preparation of Borrelia proteins, sodium dodecyl sulphate-polyacrylamide gel electrophoresis (SDS-PAGE), and Western blot 1.1 Preparation of Borrelia Proteins For the whole-cell protein preparations, bacteria harvested from 200 ml of BSK II medium were washed twice with phosphate-buffered saline-5 mM $MgCl_2$, (PBS—Mg). The pellet was suspended in 2 ml of PBS, sonicated an the supernatant was collected after centrifugation at 10,000 rpm for 30 min. In some experiments whole-cell lysate was obtained by boiling washed bacteria for 3 min in SDS-PAGE sample buffer.

The subcellular fraction of borreliae outer membrane components (designated Fraction B) was prepared as described elsewhere (WO 90/04411). Briefly, cells harvested from 1.5 l of the culture were washed three times with 10 mM Tris-HCl (pH 7.4), 150 mM NaCl and 5 mM $MgCl_2$. (TSM buffer). Octyl-β-D-glycopyranoside (OGP) (Sigma St. Louis, Mo.) was added to a final concentration of 2% in 10 ml TSM buffer and the suspension was incubated at 37° C. for 60 min. The cell lysate was centrifuged and the supernatant was incubated at 56° C. for 30 min. The precipitate was removed by centrifugation at 20,000 rpm for 30 min at 37° C., and the supernatant was dialysed against water at 4° C. for 2 days. The precipitate (Fraction B) formed in the dialysis bag was recovered by centrifugation at 20,000 rpm for 30 min at 25° C.

1.2 Separation of Proteins by SDS-PAGE

Bacterial proteins were separated by 12.5% SDS-PAGE essentially according to Laemmli (1970). Subsequently, gels were either stained with Coomassie Blue R-250 (CB) (Sigma, St Louis, Mo.) or were subjected to Western blotting.

1.3 Western Blotting

The proteins were transferred to Immobilon-P membrane (Millipore, Bedford, Mass.) by electroblotting at 0.8 mA/cm$^2$ for 1 h. The nonspecific binding was blocked by immersing the filter for 2 h into 5% bovine serum albumin (BSA) (Sigma, St. Louis, Mo.) in PBS, containing 0.05% Tween-20 (PBS-T). Primary or secondary antibodies were diluted with 2.5% BSA in PBS-T, and both incubations of the filter for 1 h was followed by washing in PBS-T. In a developing reaction the substrate for the alkaline phosphatase conjugate was 5-bromo-4-chloro-3-indolyl phosphate (BCIP) (Sigma, St. Louis, Mo.).

Example 2

Preparation of Antiserum Against 66 kDa 2.1 Purification of 66 kDa

The 66 kDa protein was purified by 12.5% SDS-PAGE of Fraction B obtained from the *B. garinii* IP90 spirochaetes. The appropriate band was visualized by staining the gel with 0.05% CB in water without fixation in MeOH and Acetic acid. The protein band contained approximately 100 μg of 66 kDa.

2.2 Immunization of Rabbits

Approximately 100 μg of the 66 kDa protein prepared as described above was homogenised and used in each of four immunizations of one rabbit performed in one and two (for the last immunization) months intervals. Seven serum samples were obtained during a 5 months period, and serum was diluted 1:1,000 when used for Western blot analysis.

Example 3

Cell Surface Proteolysis of Borrelia Cells 3.1 Protease Treatment of Borreliae Cells Cell surface proteolysis of *B. afzelii* ACAI cells was conducted as previously described (Barbour et al. 1984). Briefly, washed spirochaetes were resuspended in PBS—Mg at a concentration of 2×10$^9$ cells/ml. To 950 μl of the cell suspension was added 50 μl of one of the following: distilled water, proteinase K (Sigma, St Louis, Mo.) (4 mg/ml in water) or trypsin (Gibco BRL, Gaithesburg, Md.) (1 mg/ml in 10$^{-3}$ M HCl). After incubation for 40 min at 20° C. the proteolytic treatment was stopped by the addition of 10 μl from a solution of the peptidase inhibitor phenylmethylsulfonyl fluoride (PMSF) (Sigma, St. Louis, Mo.) (50 mg of PMSF per 1 ml of isopropanol), and the cells were centrifuged and washed twice with PBS—Mg. The pellets were resuspended in TSM buffer. One-third of the cell suspension of each preparation was subjected to the whole cell protein extraction by boiling in SDS-PAGE sample buffer. The remaining part of the suspensions were used to prepare the subcellular fraction of the borrelial outer membrane components, Fraction B, as described above.

3.2 Analysis of the Protease Treated Borrelia Cells

The SDS-PAGE result of the protease treated *B. afzelii* ACAI cells is presented in FIG. 1. As seen in the CB stained protein profiles of the whole-cell lysates (FIG. 1A), proteinase K affected considerably the minor potein with an apparent molecular weight of 66 kDa. The protein composition of the subcellular fractions of outer membrane components (Fraction B) recovered from protease treated and untreated spirochaetes, was also investigated (FIG. 1B). The 66 kDa protein was shown to constitute a substantial part of the Fraction B, obtained from the protease untreated cells. In the Fraction B derived from the spirochaetes proteolysed with trypsin or proteinase K, the 66 kDa protein was, respectively, reduced in amount or entirely absent. The finding that protease treatment reduces the amount of the 66 kDa protein clearly shows that the 66 kDa protein is surface exposed, and most probably associated with the outer membrane of the borrelia.

Example 4

Expression of the 66 kDa Protein in Different Borrelia Species 4.1 SDS-PAGE Analysis The CB stained SDS-PAGE of the whole-cell protein preparations of Lyme disease borreliae and other Borrelia species is shown in FIG. 2A. The 66 kDa protein was present in the whole-cell preparation of *B. burgdorferi* B31, *B. afzelii* ACAI, and *B. garinii* Ip90. The PAGE revealed no major differences among the borrelial strains in respect of either apparent molecular weight or expression level of the 66 kDa protein. In the analogous preparations of *B. hermsii*, *B. crocidurae*, and *B. anserina* no visible band corresponding to the 66 kDa protein was detectable. In addition to being present in fraction B from *B. afzelii* ACAI (cf. example 6), the 66 kDa protein was recovered also in the Fraction B of *B. burgdorferi* B31 and *B. garinii* Ip90, however, it was absent in the Fraction B obtained from *B. crocidurae* and *B. hispanica* (data not shown).

4.2 Western Blotting

In Western blot analysis (FIG. 2B), the 66 kDa protein of *B. burgdorferi* B31, *B. afzelii* ACAI, and *B. garinii* Ip90 reacted similarly with the rabbit antiserum, raised against the 66 kDa protein of the latter strain. There was no apparent reactivity of the antiserum with *B. hermsii*, *B. crocidurae*, *B. anserina* (FIG. 2B), and *B. hispanica* (data not shown) proteins.

The rabbit antiserum raised against the 66 kDa protein of *B. garinii* Ip90, in Western blots reacted equally against 66 kDa protein of *B. burgdorferi* B31 and *B. afzelii* ACAI indicating that 66 kDa protein is highly conserved among Lyme disease associated borreliae.

These data indicate that 66 kDa protein is unique among Lyme disease borreliae. Conversely, it was shown recently that the cspC gene homologues and OspC-related proteins are present in Borrelia species not associated with Lyme borreliosis (Marconi et al. 1993).

Example 5

In vitro growth inhibition of borreliae by antibodies against the 66 kDa protein The in vitro growth inhibition of borreliae by antibodies against the 66 kDa protein was performed as described elsewhere (Sadziene et al. 1993). Briefly, borreliae were grown to the concentration of approximately 10$^8$ cells/ml, as counted in a Petroff-Hauser chamber by phase-contrast microscopy. The concentration of the cells was adjusted to 2×10$^7$ cells/ml by adding fresh medium. 100 μl of the diluted culture was placed in flat-bottomed wells of 96-well microtiter plates, and the rabbit antiserum against the 66 kDa protein prepared as described above diluted twofold in BSK II medium was added. The serum obtained from the same rabbit before the immunization was used for negative control. The plates were then incubated for 72 h at 34° C. and the inhibitory titer of the antiserum was evaluated by comparing the cell counts with the negative control. Complement was inactivated in all sera by heat-treatment at 56° C. for 30 min.

The effect of the rabbit monospecific polyclonal anti-66 kDa protein antibodies on in vitro growth of borreliae was examined. The growth inhibition, occurring after adding the antibodies into the culture, resulted in reduced cell counts and appearing of mainly not mobile spirochetes, carrying large surface blebs. For all Lyme disease associated Borrelia strains included in the assay, in vitro growth was inhibited by the antibodies against the 66 kDa protein. The inhibitory titer of the antiserum was 1:8, 1:4, and 1:4 for, respectively, *B. burgdorferi* B31, *B. afzelii* ACAI, and *B. garinii* Ip90.

The inhibitory titer of the antiserum was 1:16 when the growth inhibition test was performed on the *B. burgdorferi* B31 mutant B313 lacking Ospa and OspB. The antiserum raised against the 66 kDa protein of *B. garinii* Ip90 was able to inhibit the in vitro growth of all three Lyme disease associated Borrelia strains used in the assay. This further indicates that the 66 kDa protein is highly conserved among Lyme disease associated borreliae and hence is an antigen being a potential vaccine candidate and a diagnostic tool.

Example 6

Isolation and N-terminal amino acid sequencing of the 66 kDa protein 6.1 Amino acid sequencing.

The Fraction B of strain ACAI of *B. afzelii* was electrophoresed and transferred to Fluorotrans transfer membrane (Pall, East Hills, N.Y.). The protein bands were visualized by staining the membrane with 0.1% CB in 50% methanol. After destining with 50% methanol, the 66 kDa protein band was cut from the membrane and N-terminal amino acid sequence analysis was performed on a 477A sequenator (Applied Biosystems, Foster City, Calif.) at Umeå University.

N-terminal amino acid sequence of the 66 kDa protein, recovered from the Faction B of *B. afzelii* AcAI, is presented, SEQ ID NO: 1.

6.2 Design of olignoucleotide probe.

The sequence of the 8 amino acid fragment was used to design the olignoucleotide sequence, SEQ ID NO: 2. The choice of A and T nucleotides in the wobble positions was reasoned by the preferential utilization of codons with A and T nucleotides in Borrelia genome (Burman et al. 1990).

Example 7

Preparation of Bb DNA libraries 7.1 Extraction of DNA.

The spirochaetes harvested from 400 ml of culture, were washed twice with 50 mM Tris-HCl (pH=7.4) and resuspended in 10 ml of buffer containing 50 mM Tris-HCl (pH=7.4), 25% sucrose, and 50 mM EDTA. The cells were lysed by adding SDS to a final concentration of 2%, lysozyme (Sigma, St. Louis, Mo.) (1.5 mg/ml), proteinase K (Sigma, St. Lous, Mo.) (0.1 mg/ml), and RNAase A (Sigma, St. Louis, Mo.) (10 μg/ml). The DNA was extracted with buffered phenol and ethanol recipitated.

7.2 Construction of a genomic DNA library.

Restriction enzymes were obtained from Boehringer, Mannheim, Germany. 100 ng of borrelial genomic DNA prepared as described above was completed digested using EcoRI, XbaI, and PstI restriction endonucleases separately or in combination. For the partial digestions, 1 U of HindIII restriction endonuclease was incubated with 100 ng of genomic DNA for 10 min. at 37° C. Twenty nanograms of appropriately digested pUC18 (Pharmacia, Uppsala, Sweden) vector was used for ligations.

Example 8

Cloning and sequencing of the gene encoding the 66 kDa protein 8.1 Screening of genomic library prepared from *B. garinii* Ip90.

The recombinant plasmids were transformed into competent *E. coli* Dh5α cells. Initially, *B. garinii* Ip90 HindIII digested genomic DNA library was screened with the designed degenerated oligonucleotide probe:

5'-GAA AAA GAT ATW TTT AAA ATW AAT-3' (SEQ ID NO: 2)

synthesized on the basis of the N-terminal amino acid sequence of the 66 kDa protein obtained in Example 5 (corresponding to amino acids 6–13). A recombinant plasmid designated (pJB-100) recovered from one positive *E. coli* Dh5α clone was sequenced. A gene fragment containing 592 bp including the ATG start codon followed by a discontinued open reading frame (ORF) was identified. The full-length 66 kDa protein gene was retrieved from *B. garinii* Ip90 EcoRI/XbaI genomic DNA library in the same vector by probing with the radiolabelled 66 kDa protein gene fragment within BamHI and HindIII restriction sites on pJB-100. A recombinant plasmid designated pJB-101 derived from another positive *E. coli* Dh5α clone, harboured a 4.1 kb DNA insert. The sequencing of the 66 kDa protein gene proceeded until the TAA stop codon was detected. The clones were sequenced by the dideoxy chain termination method, using $/\gamma-^{35}S/dATP$ (Amersham, Buckinghamshire, UK) and the Pharmacia T7 sequencing kit according to the procedure described by the manufacturer (Pharmacia, Uppsala, Sweden). The sequence fragments were assembled using the GENEUS software for VAX computer.

8.2 Screening of genomic library prepared from *B. burgdorferi* B31 and *B. afzelli* ACAI.

The 592 bp 66 kDa protein gene fragment within BamHI and HindIII restriction sites was recovered from plasmid preparation and radiolabelled by random primer technique. It was then used to screen *B. burgdorferi* B31 and *B. afzelii* ACAI genomic DNA libraries. A recombinant plasmid designated pJB-102was found to harbour a 2.4 kb insert comprising a segment of the 66 kDa protein gene from *B. burgdorferi* B31 lacking the coding sequence for the signal peptide and a recombinant plasmid designated pJB-105 was found to harbour a 1.5 kb insert comprising the DNA encoding the initial Met and the following 17 amino acids. Together with the DNA sequence found in pJB-102, the full sequence encoding the 66 kDa protein from B31 was then established. A recombinant plasmid designated pJB-104 was found to harbour a 10 kb insert comprising the complete 66 kDa protein gene from *B. afzelii* ACAI. Both strands of the full-length genes coding for the 66 kDa proteins in different Lyme disease Borrelia species were sequenced as described above.

8.3 Sequence analysis.

Sequence analyses were performed using the University of Wisconsin GCG Sequence Analysis Software Version 7.2 for VAX computer, MacVector (IBI, Newhaven Conn.) for Macintosh computers, and PC-Gene (Genofit) for XT/AT personal computers. Search in protein sequence databases were performed at the NCBI using the BLST network service.

The nucleotide sequence of the 66 kDa protein gene of *B. burgdorferi* B31, *B. afzelii* ACAI, *B. garinii* Ip90, as well as neighbouring regions are shown in SEQ ID NO: 3, SEQ ID NO: 5 SEQ ID NO: 7, and SEQ ID NO: 13. The ATG start codon was followed by ORF of 1857, 1860 and 1866 nucleotides for strains B31, ACAI, and Ip90, respectively. A consensus ribosomal binding size (RBS), GGAAGG, could be detected upstream of the start codon. Further upstream, sequences closely resembling the "-10"-region (—TATTAT—) and the "-35"-region (—TTGAAT—) were located at positions -185 and -209, respectively. The B31 clone did not contain the ATG start codon and the sequence coding for the signal sequence, but contained the sequence coding for the complete processed protein. The 66 kDa protein gene terminated at a TAA triplet, which was followed by AT which region containing putative stem and loop structures.

The deduced amino acid sequence of the 66 kDa protein of *B. burgdorferi* B31, *B. afzelii* ACAI and *B. garinii* Ip90 is presented in SEQ ID NO: 4 and SEQ ID NO: 14, SEQ ID NO: 6 and SEQ ID NO: 8, respectively. The computer analysis predicted the potential leader peptidase I cleavage site between amino acid residues at position 21, and the N-terminal peak was found on the hydrophobicity plot (data not shown) in all three cases. The processed 66 kDa protein from the strains B31, ACAI and Ip90 consisted of, respectively, 597, 598 and 600 amino acids with a calculated molecular weight of 65,802 kDa, 65,796 kDa and 65.944 kDa. The amino acid sequence of the 66 kDa protein from *B. burgdorferi* 531 was 92.7% and 91.5% identical to the sequences from, respectively, *B. afzelii* ACAI and *B. garinii* Ip90. When compared with each other, the two latter strains showed 93.9% identity.

The level of similarity and identity between the deduced amino acid sequence of the 66 kDa protein from different borrelia strains further shows that this protein can be useful as a vaccine against Lyme disease as well as a target for diagnostic use.

Antigenicity Plot

Potential antigenic regions of the deduced amino acid sequences of the 66 kDa proteins from *Borrelia burgdorferi* sensu stricto B31, *Borrelia afzelii* ACAI, and *Borrelia garinii* EP90 were identified by calculation of the antigenic index using the algorithm of Jameson and Wolf (1986). The results are shown in FIG. 5. Proposed epitopic regions having a high antigenic index are e.g. the amino acid sequences corresponding to positions 175–190, 285–305, 365–385, and 465–490.

The 66 kDa proteins were examined for the sequence similarity to other known proteins in database libraries. There were no other sequences related significantly to the 66 kDa proteins.

Example 9

Localization of the 66 kDa protein gene 9.1 Separation of DNA by pulse-field agarose gel electrophoresis.

For the pulse-field AGE, the genomic DNA prepared from *B. burdorferi* B31, *B. afzelli* ACAI and *B. garinii* Ip90 was recovered in 1% agarose blocks as previously described (Ferdowns and Barbour, 1989). One-dimensional and pulse-field AGE were performed in 0.7% and 1% agarose, respectively, in TBE buffer. For the pulse-field AGE pulse times were 1 s for 9 h and then 5 s for 9 h at a constant current of 180 mA.

9.2 Southern blotting.

Following depurination, denaturationn and neutralization of the gels, the DNA was transferred to Hybond-N membrane (Amersham, Buckinghamshire, UK) by the method of Southern (Sambrook et al. 1989), and cross-linked with UV light. Filters were prehybridized and hybridized for, respectively, 1 h and 4 h, and washed. The temperature was 37° C. for probing with degenerate oligonucleotide, end-labelled with /γ-$^{32}$P/dATP (Amersham, Buckinghamshire, UK), and 55°°C. for probing with DNA fragment, radiolabelled by random primer technique (Amersham, Buckinghamshire, UK).

The hybridizing band corresponded to the position of the 1 Mbp linear chromosome of Lyme disease borreliae, cf. FIG. 3.

There was no significant signs of hybridization with the DNA from relapsing fever Borrelia species, *B. hermsii, B. crocidurae,* and *B. hispanica* (data not shown).

Furthermore, the 66 kDa protein gene being localized to the chromosome of borreliae shows a higher degree of conservation among Lyme disease associated borreliae contrary to the plasmid-encoded major outer surface proteins A, B, and C which exhibit significant species and strain dependent genetic and antigenic polymorphisms (Barbour 1986, Jonsson et al. 1992, Wilske et al. 1993).

Example 10

Expression of the 66 kDa protein from *B. burgdorferi* B31 in *E. coli*

Two oligonucleotide primers.

| | |
|---|---|
| 5'-GCA ATA TTT GCT GCA GCA GAT-3' | SEQ ID NO: 11 |
| 5'-GGC CTA AAG GAA TTC TTT TGC-3' | SEQ ID NO: 12 | were designed to anneal to the 5' end (devoid of the leader peptide sequence) and the 3' end of the 66 kDa protein gene from *B. burgdorfer* B31. The primers contained, respectively, PstI and EcoRI restriction sites, and were used to amplify the 66 kDa protein gene in the PCR. PCR amplification was performed using Ampli-Taq DNA polymerase (Perkin Elmer Cetus, Norwalk, Conn.). The PCR product was then treated with the mentioned restriction enzymes, purified by AGA and ligated into the T7 based expression vector pRSET (Invitrogen, San Diego, Calif.). The recombinant pasmid was then used to transform *E. coli* BL21 cells. *E. coli* BL21 cells containing the insert were grown and induced with by adding isopropyl-β-D-thiogalactopyranoside (IPTG) (Sigma, St. Louis, Mo.) to a final concentration of 1 mM to express the introduced 66 kDa protein gene. The 66 kDa protein gene product was subsequently identified by SDS-PAGE and Western blot with rabbit antiserum raised against the 66 kDa protein. FIG. 4 show the southern blot.

REFERENCES

Adam T, Gassmann G S, Rasiah C, Göbel U B. 1991. Phenotypic and genotypic analysis of *Borrelia burgdorferi* isolates from various sources. Infection and Immunity, 59: 2579–2585.

Adelamn et al. 1983. DNA, 2: 183.

Anderson J F, Magnarelli L A, McAnich J B, 1988. Journal of Clinical Microbiology, 26: 2209–2212.

Arimitsu Y, Takashima I, Yoshii Z, Higashi Y, Kameyama S, Mizuguchi J. 1991. Journal of Infectious Diseases, 163: 682–683.

Baranton G, Postic D, Saint Girons I, Boerlin P, Piffaretti J-C, Assous M, Grimont P A D. 1992. Delineation of

*Borrelia burgdorferi* sensu stricto, Borrelia gariniisp. nov., and group VS461 associated with Lyme borreliosis. International Journal of Systematic Bacteriology, 42: 376–383.

Barbour A G, Burgdorfer W, Grunwaldt E, Steere Ac. 1983. Antiobodies of patients with Lyme disease to components of the Ixodes damini spirochete. Journal of Clinical Investigation, 72: 504–515.

Barbour A G, Tessier S L, Hayes S F. 1984, Variations in a major surface protein of Lyme disease spirochetes. Infection and Immunity, 45: 94–100.

Barbour A G. 1984. Immunochemical analysis of Lyme disease spirochetes. The Yale Journal of Biology and Medicine, 57: 581–586.

Barbour A G. 1986. Polymorphisms of major surface proteins of *Borrelia burgdorferi*. Zbl Bakt Hyg, 263: 83–91.

Barbour A G. 1988. Journal of Clinical Microbiology, 26: 475–478.

Barthold S W, Bockenstedt L K. 1993, Passive immunizing activity of sera from mice infected with *Borrelia burgdorferi*. Infection and Immunity, 61: 4696–4702.

Beaucage S L., Caruthers M M et al. 1981. Tetrahedron Letters, 22: 1859–1862.

Bergström S, Sjöstedt A, Dotevall L, Kaijser B. Ekstrand-Eammarström B, Wallberg C, Skogman G, Barbour A G. 1991. Diagnosis of Lyme borrelicsis by an enzyme immunoassay detecting immunoglobulin G reactive to purified *Borrelia burgdorferi* cell components. European Journal of Clinical Microbiology and Infectious Diseases, 10: 422–427.

Bolivar et al. Gene, 2: 95.

Brucebauer E. R., Preac-Mursic V, Fuchs R, Wilske B. 1992. Cross reactive proteins of *Borrelia burgdorferi*. European Journal of Infectious Diseases, 3: 224–232.

Burgdorfer W, Barbour A G, Hayes S F, Benach J L, Grunwaldt E, Davis J P. 1983 Lyme disease- a tick borne spirochetosis? Science, 216: 1317–1319.

Burman N, Bergström S, Restrepo B I, Barbour A G. 1990. The variable antigens Vmp7 and Vmp21 of the relapsing fever bacterium *Borrelia hermsii* are structurally analogous to the VSG proteins of the African trypanosome. Molecular Microbiology, 4: 1715–1726.

Canica M M, Nato F, duMerle L, Mazie J C. Barantonn G, Postic D. 1993. Monoclonal antibodies for identification of *Borrelia afzelii* sp. nov. associated with late cutaneous manifestatons of Lyme borreliosis. Scandinavian Journal of Infectious Diseases, 25: 441–448.

Chang et al. 1978. Nature, 375: 515.

Coleman J L, Benach J L. 1987. Isolation of antigenic components from the Lyme disease spirochete: their role in early diagnosis. Journal of Infections Diseases, 155: 756–765.

Craft J E, Grodzicki R L, Steere A C. 1984. Journal of Infectious Diseases, 149: 789–795.

Crea et al. 1978. Proceeding of the National Academy of Sciences USA, 75: 5765.

Dressler F, Whalen J A, Reinhardt B N, Steere A C. 1993. Western blotting in the serodiagnosis of Lyme disease. The Journal of Infectious Diseases, 167: 392–400.

Eichenlaub R. 1979. Journal of Bacteriology, 138: 559–566.

Erdile L F, Brandt M-N, Warakomski D J, Westrack G J, Sadziene A, Barbour A G, Mays J P. 1993. Role of attached lipid in immunogenicity of *Borrelia burgdorferi* Ospa. Infection and Immunity, 61: 81–90.

Ferdows M S, Barbour A G. 1989. Megabase-sized linear DNA in the bacterium *Borrelia burgdorferi*, the Lyme disease agent. Proceedings of National Academy of Science, 86: 5969–5973.

Fiers et al. 1978. Nature, 273: 113.

Fikrig E, Barthod S W, Marcantonio N, DePonte K, Kantor F S, Flavell R A. 1992. Roles of OspA, OspB, and flagellin in protective immunity to Lyme borreliosis in laboratory mice. Infection and Immunity, 60: 675–661.

Fikrig E, Barthold S W, Persing D. E, Sun X, Kantor F S, Flavell R A. 1992. *Borrelia burgdorferi* strain 25015: characterization of cuter surface protein A and vaccination against infection. Journal of Immunology, 148: 2256–2260.

Gassmann G S, Jacobs E, Deutzmann R, Göbel U E. 1991. Analysis of fla gene of *Borrelia burgdorferi* GeHo and antigenic characterization of its gene product. Journal of Bacteriology, 173: 1452–1459.

Godman J L, Jarkovich P, Kramber J M, Johnson R C. 1991. Infection and Immunity, 59: 269–278.

Goeddel et al. 1979. Nature, 281: 544.

Grodzicki R L, Steere A C. 1988. Comparison of immunoblotting and indirection enzyme-linked immunosorbent assay using different antigen preparations for diagnosing early Lyme disease. Journal of Infectious Diseases, 157: 790–797.

Hess et al. 1968. Journal od Advanced Enzyme Regulation, 7: 149.

Hitzeman et al. 1980. Journal of Biological Chemistry, 255: 2073.

Holland et al. 1978. Biochemistry, 17: 4900.

Hopp T P, Woods K. R. 1981. Proceedings of the National Academy of Science USA, 78: 3824–3828.

Itakura et al. 1977. Science, 198: 1056.

Jameson B A, Wolf H. 1988. Computer Application in the biosciences, 4: 181–186

Jones. 1977. Genetics, 84: 12.

Jonsson M, Noppa L, Barbour A G, Bergström S. 1992. Heterogeneity of outer membrane proteins in *Borrelia burgdorferi:* comparison of osp opersons of three isolates of different geographic origins. Infection and Immunity, 60: 1845–1853.

Kimgsman et al. 1979. Gene, 7: 141.

Kryuchechnikov V N, Korenberg E I, Scherbakov S V, Kovalevsky Y V, Levin M L. 1988. Identification of Borrelia isolated in the USSR from Ixodes persulcatus schulze ticks. Journal of Microbiology, Epidemiology and Immunobiology, 12: 41–44.

Kyte J, Doolittle R F. 1982. Journal of Molecular Biology, 157: 105–132.

Laemmli U K. 1970. Nature 227:680–685

Lebech A M. Hindersson P, Vuust J, Hansen K J. 1991. Journal of Clinical Microbiology, 29: 731–737.

Luft B J. Jiang W. Munoz P, Dattwyler R J Gorevic R D. 1989. Biochemical and immunological characterization of the surface proteins of *Borrelia burdorferi*. Infection and Immunity, 57: 3637–3645.

Luft B J, Gorevic P D, Jiang W, Munoz P. Dattwyler R J. 1991. Immunologic and structural characterization of the dominant 66- to 73-kDa antigens of *Borrelia burgdorferi*. Journal of Immunology, 146: 2776–2782.

Ma B, Christen B. Leung D, Vigo-Pelfrey C. 1992. Serodiagnosis of Lyme borreliosis by Western immunoblot: reactivity of various significant antibodies against *Borrelia burgdorferi*. Journal of Clinical Microbiology, 30: 370–376.

Magnarelli L A., Anderson J F, BarbourAG. 1989. Enzyme-linked immunosorbent assays for Lyme disease: reactivity of subunits of *Borrelia burgdorferi*. Cross-reactivity in serologic tests for Lyme disease and other spirochetal infections. Journal of Infectious Diseases, 159: 43–49.

Magnarelli L A., Anderson J F, Johnson R C. 1987. Cross-reactivity in serologic tests for Lyme disease and other spirochetal infections. Journal of Infectious Diseases, 156: 183–188.

Magnarelli L A., Miller J N, Anderson J F, Riviere G R. 1990. Cross-reactivity of nonspecific treponemal antibody in serologic tests for Lyme disease. Journal of Clinical Microbiology, 28: 1276–1279.

Marconi R T, Garon C F. 1992. Phylogenetic analysis of the genus Borrelia: a comparison of North American and European isolates of Borrelia burgdorferi. Journal of Bacteriology, 174: 241–244.

Marconi R T, Konkel M E, Garon C P. 1993. Variability of osp genes and gene products among species of Lyme disease spirochetes. Infection and Immunity, 61: 2611–2617.

Marconi R T, Samuels D S, Schwan T G, Garon C F. 1993, Identification of a protein in several Borrelia species which is related to OspC of Lyme disease spirochetes. Journal of Clinical Microbiology, 31: 2577–2583.

Messing et al. 1981. Third Cleveland Symposium on Macromolecules and Recombinant DNA, Ed. A Walton, Elsevier, Amsterdam.

Nielsen P E et al., 1991, Science 254: 1497–1500.

Norris S J, Carter C J, Howell J K, Barbour A G. 1992. Low-passage-associated proteins of Borrelia burgdorferi B31: Characterization and molecular cloning of OspD, a surface exposed, plasmid-encoded lipoprotein. Infection and Immunity, 60: 4662–4762.

Norton Hughes C A, Engstrom S M, Coleman L A, Kodner C B, Johnson R C. 1993. Protective immunity is induced by a Borrelia burgdorferi mutant that lacks OspA and OspB. Infection and Immunity, 61: 5115–5122.

Olsen B, Jaenson T G T, Noppa L, Bunikis J, Bergström S. 1993. A Lyme borreliosis cycle in seabirds and Ixodes uriae ticks. Nature, 362: 340–342.

Preac-Mursic V, Wilske B, Patsouris E, Jauris S, Will G, Soutschek E, Reinhardt S, Lehnert G, Klockmann U, Mehraein P. 1992. Active immunization with pC protein of Borrelia burgdorferi protects gerbils against Borrelia burgdorferi infection. Infection, 20: 342–349.

Rahn D W, Malawista S E. 1991. Annals of Internal Medicine, 114: 472–481.

Raoult D, Eechemy K E, Baranton G. 1989. Crossreaction with Borrelia burgdorferi antigen of sera from patients with human immunodeficiency virus infection, syphilis, and leptospirosis. Journal of Clinical Microbiology, 27: 2152–2155.

Rosa P A, Schwan T G. 1989. Journal of infectious diseases, 160: 1018–1029.

Sadziene A, Thompson R A, Barbour A G. 1993. In vitro inhibition of Borrelia burgdorferi growth by antibodies. Journal of Infectious Diseases, 167: 165–172.

Sambrook J, Fritsch E F, Maniatis T. 1989. Molecular cloning: a laboratory manual, 2nd ed. Cold Spring Harbor Laboratory, Cold Spring Harbor, N.Y.

Schmid G P. 1985. Reviews of infectious diseases, 7: 41–49.

Shanafelt M C, Hinderson P, Soderberg C, Mensi N, Turck C W, Webb D, Yssel H, Peltz G. 1991. Journal of Immunology, 146: 3986–3992.

Siebwenlist et al. 1980, Cell, 20: 269.

Simon M M, Schaible U E, Wallich R, Kramer M D. 1991. A mouse model for Borrelia burgdorferi infection: approach to a vaccine against Lyme disease. Immunology Today, 12: 11–16.

Simpson W J, Schrumpf M E, Schwan T G. 1990. Reactivity of human Lyme borrelicsis sera with a 39-kilodalton antigen specific to Borrelia burgdorferi. Journal of Clinical Microbiology, 28: 1329–1337.

Steere A C, Malawista S E, Syndman D R. 1977. Arthritis and rheumatism 20: 7–17.

Steere A C, Taylor E, Wilson M L, Levine J F, Spielman A. 1986. Journal of Infectious Diseases, 154: 295–300.

Steere A C. 1989. Lyme disease. New England Journal of Medicine, 321: 586–596.

Stinchomb et al. 1979. Nature 282: 39.

Theisen M, Frederiksen B, Lebech A-M, Vuust J, Eansen K. 1993. Polymorphism in ospC gene of Borrelia burgdorferi and immunoreactivity of OspC protein: implications for taxonomy and for use of OspC protein as a diagnostic antigen. Journal of Clinical Microbiology, 31: 2570–2576.

Tschemper et al. 1980. Gene, 10: 157.

Ulmer J B et al. 1993. Curr. Opin. Invest. Drugs, 2: 983–989.

Wallich R, Moter S E, Simon M M, Ebnet K, Eeiberger A, Kramer M D. 1990. Infection and Immunity, 58: 1711–1719.

Wilske B, Preac-Mursic V, Jauris S, Hofman A, Pradel I, Soutschek E, Schwab E, Will G, Wanner G. 1993. Immunological and molecular polymorphisms of OspC, an immunodominant major outer surface protein of Borrelia burgdorferi. Infection and Immunity, 61: 2182–2191.

Wilske B, Preac-Mursic V, Schierz G, Busch K V. 1986. Immunochemical and immunological analysis of European Borrelia burgdorferi strains. Zbl Bakt Hyg, 263: 92–102. Zingg B C, Anderson J F, Johnson R C, LeFebvre R B. 1993. Comparative analysis of genetic variability among Borrelia burgdorferi isolates from Europe and the United States by restriction enzyme analysis, gene restriction fragment length polymorphism, and pulse-field gel electrophoresis. Journal of Clinical Microbiology, 31: 3115–3122.

Asbrink E, Hovmark A, Hederstedt B. 1984. The spirochetal etiology of acrodermatitis chronica atrophicans Herxheimer. Acta Dermatologica et Venerologia, 64: 506–512.

What is claimed is:

1. An isolated and substantially pure polypeptide selected from the group consisting of the 66 kDa protein of *Borrelia afzelli* ACAI having the amino acid sequence 1–598 of SEQ ID NO: 6 and the 66 kDa protein of *Borrelia garinii* IP90 having the amino acid sequence 1–600 of SEQ ID NO: 8.

2. An isolated and substantially pure polypeptide having the amino acid sequence 1–598 of SEQ ID NO: 6.

3. An isolated and substantially pure polypeptide having the amino acid sequence 1–600 of SEQ ID NO: 8.

4. An isolated and substantially pure polypeptide selected from the group consisting of the 66 kDa protein of *Borrelia afzelli* ACAI consisting essentially of the amino acid sequence 1–598 of SEQ ID NO: 6 and the 66 kDa protein of *Borrelia garinii* IP90 consisting essentially of the amino acid sequence I-600 of SEQ ID NO: 8.

5. An isolated and substantially pure polypeptide consisting essentially of the amino acid sequence 1–598 of SEQ ID NO: 6.

6. An isolated and substantially pure polypeptide consisting essentially of the amino acid sequence 1–600 of SEQ ID NO: 8.

7. An isolated and substantially pure polypeptide having an amino acid sequence which has a sequence homology of at least 92% with the amino acid sequence 1–598 of SEQ ID NO: 6, and wherein the polypeptide reacts with rabbit anti-serum raised against the 66 kDa protein of *Borrelia garinii* IP90.

8. An isolated and substantially pure polypeptide having an amino acid sequence which has a sequence homology of at least 92% with the amino acid sequence 1–600 of SEQ ID NO: 8, and wherein the polypeptide reacts with rabbit anti-serum against the 66 kDa protein of *Borrelia garinii* IP90.

9. The polypeptide of any one of claims 1–8, wherein the polypeptide is a recombinant polypeptide prepared by a process comprising expressing, in a cell which does not natively express it, a nucleic acid fragment comprising a nucleotide sequence encoding the polypeptide.

10. The polypeptide of any one of claims 1–8, wherein the polypeptide is a synthetic polypeptide prepared by a process selected from the group consisting of solid phase peptide synthesis and liquid-phase peptide synthesis.

11. A fusion polypeptide comprising the polypeptide according to any one of claims 1–8 and a fusion partner.

12. The fusion polypeptide of claim 11, wherein the fusion partner is a polypeptide fragment which facilitates the expression of the fusion polypeptide in a host cell.

13. The fusion polypeptide of claim 11, wherein the fusion partner is selected from the group consisting of second Borrelia polypeptide, an outer membrane lipoprotein, a viral protein, an immunoglobulin binding protein, a T-cell epitope, a B-cell epitope, a bacterial fimbrial protein, a maltose binding protein, gluthatione S-transferase, B-galactosidase, and polyhistidine, wherein the second the Borrelia polypeptide is selected from the group consisting of the amino acid sequence 175–190, 285–305, 365–385 and 465–490, as set forth in SEQ ID NO: 4, 6, 8 and 14, wherein the outer membrane lipoprotein is selected from the group consisting of *E. coli* outer membrane lipoprotein and OspA of *Borrelia burgdorferi* sensu lato, wherein the viral protein is selected from the group consisting of hepatitis B surface antigen, hepatitis B core antigen and the influenze virus non-structural protein NS1, wherein the immunoglobulin binding protein is selected from the group consisting of protein A, protein G and the synthetic ZZ-peptide, and wherein the bacterial fimbrial protein is selected from the group consisting of pilus components of pilin and papA.

14. An immunological composition comprising the polypeptide of any one of claims 1–8 and a pharmaceutically acceptable carrier.

15. A method for inducing an immunological response in an animal comprising administering to the animal the immunological composition of claim 14.

16. An immunological composition comprising the polypeptide of claim 11 and a pharmaceutically acceptable carrier.

17. A method for inducing an immunological response in an animal comprising administering to the animal the immunological composition of claim 16.

18. An isolated and substantially pure polypeptide consisting essentially of an amino acid sequence selected from the group consisting of: the amino acids 285–305 of the *Borrelia afzelli* ACAI 66 kDa protein of SEQ ID NO:6, the amino acids 365–385 of the *Borrelia afzelli* ACAI 66 kDa protein of SEQ ID NO:6, the amino acids 465–490 of the *Borrelia afzelli* ACAI 66 kDa protein of SEQ ID NO:6, the amino acids 285–305 of the *Borrelia garinii* IP90 66 kDa protein of SEQ ID NO:8, the amino acids 365–385 of the *Borrelia garinii* IP90 66 kDa protein of SEQ ID NO:8, and, the amino acids 465–490 of the *Borrelia garinii* IP90 66 kDA protein of SEQ ID NO:8.

19. The polypeptide of claim 18 having an amino acid sequence consisting essentially of the amino acids 285–305 of the *Borrelia afzelli* ACAI 66 kDa protein of SEQ ID NO:6.

20. The polypeptide of claim 18 having an amino acid sequence consisting essentially of the amino acids the amino acids 365–385 of the *Borrelia afzelli* ACAI 66 kDa protein of SEQ ID NO: 6.

21. The polypeptide of claim 18 having an amino acid sequence consisting essentially of the amino acids 465–490 of the *Borrelia afzelli* ACAI 66 kDa protein of SEQ ID NO:6.

22. The polypeptide of claim 18 having an amino acid sequence consisting essentially of the amino acids 285–305 of the *Borrelia gariniii* IP90 66 kDa protein of SEQ ID NO:8.

23. The polypeptide of claim 18 having an amino acid sequence consisting essentially of the amino acids 365–385 of the *Borrelia gariniii* IP90 66 kDa protein of SEQ ID NO:8.

24. The polypeptide of claim 18 having an amino acid sequence consisting essentially of the amino acids 465–490 of the *Borrelia garinii* IP90 66 kDa protein of SEQ ID NO:8.

25. An isolated and substantially pure polypeptide comprising a truncated portion of the 66 kDa membrane protein comprising an amino acid sequence selected from the group consisting of the amino acids 285–305 of the *Borrelia afzelli* ACAI 66 kDa protein of SEQ ID NO:6, the amino acids 365–385 of the *Borrelia afzelli* ACAI 66 kDa protein of SEQ ID NO:6, the amino acids 465–490 of the *Borrelia afzelli* ACAI 66 kDa protein of SEQ ID NO:6, the amino acids 285–305 of the *Borrelia garinii* IP90 66 kDa protein of SEQ ID NO:8, the amino acids 365–385 of the *Borrelia garinii* IP90 66 kDa protein of SEQ ID NO:8, and, the amino acids 465–490 of the *Borrelia garinii* IP90 66 kDa protein of SEQ ID NO:8.

26. The polypeptide of claim 25 comprising the amino acids 285–305 of the *Borrelia afzelli* ACAI 66 kDa protein of SEQ ID NO:6.

27. The polypeptide of claim 25 comprising the amino acids the amino acids 365–385 of the *Borrelia afzelli* ACAI 66 kDa protein of SEQ ID NO:6.

28. The polypeptide of claim 25 comprising the amino acids 465–490 of the *Borrelia afzelli* ACAI 66 kDa protein of SEQ ID NO:6.

29. The polypeptide of claim 25 comprising the amino acids 285–305 of the *Borrelia gariniii* IP90 66 kDa protein of SEQ ID NO:8.

30. The polypeptide of claim 25 comprising the amino acids the amino acids 365–385 of the *Borrelia gariniii* IP90 66 kDa protein of SEQ ID NO:8.

31. The polypeptide of claim 25 comprising the amino acids 465–490 of the *Borrelia garinii* IP90 66 kDa protein of SEQ ID NO:8.

32. An isolated and substantially pure polypeptide selected from the group consisting of polypeptides consisting essentially of the amino acids sequence 175–190, 285–305, 365–385 and 465–490, as set forth in SEQ ID NOs: 4, 6, 8 and 14.

33. An isolated and substantially pure polypeptide having an amino acid sequence consisting essentially of the amino acid sequence 175–190 of SEQ ID NO:4.

34. An isolated and substantially pure polypeptide having an amino acid sequence consisting essentially of the amino acid sequence 465–490 of SEQ ID NO:14.

35. The polypeptide of any one of claims 18–35 wherein the polypeptide is a recombinant polypeptide prepared by a process comprising expressing, in a cell which does not natively express it, a nucleic acid fragment comprising a nucleotide sequence encoding the polypeptide.

36. The polypeptide of any one of claims 18–35 wherein the polypeptide is a synthetic polypeptide prepared by a process selected from the group consisting of solid phase peptide synthesis and liquid-phase peptide synthesis.

37. A fusion polypeptide comprising the polypeptide according to any one of claims 94–110 and a heterologous fusion partner.

38. The fusion polypeptide of claim 37, wherein the fusion partner is a polypeptide fragment which facilitates the expression of the fusion polypeptide in a host cell.

39. The fusion polypeptide of claim 37, wherein the fusion partner is selected from the group consisting of a second Borrelia polypeptide, an outer membrane lipoprotein, a viral protein, an immunoglobulin binding protein, a T-cell epitope, a B-cell epitope, a bacterial fimbrial protein, a maltose binding protein, gluthatione S-transferase, B-galactosidase, and polyhistidine, wherein the second Borrelia polypeptide is selected from the group consisting of the amino acid sequence 175–190, 285–305, 365–385 and 465–490, as set forth in SEQ ID NOs:4, 6, 8 and 14, wherein the outer membrane lipoprotein is selected from the group consisting of *E. coli* outer membrane lipoprotein and OspA of *Borrelia burgdorferi* sensu lato, wherein the viral protein is selected from the group consisting of hepatitis B surface antigen, hepatitis B core antigen and the influenze virus non-structural protein NS1, wherein the immunoglobulin binding protein is selected from the group consisting of protein A, protein G and the synthetic ZZ-peptide, and wherein the bacterial fimbrial protein is selected from the group consisting of pilus components of pilin and papA.

40. An immunological composition comprising the polypeptide of any one of claims 18–34 and a pharmaceutically acceptable carrier.

41. A method for inducing an immunological response in an animal comprising administering to the animal the immunological composition of claim 40.

42. An immunological composition comprising the polypeptide of claim 37 and a pharmaceutically acceptable carrier.

43. A method for inducing an immunological response in an animal comprising administering to the animal the immunological composition of claim 42.

* * * * *

UNITED STATES PATENT AND TRADEMARK OFFICE
CERTIFICATE OF CORRECTION

PATENT NO.   : 6,509,017 B1
DATED        : January 21, 2003
INVENTOR(S)  : Swen Bergstrom et al.

It is certified that error appears in the above-identified patent and that said Letters Patent is hereby corrected as shown below:

<u>Title page,</u>
Item [73], Assignee, change "Molndal (DE)" to -- Molndal (SE) --.

<u>Column 73,</u>
Lines 34-35, change "comprising the amino acids the amino acids 365-385" to -- comprising the amino acids 365-385 --.
Line 41, change "Borrelia gariniii" to -- Borrelia garinii --.
Lines 43-44, change "comprising the amino acids the amino acids 365-385 of the Borrelia gariniii" to -- comprising the amino acids 365-385 of the Borrelia garinii --.

Signed and Sealed this

Twenty-seventh Day of May, 2003

JAMES E. ROGAN
*Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 20 amino acids (B) TYPE: amino acid
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Borrelia afzelii
        (B) STRAIN: ACAI (xi) SEQUENCE DESCRIPTION: SEQ ID NO: 1:

Ala Asp Ala Leu Lys Glu Lys Asp Ile Phe Lys Ile Asn Pro Gly Ile
1               5                   10                  15

Pro Asp Phe Gly
            20

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

GAAAAAGATA TWTTTAAAAT WAAT                                        24

(2) INFORMATION FOR SEQ ID NO: 3:

(i) SEQUENCE CHARACTERISTICS:
        (A) LENGTH: 2075 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia burgdorferi
        (B) STRAIN: B31

(vii) IMMEDIATE SOURCE:
        (B) CLONE: pJB-102

(ix) FEATURE:
        (A) NAME/KEY: CDS
        (B) LOCATION: 109..1914

(ix) FEATURE:
        (A) NAME/KEY: sig_peptide
        (B) LOCATION: 109..120
        (D) OTHER INFORMATION: /partial
            /label= partial (ix) FEATURE:
        (A) NAME/KEY: mat_peptide
        (B) LOCATION: 121..1911

(xi) SEQUENCE DESCRIPTION: SEQ ID NO: 3:

GCTGGCGGAA GGGGGATGTG CTGCAAGGCG ATTAAGTTGG GTAACGCCAG GGTTTTCCCA        60

GTCACGACGT TGTAAAACGA CGGCCAGTGC CAAGCTTGCA TGCCTGCA GCA ATA TTT       117
                                                    Ala Ile Phe
                                                        -4

GCA GCA GAC GCA TTA AAG GAA AAA GAT ATA TTT AAA ATA AAC CCA TGG        165
Ala Ala Asp Ala Leu Lys Glu Lys Asp Ile Phe Lys Ile Asn Pro Trp
1               5                   10                  15

```
ATG CCA ACA TTT GGA TTT GAA AAC ACA AGT GAA TTC AGA TTA GAT ATG    213
Met Pro Thr Phe Gly Phe Glu Asn Thr Ser Glu Phe Arg Leu Asp Met
            20                  25                  30

GAC GAG CTT GTT CCT GGG TTT GAA AAC AAA AGC AAA ATT ACC ATT AAG    261
Asp Glu Leu Val Pro Gly Phe Glu Asn Lys Ser Lys Ile Thr Ile Lys
        35                  40                  45

CTT AAA CCA TTT GAA GCT AAT CCC GAA TTA GGC AAA GAC GAT CCA TTC    309
Leu Lys Pro Phe Glu Ala Asn Pro Glu Leu Gly Lys Asp Asp Pro Phe
    50                  55                  60

TCA GCT TAC ATT AAG GTA GAA GAT CTT GCA CTA AAA GCG GAA GGC AAA    357
Ser Ala Tyr Ile Lys Val Glu Asp Leu Ala Leu Lys Ala Glu Gly Lys
65                  70                  75

AAA GGC GAT CAA TTT AAA ATT GAC GTG GGA GAT ATT ACA GCC CAA ATC    405
Lys Gly Asp Gln Phe Lys Ile Asp Val Gly Asp Ile Thr Ala Gln Ile
80                  85                  90                  95

AAT ATG TAC GAT TTT TTT ATT AAA ATA AGT ACT ATG ACA GAT TTT GAC    453
Asn Met Tyr Asp Phe Phe Ile Lys Ile Ser Thr Met Thr Asp Phe Asp
                100                 105                 110

TTT AAT AAA GAG TCT TTA TTT AGT TTT GCA CCT ATG ACT GGA TTT AAA    501
Phe Asn Lys Glu Ser Leu Phe Ser Phe Ala Pro Met Thr Gly Phe Lys
            115                 120                 125

AGC ACT TAC TAT GGA TTC CCA AGC AAT GAT AGG GCA GTA AGA GGG ACA    549
Ser Thr Tyr Tyr Gly Phe Pro Ser Asn Asp Arg Ala Val Arg Gly Thr
        130                 135                 140

ATT CTT GCA AGA GGT ACT TCT AAA AAC ATA GGA ACA ATT CAG CTG GGA    597
Ile Leu Ala Arg Gly Thr Ser Lys Asn Ile Gly Thr Ile Gln Leu Gly
    145                 150                 155

TAC AAA CTC CCA AAA CTC GAC CTT ACA TTT GCA ATA GGG GGA ACA GGC    645
Tyr Lys Leu Pro Lys Leu Asp Leu Thr Phe Ala Ile Gly Gly Thr Gly
160                 165                 170                 175

ACG GGT AAC AGA AAT CAA GAG AAT GAC AAA GAC ACT CCA TAC AAT AAA    693
Thr Gly Asn Arg Asn Gln Glu Asn Asp Lys Asp Thr Pro Tyr Asn Lys
                180                 185                 190

ACA TAT CAA GGA ATC CTT TAT GGA ATT CAA GCA ACA TGG AAA CCA ATA    741
Thr Tyr Gln Gly Ile Leu Tyr Gly Ile Gln Ala Thr Trp Lys Pro Ile
            195                 200                 205

AAA AAT CTA CTT GAT CAA AAC GAA GAT ACT AAA TCT GTA ATT GCA GAA    789
Lys Asn Leu Leu Asp Gln Asn Glu Asp Thr Lys Ser Val Ile Ala Glu
        210                 215                 220

ACA CCT TTT GAA TTA AAT TTT GGC TTG TCA GGA GCC TAT GGA AAC GAG    837
Thr Pro Phe Glu Leu Asn Phe Gly Leu Ser Gly Ala Tyr Gly Asn Glu
    225                 230                 235

ACA TTC AAT AAT TCA TCA ATA ACA TAC TCT TTA AAA GAT AAA TCC GTA    885
Thr Phe Asn Asn Ser Ser Ile Thr Tyr Ser Leu Lys Asp Lys Ser Val
240                 245                 250                 255

GTT GGC AAC GAT TTA TTG AGC CCA ACT TTA TCA AAT TCT GCA ATT TTA    933
Val Gly Asn Asp Leu Leu Ser Pro Thr Leu Ser Asn Ser Ala Ile Leu
                260                 265                 270

GCA TCT TTT GGA GCT AAA TAT AAG CTT GGA TTA ACA AAA ATA AAC GAT    981
Ala Ser Phe Gly Ala Lys Tyr Lys Leu Gly Leu Thr Lys Ile Asn Asp
            275                 280                 285

AAA AAT ACC TAT CTT ATT TTG CAA ATG GGA ACT GAT TTT GGA ATA GAT   1029
Lys Asn Thr Tyr Leu Ile Leu Gln Met Gly Thr Asp Phe Gly Ile Asp
        290                 295                 300

CCT TTT GCA AGC GAT TTT TCT ATA TTT GGA CAC ATC TCA AAA GCA GCG   1077
Pro Phe Ala Ser Asp Phe Ser Ile Phe Gly His Ile Ser Lys Ala Ala
    305                 310                 315

AAT TTC AAA AAA GAA ACA CCC TCA GAT CCT AAC AAA AAA GCT GAA ATA   1125
Asn Phe Lys Lys Glu Thr Pro Ser Asp Pro Asn Lys Lys Ala Glu Ile
```

```
                                                            -continued 320                 325                 330                 335
TTT GAT CCA AAT GGC AAT GCT CTT AAT TTC AGC AAA AAC ACA GAA TTG        1173
Phe Asp Pro Asn Gly Asn Ala Leu Asn Phe Ser Lys Asn Thr Glu Leu
                340                 345                 350

GGC ATT GCA TTT TCA ACA GGA GCA AGT ATA GGT TTT GCT TGG AAT AAA        1221
Gly Ile Ala Phe Ser Thr Gly Ala Ser Ile Gly Phe Ala Trp Asn Lys
                355                 360                 365

GAT ACC GGT GAA AAA GAA TCC TGG GCG ATT AAA GGA TCT GAT TCC TAC        1269
Asp Thr Gly Glu Lys Glu Ser Trp Ala Ile Lys Gly Ser Asp Ser Tyr
                370                 375                 380

AGT ACA AGA CTC TTT GGA GAA CAA GAC AAA AAA TCT GGA GTT GCA TTG        1317
Ser Thr Arg Leu Phe Gly Glu Gln Asp Lys Lys Ser Gly Val Ala Leu
                385                 390                 395

GGA ATA AGC TAT GGA CAA AAC CTT TAC AGA TCT AAA GAT ACA GAA AAA        1365
Gly Ile Ser Tyr Gly Gln Asn Leu Tyr Arg Ser Lys Asp Thr Glu Lys
400                 405                 410                 415

AGA TTA AAA ACC ATA TCT GAA AAT GCA TTT CAA AGC TTA AAT GTT GAA        1413
Arg Leu Lys Thr Ile Ser Glu Asn Ala Phe Gln Ser Leu Asn Val Glu
                420                 425                 430

ATT TCA AGC TAT GAA GAC AAC AAA AAA GGG ATT ATA AAT GGA TTA GGA        1461
Ile Ser Ser Tyr Glu Asp Asn Lys Lys Gly Ile Ile Asn Gly Leu Gly
                435                 440                 445

TGG ATA ACA TCT ATC GGT CTT TAC GAT ATT TTA AGA CAA AAA TCT GTA        1509
Trp Ile Thr Ser Ile Gly Leu Tyr Asp Ile Leu Arg Gln Lys Ser Val
                450                 455                 460

GAA AAC TAT CCT ACA ACA ATT TCA AGC ACC ACT GAA AAC AAT CAA ACT        1557
Glu Asn Tyr Pro Thr Thr Ile Ser Ser Thr Thr Glu Asn Asn Gln Thr
465                 470                 475

GAA CAA AGT TCA ACA AGC ACA AAG ACC ACA ACC CCT AAT CTG ACA TTT        1605
Glu Gln Ser Ser Thr Ser Thr Lys Thr Thr Thr Pro Asn Leu Thr Phe
480                 485                 490                 495

GAA GAT GCA ATG AAA CTC GGC TTG GCC TTA TAT CTT GAT TAT GCA ATT        1653
Glu Asp Ala Met Lys Leu Gly Leu Ala Leu Tyr Leu Asp Tyr Ala Ile
                500                 505                 510

CCA ATA GCA TCC ATT TCA ACA GAA GCA TAT GTA GTA CCT TAC ATT GGA        1701
Pro Ile Ala Ser Ile Ser Thr Glu Ala Tyr Val Val Pro Tyr Ile Gly
                515                 520                 525

GCA TAC ATT TTA GGA CCT TCT AAT AAA CTC TCA AGC GAT GCT ACA AAA        1749
Ala Tyr Ile Leu Gly Pro Ser Asn Lys Leu Ser Ser Asp Ala Thr Lys
                530                 535                 540

ATT TAT TTA AAA ACA GGA CTT AGC CTT GAA AAA CTA ATA AGA TTT ACA        1797
Ile Tyr Leu Lys Thr Gly Leu Ser Leu Glu Lys Leu Ile Arg Phe Thr
                545                 550                 555

ACA ATT TCT CTT GGA TGG GAT TCA AAT AAC ATT ATA GAA CTT GCT AAT        1845
Thr Ile Ser Leu Gly Trp Asp Ser Asn Asn Ile Ile Glu Leu Ala Asn
560                 565                 570                 575

AAA AAC ACA AAT AAT GCT GCT ATT GGA AGT GCT TTC TTG CAA TTC AAA        1893
Lys Asn Thr Asn Asn Ala Ala Ile Gly Ser Ala Phe Leu Gln Phe Lys
                580                 585                 590

ATA GCC TAC AGC GGA AGC TAACAGCAAA AGAAGGGCTT TGGCCCTTCT               1941
Ile Ala Tyr Ser Gly Ser
                595

TTTTTATCTT TAAAAACAAT TGGGATTACC TTATATTTCT TTCCTTGCAA ATTTTTTCAT      2001

AAGCATCTTG AATTTTTATA AATTTATCAT TTGCATCTTT TTGTCTTACA GGATCATTTG      2061

CAAACTTATC AGGA                                                        2075

(2) INFORMATION FOR SEQ ID NO: 4:
```

(i) SEQUENCE CHARACTERISTICS:
    (A) LENGTH: 601 amino acids
    (B) TYPE: amino acid
    (D) TOPOLOGY: linear (ii) MOLECULE TYPE: protein (xi) SEQUENCE DESCRIPTION: SEQ ID NO: 4:

```
Ala Ile Phe Ala Ala Asp Ala Leu Lys Glu Lys Asp Ile Phe Lys Ile
 -4               1               5                   10

Asn Pro Trp Met Pro Thr Phe Gly Phe Glu Asn Thr Ser Glu Phe Arg
             15                  20                  25

Leu Asp Met Asp Glu Leu Val Pro Gly Phe Glu Asn Lys Ser Lys Ile
             30                  35                  40

Thr Ile Lys Leu Lys Pro Phe Glu Ala Asn Pro Glu Leu Gly Lys Asp
 45                  50                  55                  60

Asp Pro Phe Ser Ala Tyr Ile Lys Val Glu Asp Leu Ala Leu Lys Ala
                 65                  70                  75

Glu Gly Lys Lys Gly Asp Gln Phe Lys Ile Asp Val Gly Asp Ile Thr
             80                  85                  90

Ala Gln Ile Asn Met Tyr Asp Phe Phe Ile Lys Ile Ser Thr Met Thr
             95                 100                 105

Asp Phe Asp Phe Asn Lys Glu Ser Leu Phe Ser Phe Ala Pro Met Thr
110                 115                 120

Gly Phe Lys Ser Thr Tyr Tyr Gly Phe Pro Ser Asn Asp Arg Ala Val
125                 130                 135                 140

Arg Gly Thr Ile Leu Ala Arg Gly Thr Ser Lys Asn Ile Gly Thr Ile
                145                 150                 155

Gln Leu Gly Tyr Lys Leu Pro Lys Leu Asp Leu Thr Phe Ala Ile Gly
                160                 165                 170

Gly Thr Gly Thr Gly Asn Arg Asn Gln Glu Asn Asp Lys Asp Thr Pro
            175                 180                 185

Tyr Asn Lys Thr Tyr Gln Gly Ile Leu Tyr Gly Ile Gln Ala Thr Trp
    190                 195                 200

Lys Pro Ile Lys Asn Leu Leu Asp Gln Asn Glu Asp Thr Lys Ser Val
205                 210                 215                 220

Ile Ala Glu Thr Pro Phe Glu Leu Asn Phe Gly Leu Ser Gly Ala Tyr
                225                 230                 235

Gly Asn Glu Thr Phe Asn Asn Ser Ser Ile Thr Tyr Ser Leu Lys Asp
            240                 245                 250

Lys Ser Val Val Gly Asn Asp Leu Leu Ser Pro Thr Leu Ser Asn Ser
    255                 260                 265

Ala Ile Leu Ala Ser Phe Gly Ala Lys Tyr Lys Leu Gly Leu Thr Lys
270                 275                 280

Ile Asn Asp Lys Asn Thr Tyr Leu Ile Leu Gln Met Gly Thr Asp Phe
285                 290                 295                 300

Gly Ile Asp Pro Phe Ala Ser Asp Phe Ser Ile Phe Gly His Ile Ser
                305                 310                 315

Lys Ala Ala Asn Phe Lys Lys Glu Thr Pro Ser Asp Pro Asn Lys Lys
            320                 325                 330

Ala Glu Ile Phe Asp Pro Asn Gly Asn Ala Leu Asn Phe Ser Lys Asn
    335                 340                 345

Thr Glu Leu Gly Ile Ala Phe Ser Thr Gly Ala Ser Ile Gly Phe Ala
350                 355                 360

Trp Asn Lys Asp Thr Gly Glu Lys Glu Ser Trp Ala Ile Lys Gly Ser
```

-continued

```
365                 370                 375                 380

Asp Ser Tyr Ser Thr Arg Leu Phe Gly Glu Gln Asp Lys Lys Ser Gly
                385                 390                 395

Val Ala Leu Gly Ile Ser Tyr Gly Gln Asn Leu Tyr Arg Ser Lys Asp
            400                 405                 410

Thr Glu Lys Arg Leu Lys Thr Ile Ser Glu Asn Ala Phe Gln Ser Leu
        415                 420                 425

Asn Val Glu Ile Ser Ser Tyr Glu Asp Asn Lys Lys Gly Ile Ile Asn
    430                 435                 440

Gly Leu Gly Trp Ile Thr Ser Ile Gly Leu Tyr Asp Ile Leu Arg Gln
445                 450                 455                 460
Lys Ser Val Glu Asn Tyr Pro Thr Thr Ile Ser Ser Thr Thr Glu Asn
                465                 470                 475
Asn Gln Thr Glu Gln Ser Ser Thr Ser Thr Lys Thr Thr Thr Pro Asn
            480                 485                 490

Leu Thr Phe Glu Asp Ala Met Lys Leu Gly Leu Ala Leu Tyr Leu Asp
        495                 500                 505

Tyr Ala Ile Pro Ile Ala Ser Ile Ser Thr Glu Ala Tyr Val Val Pro
    510                 515                 520
Tyr Ile Gly Ala Tyr Ile Leu Gly Pro Ser Asn Lys Leu Ser Ser Asp
525                 530                 535                 540
Ala Thr Lys Ile Tyr Leu Lys Thr Gly Leu Ser Leu Glu Lys Leu Ile
                545                 550                 555
Arg Phe Thr Thr Ile Ser Leu Gly Trp Asp Ser Asn Asn Ile Ile Glu
            560                 565                 570

Leu Ala Asn Lys Asn Thr Asn Asn Ala Ala Ile Gly Ser Ala Phe Leu
        575                 580                 585

Gln Phe Lys Ile Ala Tyr Ser Gly Ser
    590                 595
```

(2) INFORMATION FOR SEQ ID NO: 5:

(i) SEQUENCE CHARACTERISTICS:
(A) LENGTH: 2264 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Borrelia afzelii
(B) STRAIN: ACAI (vii) IMMEDIATE SOURCE:
(B) CLONE: pJB-104

(ix) FEATURE:
(A) NAME/KEY: CDS
(B) LOCATION: 303..2162

(ix) FEATURE:
(A) NAME/KEY: sig_peptide
(B) LOCATION: 303..365

(ix) FEATURE:
(A) NAME/KEY: mat_peptide
(B) LOCATION: 366..2159

(xi) SEQUENCE DESCRIPTION: SEQ ID NO: 5:

```
TCAAAAACAA TAACTTACGC TTTATACTAC ATTCTAGCAA CAGGATTACT GGTTTATTTA      60

GTATAAATTA ATCATTTAAA ATAAATAAGA TTAGTTGACA ATACAATTAA TCTTATTTAT     120
```

```
AAATTTGAAT AGTATAAAAT CACAAATACC AATATGATAT TGAATTTTTA TCTAATAGTT       180

TTAATATTGT ATACATGTTA TTATGTACAA TAAGTAATAT GTATTATATA TATATTATTA       240

AGACGTTTAA AAAATAACTA AAACTAATAA AAAGTTTATA GTTACAACAG GAAGGTATAA       300

TT ATG AAA AAT CAT ATT TTA TAT AAA TTA ATT ATA TTT TTA ACC ACA         347
   Met Lys Asn His Ile Leu Tyr Lys Leu Ile Ile Phe Leu Thr Thr
   -21 -20              -15                     -10

TCT GCA GCA ATA TTT GCA GCA GAC GCA TTA AAG GAA AAA GAT ATA TTT         395
Ser Ala Ala Ile Phe Ala Ala Asp Ala Leu Lys Glu Lys Asp Ile Phe
    -5                  1               5                   10

AAA ATA AAC CCG TGG ATA CCG ACA TTT GGA TTT GAA AAC ACA AGT GAA         443
Lys Ile Asn Pro Trp Ile Pro Thr Phe Gly Phe Glu Asn Thr Ser Glu
                15                  20                  25

TTC AGA TTT GAT ATG GAT GAA CTT GTC CCT GGG TTT GAA AAC AAA AGT         491
Phe Arg Phe Asp Met Asp Glu Leu Val Pro Gly Phe Glu Asn Lys Ser
                30                  35                  40

AAA ATT ACT ATT AAA CTT AAA CCA TTT GAA ACT AAT CCA GAA TTA GGC         539
Lys Ile Thr Ile Lys Leu Lys Pro Phe Glu Thr Asn Pro Glu Leu Gly
            45                  50                  55

AAA GAC GAT CCA TTT TCA GCT TAC ATT AAA GTG GAA GAT CTT GCA TTA         587
Lys Asp Asp Pro Phe Ser Ala Tyr Ile Lys Val Glu Asp Leu Ala Leu
        60                  65                  70

AAA GCA GAA GGC AAA AAA GAC GCT CAA TTC AAA ATC GAT GTA GGA GAT         635
Lys Ala Glu Gly Lys Lys Asp Ala Gln Phe Lys Ile Asp Val Gly Asp
75              80                  85                  90

ATA ACA GCC CAA ATT AAT ATA TAC GAT TTT TTT ATT AAA ATA AGT ACT         683
Ile Thr Ala Gln Ile Asn Ile Tyr Asp Phe Phe Ile Lys Ile Ser Thr
                95                  100                 105

ATG ACG GAT TTT GAC TTT AAT AAA GAA TCT TTA TTT AGC TTT GCG CCT         731
Met Thr Asp Phe Asp Phe Asn Lys Glu Ser Leu Phe Ser Phe Ala Pro
            110                 115                 120

ATG ACT GGA TTC AAA AGC ACT TAC TAT GGA TTC CCA AGT AAT GAT AGA         779
Met Thr Gly Phe Lys Ser Thr Tyr Tyr Gly Phe Pro Ser Asn Asp Arg
        125                 130                 135

GCA GTA AGA GGG ACA ATT CTT GCA AGA GGT ACT TCT AAA AAC ATA GGA         827
Ala Val Arg Gly Thr Ile Leu Ala Arg Gly Thr Ser Lys Asn Ile Gly
140                 145                 150

ACA ATT CAA CTG GGA TAC AAA CTC CCA CAA ATC GAC CTT ACA TTT GCA         875
Thr Ile Gln Leu Gly Tyr Lys Leu Pro Gln Ile Asp Leu Thr Phe Ala
155                 160                 165                 170

ATA GGA GGA ACA GGC ACA GGT AAT AGA AAT CAA GAG AAT GAC AAA GAC         923
Ile Gly Gly Thr Gly Thr Gly Asn Arg Asn Gln Glu Asn Asp Lys Asp
                175                 180                 185

ACT CCA TAC AAT AAA ACC TAT CAA GGA ATC CTT TAT GGA ATT CAA GCA         971
Thr Pro Tyr Asn Lys Thr Tyr Gln Gly Ile Leu Tyr Gly Ile Gln Ala
            190                 195                 200

ACA TGG AAG CCA ATA AAA AAT ATA CTT GAT CAA AAC GAA GAT ACT CAA        1019
Thr Trp Lys Pro Ile Lys Asn Ile Leu Asp Gln Asn Glu Asp Thr Gln
        205                 210                 215

TCT GTA ATT GCA GAA ACA CCT TTT GAA TTA AAC TTT GGC TTA TCA GGA        1067
Ser Val Ile Ala Glu Thr Pro Phe Glu Leu Asn Phe Gly Leu Ser Gly
        220                 225                 230

GCT TAT GGA AAT GAA ACA TTC AAT AAT TCA TCA ATA ACA TAC TCT TTA        1115
Ala Tyr Gly Asn Glu Thr Phe Asn Asn Ser Ser Ile Thr Tyr Ser Leu
235                 240                 245                 250

AAA GAT AAA TCC CTA ATT GGT AAC GAT TTA TTA AGC CCA ACT TTA TCA        1163
Lys Asp Lys Ser Leu Ile Gly Asn Asp Leu Leu Ser Pro Thr Leu Ser
                255                 260                 265
```

```
AAT TCT GCA ATT TTG GCA TCT TTT GGA GCT CAA TAT AAG CTT GGA TTA    1211
Asn Ser Ala Ile Leu Ala Ser Phe Gly Ala Gln Tyr Lys Leu Gly Leu
        270                 275                 280

ACA AAA ATC AAT AAT AAA AAT ACC TAT CTT ATT TTA CAA ATG GGT ACT    1259
Thr Lys Ile Asn Asn Lys Asn Thr Tyr Leu Ile Leu Gln Met Gly Thr
            285                 290                 295

GAT TTT GGA ATA GAT CCT TTT GCA AGC GAT TTT TCT GTA TTT GGA CAC    1307
Asp Phe Gly Ile Asp Pro Phe Ala Ser Asp Phe Ser Val Phe Gly His
300                 305                 310

ATC TCA AAA GCA GCA AAT TTG AAA AAA GGA ATA TCT TTA GAT CCT AGT    1355
Ile Ser Lys Ala Ala Asn Leu Lys Lys Gly Ile Ser Leu Asp Pro Ser
315                 320                 325                 330

AAA AAA GCC GAG GAT ATA TTT GAT CCA AAT GGC AAT GCC CTT AAT TTC    1403
Lys Lys Ala Glu Asp Ile Phe Asp Pro Asn Gly Asn Ala Leu Asn Phe
                335                 340                 345

AAT AAA AAT ACA GAA CTA GGC ATT GCA TTT TCA ACA GGA GCA AGC ATA    1451
Asn Lys Asn Thr Glu Leu Gly Ile Ala Phe Ser Thr Gly Ala Ser Ile
            350                 355                 360

GGG CTT GCT TGG AAT AAA GAC GAC GGT GAA AAA GAA TCT TGG AAA GTT    1499
Gly Leu Ala Trp Asn Lys Asp Asp Gly Glu Lys Glu Ser Trp Lys Val
        365                 370                 375

AAA GGA TCT GAT TCC TAC AGT ACA AGA CTA TTT GGA GAA CAA GAC AAA    1547
Lys Gly Ser Asp Ser Tyr Ser Thr Arg Leu Phe Gly Glu Gln Asp Lys
380                 385                 390

AAA TCT GGA GTT GCA TTA GGA ATA AGC TAT GGG CAA AAT CTT TAC AGA    1595
Lys Ser Gly Val Ala Leu Gly Ile Ser Tyr Gly Gln Asn Leu Tyr Arg
395                 400                 405                 410

TCT AAA GAT ACA GAA AAA AGA TTA AAA ACC ATA TCT GAA AAT GCA TTT    1643
Ser Lys Asp Thr Glu Lys Arg Leu Lys Thr Ile Ser Glu Asn Ala Phe
                415                 420                 425

CAA AGC TTA AAT GTT GAA ATT TCA AGC TAT GAA GAC AAT AAA AAG GGG    1691
Gln Ser Leu Asn Val Glu Ile Ser Ser Tyr Glu Asp Asn Lys Lys Gly
            430                 435                 440

CTT ATG AAT GGA CTG GGT TGG ATA ACA TCT ATC GGT CTT TAT GAT ATT    1739
Leu Met Asn Gly Leu Gly Trp Ile Thr Ser Ile Gly Leu Tyr Asp Ile
        445                 450                 455

TTA AGA CAA AAA TCT GTA GAA AAC TAT CCT ACA TCA ACC TTA AGT GCT    1787
Leu Arg Gln Lys Ser Val Glu Asn Tyr Pro Thr Ser Thr Leu Ser Ala
460                 465                 470

AAT GAG AAC AAT CAA GCT GGA CAA AGT TCA ACA GGC ACA CAA GCC ATA    1835
Asn Glu Asn Asn Gln Ala Gly Gln Ser Ser Thr Gly Thr Gln Ala Ile
475                 480                 485                 490

ACA CCT AAT CTA ACA TTT GAA GAC GCA ATG AAA CTA GGC ATA GCT TTA    1883
Thr Pro Asn Leu Thr Phe Glu Asp Ala Met Lys Leu Gly Ile Ala Leu
                495                 500                 505

TAT CTT GAT TAT GCA ATT CCA ATA GAA TCC ATT TCA ACA GAA GCA TAT    1931
Tyr Leu Asp Tyr Ala Ile Pro Ile Glu Ser Ile Ser Thr Glu Ala Tyr
            510                 515                 520

GTA GTA CCA TAT ATT GGA GCA TAC CTT TTA GGA CCT TCT AAT AAA ATA    1979
Val Val Pro Tyr Ile Gly Ala Tyr Leu Leu Gly Pro Ser Asn Lys Ile
        525                 530                 535

TCA AGC GAT GCT ACA AAA ATT TAT TTA AAA ACA GGA CTT AGT CTT GAA    2027
Ser Ser Asp Ala Thr Lys Ile Tyr Leu Lys Thr Gly Leu Ser Leu Glu
540                 545                 550

AAA CTA ATA AGA TTT ACA ACA ATT TCT CTT GGA TGG GAT TCA AAT AAT    2075
Lys Leu Ile Arg Phe Thr Thr Ile Ser Leu Gly Trp Asp Ser Asn Asn
555                 560                 565                 570

ATT ATA GAA CTT GCT AAT AAA AAC GCA AAT AAT GCT GCT ATT GGC AGT    2123
Ile Ile Glu Leu Ala Asn Lys Asn Ala Asn Asn Ala Ala Ile Gly Ser
                575                 580                 585
```

```
GCT TTC TTG CAA TTC AAA ATA GCC TAC AGC GGA AGC TAACAGCAAA          2169
Ala Phe Leu Gln Phe Lys Ile Ala Tyr Ser Gly Ser
            590                 595

AGAAGGGCCA AAAGCCCTTC TTTTTTATCT TTAAAAACAA ATTAATCAAT TAATTACTTA   2229

ATATTTCTTT CTTTGCAAAT CTTTTCATAA GCATC                              2264
```

(2) INFORMATION FOR SEQ ID NO: 6:

(i) SEQUENCE CHARACTERISTICS:
        (A) LENGTH: 619 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Asn His Ile Leu Tyr Lys Leu Ile Ile Phe Leu Thr Thr Ser
-21 -20              -15                 -10

Ala Ala Ile Phe Ala Ala Asp Ala Leu Lys Glu Lys Asp Ile Phe Lys
 -5              1               5                  10

Ile Asn Pro Trp Ile Pro Thr Phe Gly Phe Glu Asn Thr Ser Glu Phe
             15                  20                 25

Arg Phe Asp Met Asp Glu Leu Val Pro Gly Phe Glu Asn Lys Ser Lys
         30                  35                 40

Ile Thr Ile Lys Leu Lys Pro Phe Glu Thr Asn Pro Glu Leu Gly Lys
     45                  50                 55

Asp Asp Pro Phe Ser Ala Tyr Ile Lys Val Glu Asp Leu Ala Leu Lys
 60              65                  70                 75

Ala Glu Gly Lys Lys Asp Ala Gln Phe Lys Ile Asp Val Gly Asp Ile
             80                  85                 90

Thr Ala Gln Ile Asn Ile Tyr Asp Phe Phe Ile Lys Ile Ser Thr Met
             95                  100                105

Thr Asp Phe Asp Phe Asn Lys Glu Ser Leu Phe Ser Phe Ala Pro Met
         110                 115                120

Thr Gly Phe Lys Ser Thr Tyr Tyr Gly Phe Pro Ser Asn Asp Arg Ala
         125                 130                 135

Val Arg Gly Thr Ile Leu Ala Arg Gly Thr Ser Lys Asn Ile Gly Thr
140                 145                 150                155

Ile Gln Leu Gly Tyr Lys Leu Pro Gln Ile Asp Leu Thr Phe Ala Ile
             160                 165                170

Gly Gly Thr Gly Thr Gly Asn Arg Asn Gln Glu Asn Asp Lys Asp Thr
             175                 180                 185

Pro Tyr Asn Lys Thr Tyr Gln Gly Ile Leu Tyr Gly Ile Gln Ala Thr
             190                 195                 200

Trp Lys Pro Ile Lys Asn Ile Leu Asp Gln Asn Glu Asp Thr Gln Ser
     205                 210                 215

Val Ile Ala Glu Thr Pro Phe Glu Leu Asn Phe Gly Leu Ser Gly Ala
220                 225                 230                 235

Tyr Gly Asn Glu Thr Phe Asn Asn Ser Ser Ile Thr Tyr Ser Leu Lys
                 240                 245                 250

Asp Lys Ser Leu Ile Gly Asn Asp Leu Leu Ser Pro Thr Leu Ser Asn
             255                 260                 265

Ser Ala Ile Leu Ala Ser Phe Gly Ala Gln Tyr Lys Leu Gly Leu Thr
             270                 275                 280

Lys Ile Asn Asn Lys Asn Thr Tyr Leu Ile Leu Gln Met Gly Thr Asp
```

```
                285                   290                    295
Phe Gly Ile Asp Pro Phe Ala Ser Asp Phe Ser Val Phe Gly His Ile
300                 305                 310                 315

Ser Lys Ala Ala Asn Leu Lys Lys Gly Ile Ser Leu Asp Pro Ser Lys
                320                 325                 330

Lys Ala Glu Asp Ile Phe Asp Pro Asn Gly Asn Ala Leu Asn Phe Asn
                335                 340                 345

Lys Asn Thr Glu Leu Gly Ile Ala Phe Ser Thr Gly Ala Ser Ile Gly
                350                 355                 360

Leu Ala Trp Asn Lys Asp Asp Gly Glu Lys Glu Ser Trp Lys Val Lys
                365                 370                 375

Gly Ser Asp Ser Tyr Ser Thr Arg Leu Phe Gly Glu Gln Asp Lys Lys
380                 385                 390                 395

Ser Gly Val Ala Leu Gly Ile Ser Tyr Gly Gln Asn Leu Tyr Arg Ser
                400                 405                 410

Lys Asp Thr Glu Lys Arg Leu Lys Thr Ile Ser Glu Asn Ala Phe Gln
                415                 420                 425

Ser Leu Asn Val Glu Ile Ser Ser Tyr Glu Asp Asn Lys Lys Gly Leu
                430                 435                 440

Met Asn Gly Leu Gly Trp Ile Thr Ser Ile Gly Leu Tyr Asp Ile Leu
445                 450                 455

Arg Gln Lys Ser Val Glu Asn Tyr Pro Thr Ser Thr Leu Ser Ala Asn
460                 465                 470                 475

Glu Asn Asn Gln Ala Gly Gln Ser Ser Thr Gly Thr Gln Ala Ile Thr
                480                 485                 490

Pro Asn Leu Thr Phe Glu Asp Ala Met Lys Leu Gly Ile Ala Leu Tyr
                495                 500                 505

Leu Asp Tyr Ala Ile Pro Ile Glu Ser Ile Ser Thr Glu Ala Tyr Val
                510                 515                 520

Val Pro Tyr Ile Gly Ala Tyr Leu Leu Gly Pro Ser Asn Lys Ile Ser
525                 530                 535

Ser Asp Ala Thr Lys Ile Tyr Leu Lys Thr Gly Leu Ser Leu Glu Lys
540                 545                 550                 555

Leu Ile Arg Phe Thr Thr Ile Ser Leu Gly Trp Asp Ser Asn Asn Ile
                560                 565                 570

Ile Glu Leu Ala Asn Lys Asn Ala Asn Asn Ala Ala Ile Gly Ser Ala
                575                 580                 585

Phe Leu Gln Phe Lys Ile Ala Tyr Ser Gly Ser
                590                 595

(2) INFORMATION FOR SEQ ID NO: 7:

(i) SEQUENCE CHARACTERISTICS:
        (A) LENGTH: 2547 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrlia garinii
        (B) STRAIN: Ip90

(vii) IMMEDIATE SOURCE:
        (B) CLONE: pJB-101

(ix) FEATURE:
        (A) NAME/KEY: CDS
```

-continued

```
    (B) LOCATION: 380..2245

(ix) FEATURE:
    (A) NAME/KEY: sig_peptide
    (B) LOCATION: 380..442

(ix) FEATURE:
    (A) NAME/KEY: mat_peptide
    (B) LOCATION: 443..2242

(xi) SEQUENCE DESCRIPTION: SEQ ID NO: 7:
```

```
AAGCTTTTGT CAAAAACAAT ACCTTACGCT TTATACTACA TTCTAGCAAC AGGATTGCTA      60

GTTTATTTAG TATAAATTAA TCATTTAAAA TAAATAAGAT TAATTTACAA TAAAATTAAT     120

CTTATTTATA GATTTGAATA ATATAAAAAT CATAAAATAA TAATATGATC TTGAATTTTT     180

ACCTAATATT TTAATATTAT ATACATGTTA TATATATATT ATTATATGCA TAATAGCATG     240

TATATAATAT ATTTTAGCAT AATAGCATGT ATATAATATA TTTTAGCATA ATAGCATGTA     300

TATAATATAT TTTATTAATG CGTTTAATAA ATAACTAGAA CTAATAAAAA GTTTATAGTT     360

ACAACAGGAA GGTATAATT ATG AAA AAT CAT ATT TTA TAT AAA TTA ATT ATA      412
                     Met Lys Asn His Ile Leu Tyr Lys Leu Ile Ile
                     -21 -20                  -15

TTT TTA ACT ACA TCT GTA GCA ATA TTT GCA GCA GCA GAT AAA TTA AAG       460
Phe Leu Thr Thr Ser Val Ala Ile Phe Ala Ala Ala Asp Lys Leu Lys
-10              -5                   1                5

GAA GAA GAT ATA TTT AAA ATA AAT CCA TGG ATA CCT ACA TTT GGA ATT       508
Glu Glu Asp Ile Phe Lys Ile Asn Pro Trp Ile Pro Thr Phe Gly Ile
             10                  15                  20

GAA AAC ACA AGT GAG TTC AGA CTT GAT ATG GAT GAG CTT GTT CCT GGA       556
Glu Asn Thr Ser Glu Phe Arg Leu Asp Met Asp Glu Leu Val Pro Gly
         25                  30                  35

TTT GAA AAC AAA AGC AAA ATT ACT ATT AAA CTT AAA CCA TTT GAA GTT       604
Phe Glu Asn Lys Ser Lys Ile Thr Ile Lys Leu Lys Pro Phe Glu Val
     40                  45                  50

AAT CCC GAA TTA GGC AAA GAC GAC CCA TTC TCA GCT TAC ATT AAG GTA       652
Asn Pro Glu Leu Gly Lys Asp Asp Pro Phe Ser Ala Tyr Ile Lys Val
 55                  60                  65                  70

GAA GAT CTT GCA TTA AAA GCG GAA GGT AAA AAA GGG GAT CCA TTT AAA       700
Glu Asp Leu Ala Leu Lys Ala Glu Gly Lys Lys Gly Asp Pro Phe Lys
                 75                  80                  85

ATT GAC GTA GGA GAC ATA ACA GCC CAA ATT AAT ATA TAC GAT TTT TTT       748
Ile Asp Val Gly Asp Ile Thr Ala Gln Ile Asn Ile Tyr Asp Phe Phe
             90                  95                 100

ATT AAG ATA AGC ACT ATG ACA GAT TTT GAC TTT AAT AAA GAA TCT TTA       796
Ile Lys Ile Ser Thr Met Thr Asp Phe Asp Phe Asn Lys Glu Ser Leu
         105                 110                 115

TTT AGT TTT GCG CCC ATG ACC GGA TTC AAA AGC ACT TAC TAC GGA TTT       844
Phe Ser Phe Ala Pro Met Thr Gly Phe Lys Ser Thr Tyr Tyr Gly Phe
     120                 125                 130

CCA AGC AAA GAC AGA ATA GTA AGA GGA ACA ATT CTT GCA AGA GGT GCT       892
Pro Ser Lys Asp Arg Ile Val Arg Gly Thr Ile Leu Ala Arg Gly Ala
135                 140                 145                 150

TCT AAA AAC ATA GGA ACA ATT CAA ATG GGA TAC AAG CTC CCA CAA ATA       940
Ser Lys Asn Ile Gly Thr Ile Gln Met Gly Tyr Lys Leu Pro Gln Ile
                 155                 160                 165

GAC CTT ACA TTT GCA ATA GGG GGA ACA GGC ACA GGT AAC AGA AAT CAA       988
Asp Leu Thr Phe Ala Ile Gly Gly Thr Gly Thr Gly Asn Arg Asn Gln
             170                 175                 180

GAG AAT GAC AAA GAC ACT CCA TAC AAT AAA ACC TAT AAA GGA ATA CTT      1036
Glu Asn Asp Lys Asp Thr Pro Tyr Asn Lys Thr Tyr Lys Gly Ile Leu
         185                 190                 195
```

```
TAT GGG GTT CAA GCA ACA TGG AAG CCA ATA AAA AAT CTA CTT GAT AAA      1084
Tyr Gly Val Gln Ala Thr Trp Lys Pro Ile Lys Asn Leu Leu Asp Lys
    200                 205                 210

AAC GAA GAT AAT CGA TCT GTA ATT GCA GAA ACA CCT TTT GAA TTA AAT      1132
Asn Glu Asp Asn Arg Ser Val Ile Ala Glu Thr Pro Phe Glu Leu Asn
215                 220                 225                 230

TTT GGC TTA TCA GGA GCT TAT GGA AAT AAA ACA TTC AAT AAT TCA TCA      1180
Phe Gly Leu Ser Gly Ala Tyr Gly Asn Lys Thr Phe Asn Asn Ser Ser
                235                 240                 245

ATA ACA TAC TCT TTA AAA GAT AAA TCT GTA GTT GGT AAC GAT TTA TTG      1228
Ile Thr Tyr Ser Leu Lys Asp Lys Ser Val Val Gly Asn Asp Leu Leu
            250                 255                 260

AGT CCA ACT TTA TCA AAT TCT GCA ATT TTA GCA TCT TTT GGA GCT CAA      1276
Ser Pro Thr Leu Ser Asn Ser Ala Ile Leu Ala Ser Phe Gly Ala Gln
        265                 270                 275

TAT AAG CTT GGA TTA ACA AAA ATC AAC AAT AAA AAT ACC TAT CTT ATT      1324
Tyr Lys Leu Gly Leu Thr Lys Ile Asn Asn Lys Asn Thr Tyr Leu Ile
    280                 285                 290

TTA CAA ATG GGT ACC GAT TTT GGA ATA GAT CCT TTT GCA AGC GAT TTT      1372
Leu Gln Met Gly Thr Asp Phe Gly Ile Asp Pro Phe Ala Ser Asp Phe
295                 300                 305                 310

TCT GTA TTT GGA CAC ATC TCA AAA GCA GCA AAT TCT AAA AAA GGA ATA      1420
Ser Val Phe Gly His Ile Ser Lys Ala Ala Asn Ser Lys Lys Gly Ile
                315                 320                 325

TCC GTA GAT CCT ATT AAA AAA GCC GAA GAT ATA TTT GAT CCA AAT GGC      1468
Ser Val Asp Pro Ile Lys Lys Ala Glu Asp Ile Phe Asp Pro Asn Gly
            330                 335                 340

AAT GCT CTT AAT TTC AGT AAA AAT ACA GAG CTG GGC ATT GCA TTT TCA      1516
Asn Ala Leu Asn Phe Ser Lys Asn Thr Glu Leu Gly Ile Ala Phe Ser
        345                 350                 355

ACA GGA GCA AGC ATA GGG CTT CTC TGG AAT AAA GAC GAC GGT GAA AAA      1564
Thr Gly Ala Ser Ile Gly Leu Leu Trp Asn Lys Asp Asp Gly Glu Lys
    360                 365                 370

GAA TCT TGG AAG GTT AAG GGA GCT GAT TCC TAC AGT ACA AGA CTA TTT      1612
Glu Ser Trp Lys Val Lys Gly Ala Asp Ser Tyr Ser Thr Arg Leu Phe
375                 380                 385                 390

GGA GAA CAA GAC AAA AAA TCT GGA GTT GCA TTA GGA ATA AGT TAT GGA      1660
Gly Glu Gln Asp Lys Lys Ser Gly Val Ala Leu Gly Ile Ser Tyr Gly
                395                 400                 405

CAA AAT CTT TAT AGA TCC AAA GAT ACA GAA AAA AGA TTA AAA ACC ATA      1708
Gln Asn Leu Tyr Arg Ser Lys Asp Thr Glu Lys Arg Leu Lys Thr Ile
            410                 415                 420

TCC GAA AAT GCA TTT CAA AGC TTA AAT GTT GAA ATC TCA AGC TAT GAA      1756
Ser Glu Asn Ala Phe Gln Ser Leu Asn Val Glu Ile Ser Ser Tyr Glu
        425                 430                 435

GAC AAC AAA AAA GGA CTT ATG AAC GGA CTA GGA TGG ATA ACA TCT ATC      1804
Asp Asn Lys Lys Gly Leu Met Asn Gly Leu Gly Trp Ile Thr Ser Ile
    440                 445                 450

GGT CTT TAT GAT ATT TTA AGA CAA AAA TCT GTA GAA AAC TAT CCC ACA      1852
Gly Leu Tyr Asp Ile Leu Arg Gln Lys Ser Val Glu Asn Tyr Pro Thr
455                 460                 465                 470

ACA ACA AGC TCA GCT GCT GAT GCA AAC AAT CAA GCC GGA CAA AGT TCA      1900
Thr Thr Ser Ser Ala Ala Asp Ala Asn Asn Gln Ala Gly Gln Ser Ser
                475                 480                 485

GGA AGC ACA CAA GCT ACA ACC CCT AAT CTA ACA TTT GAA GAC GCA ATG      1948
Gly Ser Thr Gln Ala Thr Thr Pro Asn Leu Thr Phe Glu Asp Ala Met
            490                 495                 500

AAA CTC GGT ATA GCT TTA TAT CTT GAT TAT GCA ATT CCA ATA GAA TCC      1996
Lys Leu Gly Ile Ala Leu Tyr Leu Asp Tyr Ala Ile Pro Ile Glu Ser
```

-continued

```
           505                 510                515
ATT TCA ACA GAA GCA TAT GTA GTA CCT TAT ATT GGG GCA TAC CTT TTA    2044
Ile Ser Thr Glu Ala Tyr Val Val Pro Tyr Ile Gly Ala Tyr Leu Leu
    520                 525                530

GGG CAT TTT AAT AAA ATC TCA AGC GAT GCT ACA AAA ATT TAT TTA AAG    2092
Gly His Phe Asn Lys Ile Ser Ser Asp Ala Thr Lys Ile Tyr Leu Lys
535                 540                545                550

ACA GGA CTT AGT CTT GAA AAA CTA ATA AGA TTT ACA ACA ATT TCT CTT    2140
Thr Gly Leu Ser Leu Glu Lys Leu Ile Arg Phe Thr Thr Ile Ser Leu
                555                560                565

GGC TGG GAT TCA AAT AAC ATT ATA GAA CTT GCT AAT AAA AAC ACA AAT    2188
Gly Trp Asp Ser Asn Asn Ile Ile Glu Leu Ala Asn Lys Asn Thr Asn
            570                575                580

AAT GCT GCC ATT GGT AGT GCT TTC TTG CAA TTC AAA ATA GCC TAC AGT    2236
Asn Ala Ala Ile Gly Ser Ala Phe Leu Gln Phe Lys Ile Ala Tyr Ser
        585                590                595

GGA AGC TAAAAGCAAA AGAAGGGCTT TAGGCCCTTC TTTTTTTATC TTTAAAAACA    2292
Gly Ser
    600

AATTAATATT AATTACTTTA TATTTCTTTC TTTGCAAATC TTTTCATAAG CATCTTGAAT    2352

TTTAATAAAT TTATCATTTG CATCTTTTTG CCTTACAGGA TCATTTGCAA ACCTGTCAGG    2412

ATGATATTTT ATAACAAGAC TTTTATAAGC CTTTTTAATC TCATCATCAC TAGCACTATA    2472

GACTAACCCC AAAACACTAT AGGGATTTAC AATTTTAATA TTAATATCTT TATAAGCTTC    2532

ATAACCATCA GATTC    2547
```

(2) INFORMATION FOR SEQ ID NO: 8:

(i) SEQUENCE CHARACTERISTICS:
        (A) LENGTH: 621 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Lys Asn His Ile Leu Tyr Lys Leu Ile Ile Phe Leu Thr Thr Ser
-21 -20                 -15                -10

Val Ala Ile Phe Ala Ala Ala Asp Lys Leu Lys Glu Glu Asp Ile Phe
-5                  1                  5                  10

Lys Ile Asn Pro Trp Ile Pro Thr Phe Gly Ile Glu Asn Thr Ser Glu
                15                 20                 25

Phe Arg Leu Asp Met Asp Glu Leu Val Pro Gly Phe Glu Asn Lys Ser
            30                 35                 40

Lys Ile Thr Ile Lys Leu Lys Pro Phe Glu Val Asn Pro Glu Leu Gly
        45                 50                 55

Lys Asp Asp Pro Phe Ser Ala Tyr Ile Lys Val Glu Asp Leu Ala Leu
60                 65                 70                 75

Lys Ala Glu Gly Lys Lys Gly Asp Pro Phe Lys Ile Asp Val Gly Asp
                80                 85                 90

Ile Thr Ala Gln Ile Asn Ile Tyr Asp Phe Phe Ile Lys Ile Ser Thr
            95                 100                105

Met Thr Asp Phe Asp Phe Asn Lys Glu Ser Leu Phe Ser Phe Ala Pro
        110                115                120

Met Thr Gly Phe Lys Ser Thr Tyr Tyr Gly Phe Pro Ser Lys Asp Arg
    125                130                135

Ile Val Arg Gly Thr Ile Leu Ala Arg Gly Ala Ser Lys Asn Ile Gly
```

-continued

```
140                 145                 150                 155
Thr Ile Gln Met Gly Tyr Lys Leu Pro Gln Ile Asp Leu Thr Phe Ala
                160                 165                 170
Ile Gly Gly Thr Gly Thr Gly Asn Arg Asn Gln Glu Asn Asp Lys Asp
                175                 180                 185
Thr Pro Tyr Asn Lys Thr Tyr Lys Gly Ile Leu Tyr Gly Val Gln Ala
                190                 195                 200
Thr Trp Lys Pro Ile Lys Asn Leu Leu Asp Lys Asn Glu Asp Asn Arg
                205                 210                 215
Ser Val Ile Ala Glu Thr Pro Phe Glu Leu Asn Phe Gly Leu Ser Gly
220                 225                 230                 235
Ala Tyr Gly Asn Lys Thr Phe Asn Asn Ser Ser Ile Thr Tyr Ser Leu
                240                 245                 250
Lys Asp Lys Ser Val Val Gly Asn Asp Leu Leu Ser Pro Thr Leu Ser
                255                 260                 265
Asn Ser Ala Ile Leu Ala Ser Phe Gly Ala Gln Tyr Lys Leu Gly Leu
                270                 275                 280
Thr Lys Ile Asn Asn Lys Asn Thr Tyr Leu Ile Leu Gln Met Gly Thr
                285                 290                 295
Asp Phe Gly Ile Asp Pro Phe Ala Ser Asp Phe Ser Val Phe Gly His
300                 305                 310                 315
Ile Ser Lys Ala Ala Asn Ser Lys Lys Gly Ile Ser Val Asp Pro Ile
                320                 325                 330
Lys Lys Ala Glu Asp Ile Phe Asp Pro Asn Gly Asn Ala Leu Asn Phe
                335                 340                 345
Ser Lys Asn Thr Glu Leu Gly Ile Ala Phe Ser Thr Gly Ala Ser Ile
                350                 355                 360
Gly Leu Leu Trp Asn Lys Asp Asp Gly Glu Lys Glu Ser Trp Lys Val
                365                 370                 375
Lys Gly Ala Asp Ser Tyr Ser Thr Arg Leu Phe Gly Glu Gln Asp Lys
380                 385                 390                 395
Lys Ser Gly Val Ala Leu Gly Ile Ser Tyr Gly Gln Asn Leu Tyr Arg
                400                 405                 410
Ser Lys Asp Thr Glu Lys Arg Leu Lys Thr Ile Ser Glu Asn Ala Phe
                415                 420                 425
Gln Ser Leu Asn Val Glu Ile Ser Ser Tyr Glu Asp Asn Lys Lys Gly
                430                 435                 440
Leu Met Asn Gly Leu Gly Trp Ile Thr Ser Ile Gly Leu Tyr Asp Ile
                445                 450                 455
Leu Arg Gln Lys Ser Val Glu Asn Tyr Pro Thr Thr Thr Ser Ser Ala
460                 465                 470                 475
Ala Asp Ala Asn Asn Gln Ala Gly Gln Ser Ser Gly Ser Thr Gln Ala
                480                 485                 490
Thr Thr Pro Asn Leu Thr Phe Glu Asp Ala Met Lys Leu Gly Ile Ala
                495                 500                 505
Leu Tyr Leu Asp Tyr Ala Ile Pro Ile Glu Ser Ile Ser Thr Glu Ala
                510                 515                 520
Tyr Val Val Pro Tyr Ile Gly Ala Tyr Leu Leu Gly His Phe Asn Lys
                525                 530                 535
Ile Ser Ser Asp Ala Thr Lys Ile Tyr Leu Lys Thr Gly Leu Ser Leu
540                 545                 550                 555
Glu Lys Leu Ile Arg Phe Thr Thr Ile Ser Leu Gly Trp Asp Ser Asn
                560                 565                 570
```

```
Asn Ile Ile Glu Leu Ala Asn Lys Asn Thr Asn Asn Ala Ala Ile Gly
        575                 580                 585

Ser Ala Phe Leu Gln Phe Lys Ile Ala Tyr Ser Gly Ser
        590                 595                 600
```

(2) INFORMATION FOR SEQ ID NO: 9:

(i) SEQUENCE CHARACTERISTICS:
        (A) LENGTH: 64 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrlia burgdorferi
        (B) STRAIN: B31

(vii) IMMEDIATE SOURCE:
        (B) CLONE: pJB-105

(ix) FEATURE:
        (A) NAME/KEY: CDS
        (B) LOCATION: 14..61

(ix) FEATURE:
        (A) NAME/KEY: sig_peptide
        (B) LOCATION: 14..61
        (D) OTHER INFORMATION: /partial
            /label= partial (xi) SEQUENCE DESCRIPTION: SEQ ID NO: 9:

```
GGAGGGTATA ATT ATG AAA AGC CAT ATT TTA TAT AAA TTA ATC ATA TTT           49
           Met Lys Ser His Ile Leu Tyr Lys Leu Ile Ile Phe
            1               5                  10

TTA ACC ACA TCT GCA                                                      64
Leu Thr Thr Ser
        15
```

(2) INFORMATION FOR SEQ ID NO: 10:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Lys Ser His Ile Leu Tyr Lys Leu Ile Ile Phe Leu Thr Thr Ser
 1               5                  10                  15
```

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

```
GCAATATTTG CTGCAGCAGA T                                                  21
```

(2) INFORMATION FOR SEQ ID NO: 12:

(i) SEQUENCE CHARACTERISTICS:

```
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GGCCTAAAGG AATTCTTTTG C                                              21

(2) INFORMATION FOR SEQ ID NO: 13:

(i) SEQUENCE CHARACTERISTICS:
        (A) LENGTH: 2031 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia burgdorferi
        (B) STRAIN: B31

(ix) FEATURE:
        (A) NAME/KEY: CDS
        (B) LOCATION: 14..1870

(ix) FEATURE:
        (A) NAME/KEY: sig_peptide
        (B) LOCATION: 14..76

(ix) FEATURE:
        (A) NAME/KEY: mat_peptide
        (B) LOCATION: 77..1867

(xi) SEQUENCE DESCRIPTION: SEQ ID NO: 13:

GGAGGGTATA ATT ATG AAA AGC CAT ATT TTA TAT AAA TTA ATC ATA TTT            49
            Met Lys Ser His Ile Leu Tyr Lys Leu Ile Ile Phe
            -21 -20             -15                 -10

TTA ACC ACA TCT GCA GCA ATA TTT GCA GCA GAC GCA TTA AAG GAA AAA          97
Leu Thr Thr Ser Ala Ala Ile Phe Ala Ala Asp Ala Leu Lys Glu Lys
             -5                  1                5

GAT ATA TTT AAA ATA AAC CCA TGG ATG CCA ACA TTT GGA TTT GAA AAC         145
Asp Ile Phe Lys Ile Asn Pro Trp Met Pro Thr Phe Gly Phe Glu Asn
        10                  15                  20

ACA AGT GAA TTC AGA TTA GAT ATG GAC GAG CTT GTT CCT GGG TTT GAA         193
Thr Ser Glu Phe Arg Leu Asp Met Asp Glu Leu Val Pro Gly Phe Glu
    25                  30                  35

AAC AAA AGC AAA ATT ACC ATT AAG CTT AAA CCA TTT GAA GCT AAT CCC         241
Asn Lys Ser Lys Ile Thr Ile Lys Leu Lys Pro Phe Glu Ala Asn Pro
40                  45                  50                  55

GAA TTA GGC AAA GAC GAT CCA TTC TCA GCT TAC ATT AAG GTA GAA GAT         289
Glu Leu Gly Lys Asp Asp Pro Phe Ser Ala Tyr Ile Lys Val Glu Asp
                60                  65                  70

CTT GCA CTA AAA GCG GAA GGC AAA AAA GGC GAT CAA TTT AAA ATT GAC         337
Leu Ala Leu Lys Ala Glu Gly Lys Lys Gly Asp Gln Phe Lys Ile Asp
            75                  80                  85

GTG GGA GAT ATT ACA GCC CAA ATC AAT ATG TAC GAT TTT TTT ATT AAA         385
Val Gly Asp Ile Thr Ala Gln Ile Asn Met Tyr Asp Phe Phe Ile Lys
        90                  95                  100

ATA AGT ACT ATG ACA GAT TTT GAC TTT AAT AAA GAG TCT TTA TTT AGT         433
Ile Ser Thr Met Thr Asp Phe Asp Phe Asn Lys Glu Ser Leu Phe Ser
    105                 110                 115

TTT GCA CCT ATG ACT GGA TTT AAA AGC ACT TAC TAT GGA TTC CCA AGC         481
Phe Ala Pro Met Thr Gly Phe Lys Ser Thr Tyr Tyr Gly Phe Pro Ser
120                 125                 130                 135
```

```
AAT GAT AGG GCA GTA AGA GGG ACA ATT CTT GCA AGA GGT ACT TCT AAA         529
Asn Asp Arg Ala Val Arg Gly Thr Ile Leu Ala Arg Gly Thr Ser Lys
                140                 145                 150

AAC ATA GGA ACA ATT CAG CTG GGA TAC AAA CTC CCA AAA CTC GAC CTT         577
Asn Ile Gly Thr Ile Gln Leu Gly Tyr Lys Leu Pro Lys Leu Asp Leu
            155                 160                 165

ACA TTT GCA ATA GGG GGA ACA GGC ACG GGT AAC AGA AAT CAA GAG AAT         625
Thr Phe Ala Ile Gly Gly Thr Gly Thr Gly Asn Arg Asn Gln Glu Asn
            170                 175                 180

GAC AAA GAC ACT CCA TAC AAT AAA ACA TAT CAA GGA ATC CTT TAT GGA         673
Asp Lys Asp Thr Pro Tyr Asn Lys Thr Tyr Gln Gly Ile Leu Tyr Gly
        185                 190                 195

ATT CAA GCA ACA TGG AAA CCA ATA AAA AAT CTA CTT GAT CAA AAC GAA         721
Ile Gln Ala Thr Trp Lys Pro Ile Lys Asn Leu Leu Asp Gln Asn Glu
200                 205                 210                 215

GAT ACT AAA TCT GTA ATT GCA GAA ACA CCT TTT GAA TTA AAT TTT GGC         769
Asp Thr Lys Ser Val Ile Ala Glu Thr Pro Phe Glu Leu Asn Phe Gly
                220                 225                 230

TTG TCA GGA GCC TAT GGA AAC GAG ACA TTC AAT AAT TCA TCA ATA ACA         817
Leu Ser Gly Ala Tyr Gly Asn Glu Thr Phe Asn Asn Ser Ser Ile Thr
            235                 240                 245

TAC TCT TTA AAA GAT AAA TCC GTA GTT GGC AAC GAT TTA TTG AGC CCA         865
Tyr Ser Leu Lys Asp Lys Ser Val Val Gly Asn Asp Leu Leu Ser Pro
            250                 255                 260

ACT TTA TCA AAT TCT GCA ATT TTA GCA TCT TTT GGA GCT AAA TAT AAG         913
Thr Leu Ser Asn Ser Ala Ile Leu Ala Ser Phe Gly Ala Lys Tyr Lys
        265                 270                 275

CTT GGA TTA ACA AAA ATA AAC GAT AAA AAT ACC TAT CTT ATT TTG CAA         961
Leu Gly Leu Thr Lys Ile Asn Asp Lys Asn Thr Tyr Leu Ile Leu Gln
280                 285                 290                 295

ATG GGA ACT GAT TTT GGA ATA GAT CCT TTT GCA AGC GAT TTT TCT ATA        1009
Met Gly Thr Asp Phe Gly Ile Asp Pro Phe Ala Ser Asp Phe Ser Ile
                300                 305                 310

TTT GGA CAC ATC TCA AAA GCA GCG AAT TTC AAA AAA GAA ACA CCC TCA        1057
Phe Gly His Ile Ser Lys Ala Ala Asn Phe Lys Lys Glu Thr Pro Ser
            315                 320                 325

GAT CCT AAC AAA AAA GCT GAA ATA TTT GAT CCA AAT GGC AAT GCT CTT        1105
Asp Pro Asn Lys Lys Ala Glu Ile Phe Asp Pro Asn Gly Asn Ala Leu
        330                 335                 340

AAT TTC AGC AAA AAC ACA GAA TTG GGC ATT GCA TTT TCA ACA GGA GCA        1153
Asn Phe Ser Lys Asn Thr Glu Leu Gly Ile Ala Phe Ser Thr Gly Ala
345                 350                 355

AGT ATA GGT TTT GCT TGG AAT AAA GAT ACC GGT GAA AAA GAA TCC TGG        1201
Ser Ile Gly Phe Ala Trp Asn Lys Asp Thr Gly Glu Lys Glu Ser Trp
360                 365                 370                 375

GCG ATT AAA GGA TCT GAT TCC TAC AGT ACA AGA CTC TTT GGA GAA CAA        1249
Ala Ile Lys Gly Ser Asp Ser Tyr Ser Thr Arg Leu Phe Gly Glu Gln
                380                 385                 390

GAC AAA AAA TCT GGA GTT GCA TTG GGA ATA AGC TAT GGA CAA AAC CTT        1297
Asp Lys Lys Ser Gly Val Ala Leu Gly Ile Ser Tyr Gly Gln Asn Leu
            395                 400                 405

TAC AGA TCT AAA GAT ACA GAA AAA AGA TTA AAA ACC ATA TCT GAA AAT        1345
Tyr Arg Ser Lys Asp Thr Glu Lys Arg Leu Lys Thr Ile Ser Glu Asn
            410                 415                 420

GCA TTT CAA AGC TTA AAT GTT GAA ATT TCA AGC TAT GAA GAC AAC AAA        1393
Ala Phe Gln Ser Leu Asn Val Glu Ile Ser Ser Tyr Glu Asp Asn Lys
        425                 430                 435

AAA GGG ATT ATA AAT GGA TTA GGA TGG ATA ACA TCT ATC GGT CTT TAC        1441
Lys Gly Ile Ile Asn Gly Leu Gly Trp Ile Thr Ser Ile Gly Leu Tyr
```

-continued

```
                440             445             450             455
GAT ATT TTA AGA CAA AAA TCT GTA GAA AAC TAT CCT ACA ACA ATT TCA     1489
Asp Ile Leu Arg Gln Lys Ser Val Glu Asn Tyr Pro Thr Thr Ile Ser
                460             465             470

AGC ACC ACT GAA AAC AAT CAA ACT GAA CAA AGT TCA ACA AGC ACA AAG     1537
Ser Thr Thr Glu Asn Asn Gln Thr Glu Gln Ser Ser Thr Ser Thr Lys
            475             480             485

ACC ACA ACC CCT AAT CTG ACA TTT GAA GAT GCA ATG AAA CTC GGC TTG     1585
Thr Thr Thr Pro Asn Leu Thr Phe Glu Asp Ala Met Lys Leu Gly Leu
            490             495             500

GCC TTA TAT CTT GAT TAT GCA ATT CCA ATA GCA TCC ATT TCA ACA GAA     1633
Ala Leu Tyr Leu Asp Tyr Ala Ile Pro Ile Ala Ser Ile Ser Thr Glu
            505             510             515

GCA TAT GTA GTA CCT TAC ATT GGA GCA TAC ATT TTA GGA CCT TCT AAT     1681
Ala Tyr Val Val Pro Tyr Ile Gly Ala Tyr Ile Leu Gly Pro Ser Asn
520             525             530             535

AAA CTC TCA AGC GAT GCT ACA AAA ATT TAT TTA AAA ACA GGA CTT AGC     1729
Lys Leu Ser Ser Asp Ala Thr Lys Ile Tyr Leu Lys Thr Gly Leu Ser
            540             545             550

CTT GAA AAA CTA ATA AGA TTT ACA ACA ATT TCT CTT GGA TGG GAT TCA     1777
Leu Glu Lys Leu Ile Arg Phe Thr Thr Ile Ser Leu Gly Trp Asp Ser
            555             560             565

AAT AAC ATT ATA GAA CTT GCT AAT AAA AAC ACA AAT AAT GCT GCT ATT     1825
Asn Asn Ile Ile Glu Leu Ala Asn Lys Asn Thr Asn Asn Ala Ala Ile
            570             575             580

GGA AGT GCT TTC TTG CAA TTC AAA ATA GCC TAC AGC GGA AGC TAACAGCAAA 1877
Gly Ser Ala Phe Leu Gln Phe Lys Ile Ala Tyr Ser Gly Ser
            585             590             595

AGAAGGGCTT TGGCCCTTCT TTTTTATCTT TAAAAACAAT TGGGATTACC TTATATTTCT   1937

TTCCTTGCAA ATTTTTTCAT AAGCATCTTG AATTTTTATA AATTTATCAT TTGCATCTTT   1997

TTGTCTTACA GGATCATTTG CAAACTTATC AGGA                              2031

(2) INFORMATION FOR SEQ ID NO: 14:

(i) SEQUENCE CHARACTERISTICS:
         (A) LENGTH: 618 amino acids
         (B) TYPE: amino acid
         (D) TOPOLOGY: linear (ii) MOLECULE TYPE: protein (xi) SEQUENCE DESCRIPTION: SEQ ID NO: 14:

Met Lys Ser His Ile Leu Tyr Lys Leu Ile Ile Phe Leu Thr Thr Ser
-21 -20             -15             -10

Ala Ala Ile Phe Ala Ala Asp Ala Leu Lys Glu Lys Asp Ile Phe Lys
 -5              1               5              10

Ile Asn Pro Trp Met Pro Thr Phe Gly Phe Glu Asn Thr Ser Glu Phe
                15              20              25

Arg Leu Asp Met Asp Glu Leu Val Pro Gly Phe Glu Asn Lys Ser Lys
            30              35              40

Ile Thr Ile Lys Leu Lys Pro Phe Glu Ala Asn Pro Glu Leu Gly Lys
         45              50              55

Asp Asp Pro Phe Ser Ala Tyr Ile Lys Val Glu Asp Leu Ala Leu Lys
60              65              70              75

Ala Glu Gly Lys Lys Gly Asp Gln Phe Lys Ile Asp Val Gly Asp Ile
            80              85              90

Thr Ala Gln Ile Asn Met Tyr Asp Phe Phe Ile Lys Ile Ser Thr Met
         95              100             105
```

```
Thr Asp Phe Asp Phe Asn Lys Glu Ser Leu Phe Ser Phe Ala Pro Met
        110                 115                 120
Thr Gly Phe Lys Ser Thr Tyr Tyr Gly Phe Pro Ser Asn Asp Arg Ala
    125                 130                 135
Val Arg Gly Thr Ile Leu Ala Arg Gly Thr Ser Lys Asn Ile Gly Thr
140                 145                 150                 155
Ile Gln Leu Gly Tyr Lys Leu Pro Lys Leu Asp Leu Thr Phe Ala Ile
                160                 165                 170
Gly Gly Thr Gly Thr Gly Asn Arg Asn Gln Glu Asn Asp Lys Asp Thr
            175                 180                 185
Pro Tyr Asn Lys Thr Tyr Gln Gly Ile Leu Tyr Gly Ile Gln Ala Thr
        190                 195                 200
Trp Lys Pro Ile Lys Asn Leu Leu Asp Gln Asn Glu Asp Thr Lys Ser
    205                 210                 215
Val Ile Ala Glu Thr Pro Phe Glu Leu Asn Phe Gly Leu Ser Gly Ala
220                 225                 230                 235
Tyr Gly Asn Glu Thr Phe Asn Asn Ser Ser Ile Thr Tyr Ser Leu Lys
                240                 245                 250
Asp Lys Ser Val Val Gly Asn Asp Leu Leu Ser Pro Thr Leu Ser Asn
            255                 260                 265
Ser Ala Ile Leu Ala Ser Phe Gly Ala Lys Tyr Lys Leu Gly Leu Thr
        270                 275                 280
Lys Ile Asn Asp Lys Asn Thr Tyr Leu Ile Leu Gln Met Gly Thr Asp
    285                 290                 295
Phe Gly Ile Asp Pro Phe Ala Ser Asp Phe Ser Ile Phe Gly His Ile
300                 305                 310                 315
Ser Lys Ala Ala Asn Phe Lys Lys Glu Thr Pro Ser Asp Pro Asn Lys
                320                 325                 330
Lys Ala Glu Ile Phe Asp Pro Asn Gly Asn Ala Leu Asn Phe Ser Lys
            335                 340                 345
Asn Thr Glu Leu Gly Ile Ala Phe Ser Thr Gly Ala Ser Ile Gly Phe
        350                 355                 360
Ala Trp Asn Lys Asp Thr Gly Glu Lys Glu Ser Trp Ala Ile Lys Gly
    365                 370                 375
Ser Asp Ser Tyr Ser Thr Arg Leu Phe Gly Glu Gln Asp Lys Lys Ser
380                 385                 390                 395
Gly Val Ala Leu Gly Ile Ser Tyr Gly Gln Asn Leu Tyr Arg Ser Lys
                400                 405                 410
Asp Thr Glu Lys Arg Leu Lys Thr Ile Ser Glu Asn Ala Phe Gln Ser
            415                 420                 425
Leu Asn Val Glu Ile Ser Ser Tyr Glu Asp Asn Lys Lys Gly Ile Ile
        430                 435                 440
Asn Gly Leu Gly Trp Ile Thr Ser Ile Gly Leu Tyr Asp Ile Leu Arg
    445                 450                 455
Gln Lys Ser Val Glu Asn Tyr Pro Thr Thr Ile Ser Ser Thr Thr Glu
460                 465                 470                 475
Asn Asn Gln Thr Glu Gln Ser Ser Thr Ser Lys Thr Thr Thr Pro
                480                 485                 490
Asn Leu Thr Phe Glu Asp Ala Met Lys Leu Gly Leu Ala Leu Tyr Leu
            495                 500                 505
Asp Tyr Ala Ile Pro Ile Ala Ser Ile Ser Thr Glu Ala Tyr Val Val
        510                 515                 520
```

-continued

```
Pro Tyr Ile Gly Ala Tyr Ile Leu Gly Pro Ser Asn Lys Leu Ser Ser
    525                 530                 535

Asp Ala Thr Lys Ile Tyr Leu Lys Thr Gly Leu Ser Leu Glu Lys Leu
540                 545                 550                 555

Ile Arg Phe Thr Thr Ile Ser Leu Gly Trp Asp Ser Asn Asn Ile Ile
                560                 565                 570

Glu Leu Ala Asn Lys Asn Thr Asn Asn Ala Ala Ile Gly Ser Ala Phe
            575                 580                 585

Leu Gln Phe Lys Ile Ala Tyr Ser Gly Ser
        590                 595
```